United States Patent
Paulus et al.

(10) Patent No.: US 9,766,207 B2
(45) Date of Patent: Sep. 19, 2017

(54) AFFINITY METHODS AND COMPOSITIONS EMPLOYING ELECTRONIC CONTROL OF PH

(71) Applicants: Bio-Rad Laboratories, Inc., Hercules, CA (US); Technion Research & Development Foundation Ltd., Technion City (IL)

(72) Inventors: Aran Paulus, San Jose, CA (US); Camille Diges, Concord, CA (US); Roumen Bogoev, Hercules, CA (US); Inbal Zafir-Lavie, Kiryat Atta (IL); Sricharan Bandhakavi, Albany, CA (US); Annett Hahn-Windgassen, Sunnyvale, CA (US); Anton Posch, Grafting (DE); Elad Brod, Tivon (IL); Uri Sivan, Haifa (IL)

(73) Assignees: Bio-Rad Laboratories, Inc., Hercules, CA (US); Technion Research & Development Foundation Ltd., Haifa (IL)

( * ) Notice: Subject to any disclaimer, the term of this patent is extended or adjusted under 35 U.S.C. 154(b) by 495 days.

(21) Appl. No.: 14/468,730

(22) Filed: Aug. 26, 2014

(65) Prior Publication Data
US 2014/0360878 A1 Dec. 11, 2014

Related U.S. Application Data

(63) Continuation-in-part of application No. 13/668,651, filed on Nov. 5, 2012, now abandoned, and a
(Continued)

(51) Int. Cl.
*G01N 27/447* (2006.01)
*C07K 1/28* (2006.01)
(Continued)

(52) U.S. Cl.
CPC ......... *G01N 27/44795* (2013.01); *C07K 1/28* (2013.01); *C07K 1/36* (2013.01); *G01N 33/5302* (2013.01)

(58) Field of Classification Search
CPC ............................ G01N 27/44795; C07K 1/28
See application file for complete search history.

(56) References Cited

U.S. PATENT DOCUMENTS 4,868,130 A 9/1989 Hargreaves
4,880,513 A 11/1989 Davis et al.
(Continued)

FOREIGN PATENT DOCUMENTS

CN 102079781 A 6/2011
EP 0 979 868 A2 2/2000
(Continued)

OTHER PUBLICATIONS

The Extended European Searach Report dated Jun. 22, 2015 for European Patent Application No. 12844702.6, 7 pages.
(Continued)

*Primary Examiner* — Alexander Noguerola
(74) *Attorney, Agent, or Firm* — Kilpatrick Townsend and Stockton LLP

(57) ABSTRACT

Methods and devices for purifying, detecting, and collecting analytes fractionated based on pI, separating analytes via electrophoresis and pI, and purifying a target molecule using pI focusing and subsequent crystallization are provided.

15 Claims, 28 Drawing Sheets

Related U.S. Application Data continuation-in-part of application No. 13/669,023, filed on Nov. 5, 2012, now abandoned.

(60) Provisional application No. 61/555,564, filed on Nov. 4, 2011, provisional application No. 61/555,592, filed on Nov. 4, 2011, provisional application No. 61/555,674, filed on Nov. 4, 2011, provisional application No. 61/555,630, filed on Nov. 4, 2011, provisional application No. 61/555,713, filed on Nov. 4, 2011.

(51) Int. Cl.
*C07K 1/36* (2006.01)
*G01N 33/53* (2006.01)

(56) References Cited

U.S. PATENT DOCUMENTS

| | | | |
|---|---|---|---|
| 4,900,414 | A | 2/1990 | Sibalis |
| 4,911,808 | A * | 3/1990 | Hjerten ............ G01N 27/44795 204/452 |
| 4,936,962 | A | 6/1990 | Hatzidimitriu |
| 5,045,204 | A | 9/1991 | Dasgupta et al. |
| 5,078,853 | A | 1/1992 | Manning et al. |
| 5,082,548 | A | 1/1992 | Faupel et al. |
| 5,160,594 | A | 11/1992 | Huff et al. |
| 5,198,086 | A | 3/1993 | Chlanda et al. |
| 5,437,774 | A | 8/1995 | Lausten et al. |
| 5,567,293 | A | 10/1996 | Paleologou et al. |
| 5,646,001 | A | 7/1997 | Terstappen et al. |
| 5,650,055 | A | 7/1997 | Margolis |
| 5,773,645 | A | 6/1998 | Hochstrasser |
| 6,077,434 | A | 6/2000 | Srinivasan et al. |
| 6,084,091 | A | 7/2000 | Muller et al. |
| 6,129,832 | A | 10/2000 | Fuhr et al. |
| 6,225,129 | B1 | 5/2001 | Liu et al. |
| 6,660,150 | B2 | 12/2003 | Conlan et al. |
| 6,969,453 | B2 | 11/2005 | Ogle et al. |
| 6,969,614 | B1 | 11/2005 | Liotta et al. |
| 7,077,942 | B1 | 7/2006 | Conlan et al. |
| 7,390,389 | B2 | 6/2008 | Rossier et al. |
| 7,517,696 | B2 | 4/2009 | Srinivasan et al. |
| 7,615,354 | B2 | 11/2009 | Faupel et al. |
| 7,651,838 | B2 | 1/2010 | Paterlini-Brechot |
| 7,989,614 | B2 | 8/2011 | Deggerdal et al. |
| 8,293,095 | B2 | 10/2012 | Han et al. |
| 2002/0043462 | A1 | 4/2002 | Ivory et al. |
| 2003/0083823 | A1 | 5/2003 | Parekh et al. |
| 2003/0168576 | A1 | 9/2003 | Panattoni et al. |
| 2003/0205471 | A1 | 11/2003 | Speicher et al. |
| 2003/0206894 | A1 | 11/2003 | De Boer et al. |
| 2003/0226752 | A1 | 12/2003 | Vigh |
| 2004/0242849 | A1 | 12/2004 | Rylatt et al. |
| 2005/0087445 | A1 | 4/2005 | Speicher et al. |
| 2006/0029978 | A1 | 2/2006 | O'Neill et al. |
| 2006/0037860 | A1 | 2/2006 | Ogle et al. |
| 2007/0163884 | A1 | 7/2007 | Strand et al. |
| 2007/0205106 | A1 | 9/2007 | Vigh et al. |
| 2008/0009078 | A1 | 1/2008 | O'Neill |
| 2008/0035484 | A1 | 2/2008 | Wu et al. |
| 2009/0101491 | A1 | 4/2009 | Bukshpan |
| 2009/0145777 | A1 | 6/2009 | Srinivasan |
| 2010/0155243 | A1 | 6/2010 | Schneider et al. |
| 2010/0213065 | A1 * | 8/2010 | Astrom ................ C07K 1/14 204/459 |
| 2010/0307920 | A1 | 12/2010 | Sivan et al. |
| 2011/0195527 | A1 | 8/2011 | O'Neill et al. |
| 2012/0138468 | A1 | 6/2012 | Sivan et al. |
| 2012/0145548 | A1 | 6/2012 | Sivan et al. |

FOREIGN PATENT DOCUMENTS

| | | | |
|---|---|---|---|
| EP | 1456667 | B1 | 9/2004 |
| EP | 1748340 | A2 | 1/2007 |
| WO | 99/26724 | A2 | 6/1999 |
| WO | 01/36449 | A1 | 5/2001 |
| WO | 03/019172 | A2 | 3/2003 |
| WO | 2004/083405 | A2 | 9/2004 |
| WO | 2006/063625 | A1 | 6/2006 |
| WO | 2007/051492 | A1 | 5/2007 |
| WO | 2009/027970 | A2 | 3/2009 |
| WO | WO 2009027970 | A2 * | 3/2009 ........... G01N 27/447 |
| WO | 2009/133153 | A1 | 11/2009 |
| WO | 2010/048173 | A2 | 4/2010 |
| WO | 2010/118890 | A1 | 10/2010 |
| WO | 2011/021195 | A2 | 2/2011 |
| WO | 2011/021196 | A2 | 2/2011 |

OTHER PUBLICATIONS

Non-Final Office Action dated Aug. 5, 2015 for U.S. Appl. No. 13/803,564, 24 pages.
Notice of Allowance dated Sep. 8, 2015 for U.S. Appl. No. 13/669,012, 13 pages.
Armstrong et al., "Separating Microbes in the Manner of Molecules. 1. Capillary Electrokinetic Approaches", *Anal. Chem*, 71: 5465-5469 (1999).
Cabrera et al., "Continous concentration of bacteria in a microfluidic flow cell using electrokinetic techniques", *Eletrophoresis*, 22:355-362 (2001).
The Extended European Search Report dated Sep. 18, 2015 for European Patent Application No. 12845686.0, 11 pages.
Office Action from U.S. Appl. No. 13/669,012, mailed May 4, 2015, 22 pages.
Lu et al., "A Microfabricated Device for Subcellular Organelle Sorting", *Anal. Chem.*, 76:5705-5712 (2004).
Munce et al., "Microfabricated System for Parallel Single-Cell Capillary Electrophoresis",*Anal. Chem*, 76:4983-4989 (2004).
Pospichal et al., "Micropreparative Focusing of Proteins in Carrier-Ampholyte-free Solution with Electrically Controlled Composition of Electrolytes", *J. Microcolumn Separations*, 7(3): 213-219 (1995).
Prochakova et al., "The use of Carrier Ampholyte-Free Isoelectric Focusing for Proteomic Analysis", *Chromatographia Supplement*, 67:S55-61 (2008).
Zhan et al., "Development of a simple amopholyte-free isoelectric focusing slab electrophoresis for protein fractionation", *Journal of Chromotograph A*, 1216:2929-2933 (2009).
Supplementary European Search Report dated Apr. 15, 2015 for EP Application No. 12845192.9, 6 pages.
Hughes et al., "Microfluidic integration for automated targeted proteomic assays", *Proceeding of the National Academy of Sciences*, 109(16):5972-5977 (2012).
Knittle et al., "Laser-induced flurescence detector for capillary-based isoelectric immunoblot assay", *Analytical Chemistry*, 79(24): 9478-9483 (2007).
O'Neill et al., "Isoelectric focusing technology quantifies protein signaling in 25 cells", *Proceedings of the National Academy of Sciences, National Academy of Sciences*, 103(44): 16153-16158 (2006).
Shimura et al., "Affinity Probe Capillary Electrophoresis: Analysis of Recombinant Human Growth Hormone with a Fluorescent Labeled Antibody Fragment", *Analytical Chemistry*, 66(1): 9-15 (1994).
The International Search Report and Written Opinion from PCT/US2012/063571, dated Feb. 20, 2013 (14 pages).
The International Search Report and Written Opinion from PCT/US2013/032906, dated Jun. 14, 2013 (9 pages).
The International Search Report and Written Opinion from PCT/US2012/063601, dated Feb. 15, 2013 (12 pages).
The International Search Report and Written Opinion from PCT/US2013/026485, dated Apr. 19, 2013 (14 pages).
The International Search Report and Written Opinion from PCT/US2012/063502, dated Jan. 22, 2013 (13 pages).
U.S. Appl. No. 13/669,023, filed Nov. 5, 2012 (69 pages).
U.S. Appl. No. 13/668,651, filed Nov. 5, 2012 (43 pages).
U.S. Appl. No. 13/669,012, filed Nov. 5, 2012 (42 pages).
U.S. Appl. No. 13/768,253, filed Feb. 15, 2013 (90 pages).

(56) References Cited

OTHER PUBLICATIONS

U.S. Appl. No. 13/803,564, filed Mar. 14, 2013 (52 pages).
"Adjusting acidity with impunity." PHYSorg.com. Dec. 22, 2009. Retrieved at physorg.com/news180726696.html (author unknown).
"Isoelectric Focusing" from *European Pharmacopoeia Edition 5.0*, Chapter 2 "Methods of Analysis", Section 2.2.54 (p. 81-82). Published by the Council of Europe, Jun. 15, 2004.
"Isoelectric Focusing," *AES Application Focus* adapted from Chapter 7, Gel Electrophoresis of Proteins by David E. Garfin, pp. 197-268 in *Essential Cell Biology*, vol. 1: Cell Structure, A Practical Approach edited by John Davey and Mike Lord, Oxford University Press, Oxford UK (2003).
Ameridia, "Bipolar Membrane Electrodialysis—Applications of Bipolar Membrane Electrodialysis"; retrieved online at ameridia.com/htm/eba.html Jul. 12, 2011.
Ameridia, "Bipolar Membrane Electrodialysis—Process Description"; retrieved online at ameridia.com/htm/ebp.html Jul. 12, 2011.
Ameridia, "Bipolar Membrane Electrodialysis—Production of Organic or Amino Acids by Bipolar Membrane Electrodialysis"; retrieved online at ameridia.com/htm/ebc.html Jul. 12, 2011.
Amersham Pharmacia Biotech, "Hoefer IsoPrime IEF Purification Unit," User Manual (47 pages), 1999.
Bazinet et al.; "Bipolar Membrane Electroacidification to Produce Bovine Milk Casein Isolate"; *J. Agric. Food Chem.*; 47:5291-5296 (1999).
Bazinet et al.; "Effect of KCl and Soy Protein Concentrations on the Performance of Bipolar Membrane Electroacidification"; *J. Agric. Food. Chem.*; 45:2419-2425 (1997).
Bazinet et al.; "Effect of Number of Bipolar Membranes and Temperature on the Performance of Bipolar Membrane Electroacidification"; *J. Agric. Food Chem.*; 45:3788-3794 (1997).
Biotech Daily, "Daily news on ASX-listed biotechnology companies," 4 pages, Oct. 10, 2008.
Cao, Liming (2005) *Protein Separation with Ion-exchange Membrane Chromatography*. (Master's Thesis) Retrieved online at wpi.edu/Pubs/ETD/Available/etd-050405-174109/.
Chen et al.; "Electrodialytic Membrane Suppressors for Ion Chromatography Make Programmable Buffer Generators"; *Anal. Chem.*; 84:67-75 (2012) ePub Nov. 21, 2011.
Chen et al.; "pH- and Concentration-Programmable Electrodialytic Buffer Generator"; *Anal. Chem.*; 84:59-66(2012) ePub Dec. 12, 2011.
Cheng et al.; "High-performance protein separation by ion exchange membrane partitioned free-flowisoelectric focusing system"; *Chem. Eng. Sci.*; 63:2241-2251 (2008).
Cheng et al.; "Micro-pH Control by Breaking Water and Its Applications". 15th International Conference on Miniaturized Systems for Chemistry and Life Sciences. Oct. 2-6, 2011, Seattle, Washington, USA (3 pages).
Cheng et al.; "Microscale pH Regulation by Breaking Water"; *Biomicrofluidics*; vol. 5, 046502, published online Nov. 2, 2011 (8 pages).
Cretich et al.; "Electroosmotic flow suppression in capillary electrophoresis: Chemisorption of trimethoxy silane-modified polydimethylacrylamide"; *Electrophoresis*; 26:1913-1919 (2005).
Das et al.; "Effects of separation length and voltage on isoelectric focusing in a plastic microfluidic device"; *Electrophoresis*; 27:3619-3626 (2006).
Denver Instrument, "Titration—Coulometric Karl Fischer Titration" brochure. (n.d.).
Dionex Corporation, "Eluent Suppressors for Ion Chromatography," Data Sheet (24 pages), 2010.
DKK-TOA Corporation, "AUT-701 Automatic Titrator" brochure. Jan. 10, 2008.
Douglas Instruments, "Oryx8" brochure. (n.d.).
Gregor, H.; "Ion-Exchange Membranes—Correlation Between Structure and Function"; *Pure Appl. Chem.*; 16(2-3)329-350 (1968).
Horvath et al.; "Multifunctional apparatus for electrokinetic processing of proteins"; *Electrophoresis*; 15:968-971 (1994).

Huang et al.; "Application of electrodialysis to the production of organic acids: State-of-the-art and recent developments"; *J. Membr. Sci.*; 288:1-12 (2007) ePub Nov. 25, 2006.
Huang et al.; "Capillary Isoelectric Focusing without Carrier Ampholytes" *Anal. Chem.*; 72:4758-4761 (2000).
Huang et al.; "Digitally Controlled Electrophoretic Focusing"; *Anal. Chem.*; 71(8):1628-1632 (1999) ePub Mar. 9, 1999.
Huang et al.; "The transitional isoelectric focusing process"; *Anal. Bioanal. Chem.*; 382:783-788 (2005).
Ivory, C.F.; "A Brief Review of Alternative Electrofocusing Techniques"; *Separation Science and Technology*; 35(11):1777-1793 (2000).
Jong et al.; "Membranes and microfluidics: a review"; *Lab Chip*; (6): 1125-1139 (2006).
Karaltay Scientific Instruments, "Laboratory electrochemical analytical instruments—Automatic potentiometric titrators." 5 pages (n.d.).
Karimi et al.; "Electroosmotic flow through polymer electrolyte membranes in PEM fuel cells"; *Journal of Power Sources*; 140:1-11.
Kelly et al.; "Electric field gradient focusing"; *J. Sep. Sci.*; 28:1985-1993.
Kohlmann, F.J.; "What is pH and how is it measured?—A Technical Handbook for Industry"; Lit. No. G004. 24 pages. Hach Company (2003).
Lee et al.; "Polymer Electrolyte Membranes for Fuel Cells"; *J. Ind. Eng. Chem.*; 12(2):175-183 (2006).
Li et al.; "An electrokinetic bioreactor: using direct electric current for enhanced lactic acid fermentation and product recovery"; *Tetrahedron*; 60:655-661 (2004).
Lutin et al.; "Keep it natural ! Adjusting the pH of food products without chemical additives thanks to Bipolar Membrane Electrodialysis." Presented on May 15, 2007. NAMS 2007 Annual Meeting May 11-16, 2007, Orlando, Florida (3 pages).
Ly, Linda. (2008). *Development of Selective Electrophoresis for Proteins and Peptides within Proteomes*. (Doctoral Dissertation) Retrieved from web at http://www.unsworks.unsw.edu.au/primo_library/libweb/action/dlDisplay.do?vid=UNWORKS &docId=unsworks_4279.
Mettler Toledo, "Compact Titrator G20" brochure. Sep. 2009.
Michél et al.; "Protein fractionation in a multicompartment device using Off-Gel™ isoelectric focusing"; *Electrophoresis*; 24:3-11 (2003).
Montgomery et al.; "Dynamic Isoelectric Focusing for Proteomics"; *Anal. Chem.*; 78:6511-6518 (2006).
Nagasubramanian et al.; "Use of Bipolar Membranes for Generation of Acid and Base—An Engineering and Economic Analysis"; *J. Membr. Sci.*; 2:109-124 (1977).
Nguyen et al.; "A Water and Heat Management Model for Proton-Exchange-Membrane Fuel Cells"; J. Electrochem. Soc.; *J. Electrochem. Soc.*, 140(8):2178-2186 (Aug. 1993).
NuSep Press Release, "NuSep Increases Profit Forecast to $1m after it Acquires BioInquire and completes Placement at 30c"; 2009 (4 pages).
NuSep Press Release, "NuSep Investor Presentations"; 2009 (4 pages).
NuSep, "Desalting protein samples by electro-dialysis using the ProteomeSep MF10," Application Note NAN004 (2 pages), n.d.
NuSep, "ProteomeSep—MF10 Membrane Fractionation Instrument for protein separations," Operators Manual (22 pages), 2008.
NuSep, "Removal of urea from protein samples using the ProteomeSep MF10," Application Note NAN005 (2 pages), n.d.
NuSep, "Separation of protein based on isoelectric point using the NuSep MF10," Application Note NAN001, Insert PII-055v1.1 (2 pages), n.d.
NuSep, MF10 Brochure (8 pages), (2008).
Ogle et al.; "Preparative-scale isoelectric trapping separations using a modified Gradiflow unit"; *J. Chromatogr. A*; 979:155-161 (2002).
PC Cell GmbH, "PCCell ED 64 0 04" brochure. (n.d.).
Pearson et al.; "Production of synthetic ampholytes for isolectric focusing." (1979). *Nebraska Game and Parks Commission—White Papers, Conference Presentations, & Manuscripts*. Paper 13. Retrived onling at digitalcommons.unl.edu/nebgamewhitepap/13.

(56) References Cited

OTHER PUBLICATIONS

Piruska et al.; "The autofluorescence of plastic materials and chips measured under laser irradiation"; *Lab Chip*; 5:1348-1354 (2005) ePub Nov. 1, 2005.
Pospíchal et al.; "Analytical aspects of carrier ampholyte-free isoelectric focusing"; *J. Chromatog. A*; 918:195-203 (2001).
Pospíchal et al.; "Electrically controlled electrofocusing of ampholytes between two zones of modified electrolyte with two different values of pH"; *J. Chromatog.*; 638:179-186 (1993).
Pospíchal et al.; "Micropreparative Focusing of Proteins in Carrier-Ampholyte-free Solution with Electrically Controlled Compositions of Electrolytes"; *J. Microcolumn Separations*; 7(3):213-219 (1995).
Ramierz et al.; "Current-voltage curves of bipolar membranes"; *J. Appl. Phys.*, 72(1):259-264 (Jul. 1992).
Silvertand et al.; "Recent developments in capillary isoelectric focusing"; *J. Chromatog. A*; 1204:157-170 (2008).
Silvertand, Linda H.H. (2009) Isoelectric Focusing: Sample Pretreatment—Separation—Hyphenation. (Doctoral Dissertation) Retreived online at igitur-archive.library.uu.nl/dissertations/2010-0106-200200/UUindex.html.
Song et al.; "Fabrication and Characterization of Photpatterned Polymer Membranes for Protein Concentration and Dialysis in Microchips" in Hilton Head, South Carolina MEMS Workshop Jun. 6-10, 2004 (May 2004).
Standard Operating Procedure, "SOP for Gradiflow MF10 (prototype)," 6 pages, (2007).
TechniKrom, "New cGMP Bioprocessing Tool: Automated Rapid pH Adjustment Systems" brochure. (2006).
Thomas et al.; "Gradipore™—The Preparative Electrophoresis System, Gradiflow™"; Poster MB-04, 1 page, n.d.
Thomas et al.; "Preparative electrophoresis: a general method for the purification of polyclonal antibodies"; J. Chromatogr. A; 944:161-168. (2002).
Thomas et al.; Gradipore, "Comparison of Gradiflow and Affinity Chromatography Methods of Antibody Preparation," Gradipore Application Note AN3004 (Jul. 2003).
Thormann et al.; "High-resolution computer simulation of the dynamics of isoelectric focusing using carrier ampholytes: Focusing with concurrent electrophoretic mobilization is an isotachophoretic process"; Electrophoresis; 27:968-983 (2006).
Tongwen et al.; "Citric acid production by electrodialysis with bipolar membranes"; Chemical Engineering and Processing; 41:519-524 (2002).
Walter et al.; "Protein microarrays: Reduced autofluorescence and improved LOD"; *Eng. Life Sci.*; 10(2):103-108 (2010).
Wei et al.; "One-step concentration of analytes based on dynamic change in pH in capillary zone electrophoresis"; *Anal. Chem.*; 74:934-940 (2002).
Wei et al.; "On-line concentration of proteins and peptides in capillary zone electrophoresis with an etched porous joint"; *Anal. Chem.*; 74:3899-3905 (2002).
Wellhausen et al.; "Facing Current Quantification Challenges in ProteinMicroarrays"; *J. Biomed. Biotechnol.*; vol. 2012, Article ID 831347, 8 pages, ePub Apr. 24, 2012.
Westermeier et al.; "Protein Detection Methods in Proteomics Research"; *Bioscience Reports*; 25(1/2):19-32 (2005).
Wilhelm, Friedrich G. (2001) Bipolar Membrane Electrodialysis. (Doctoral Thesis) Retrieved online at tup.utwente.nl/uk/catalogue/technical/electrodialysis.
Wong et al.; "Application of bipolar electrodialysis to *E. coli* fermentation for simultaneous acetate removal and pH control"; Biotechnol. Lett.; 32:1053-1057 (2010) ePub Apr. 11, 2010.
Wong, Michael. (2011) Application of electrodialysis in integrated microbial fermentation and enzymatic biotransformation processes. (Doctoral Thesis) Retreived online at discovery.ucl.ac.uk/1310480/1/1310480.pdf.
Wu et al.; "Isoelectric focusing sample injection for capillary electrophoresis of proteins"; *Electrophoresis*; 26:563-570 (2005).
Xu et al.; "Development of bipolar membrane-based processes"; *Desalination*; 140:247-258 (2001).
Xu et al.; "Electrodialysis-Based Separation Technologies: A Critical Review"; *American Institute of Chemical Engineers Journal*; 54(12):3147-3159 (2008) ePub Oct. 2, 2008.
Xu et al.; "Ion exchange membranes: State of their development and perspective"; *J. Membr. Sci.*; 263:1-29 (2005).
Zhang et al.; "Isoelectric Focusing Sample Injection for Capillary Zone Electrophoresis in a Fused Silica Capillary"; *Analytical Sciences*; 22:1039-1041 (Jul. 2006).
Zuo et al.; "A Method for Global Analysis of Complex Proteomes Using Sample Prefractionation by Solution Isoelectrofocusing Prior to Two-Dimensional Electrophoresis"; *Anal. Biochem.*; 284:266-278 (2000).
Office Action from U.S. Appl. No. 13/669,023, mailed Sep. 9, 2013.
Office Action from U.S. Appl. No. 13/669,023, mailed Mar. 26, 2014.

\* cited by examiner

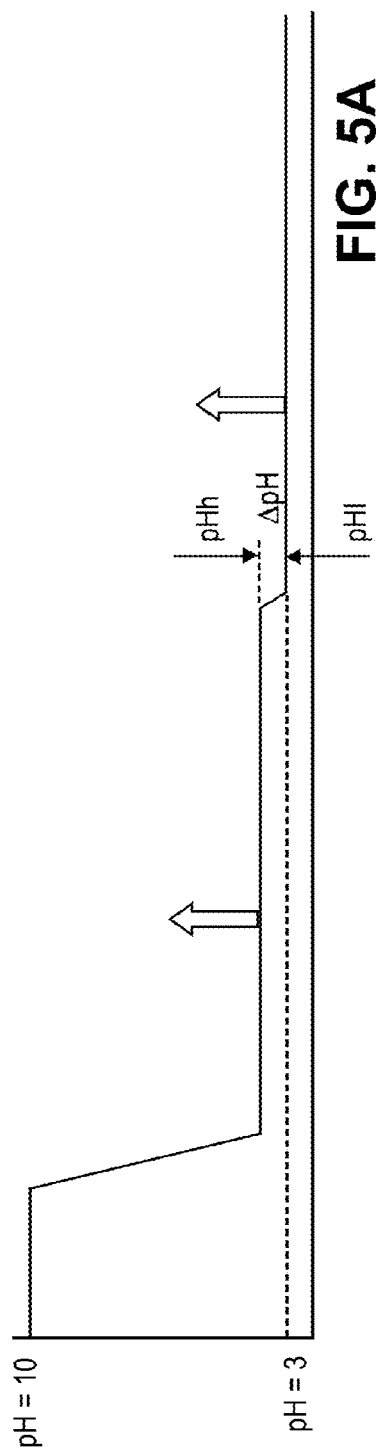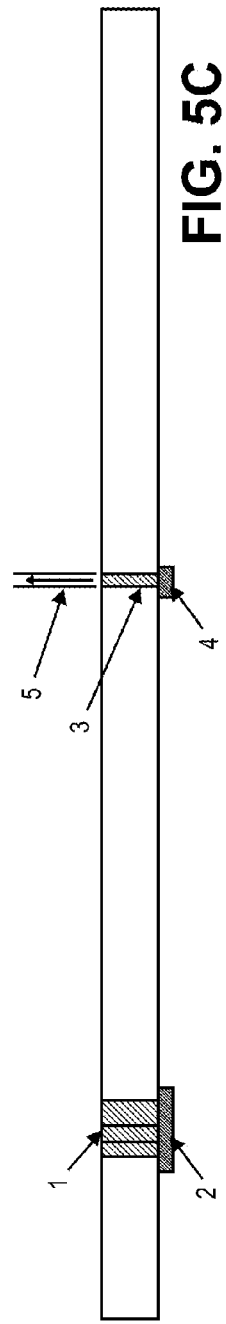

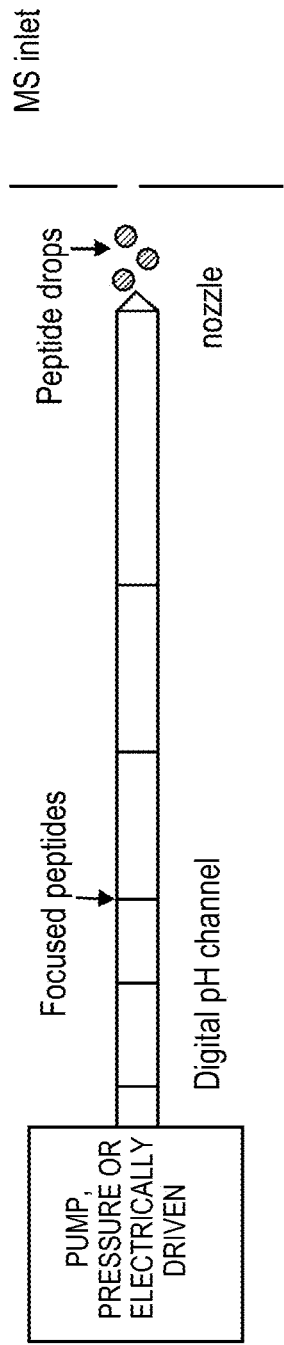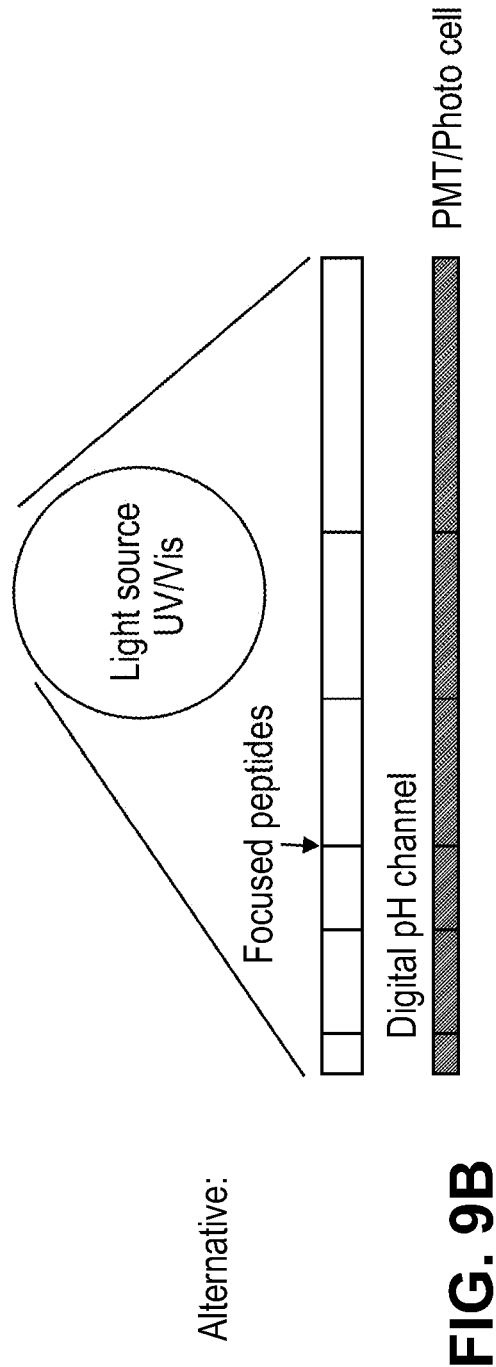
FIG. 9A
FIG. 9B

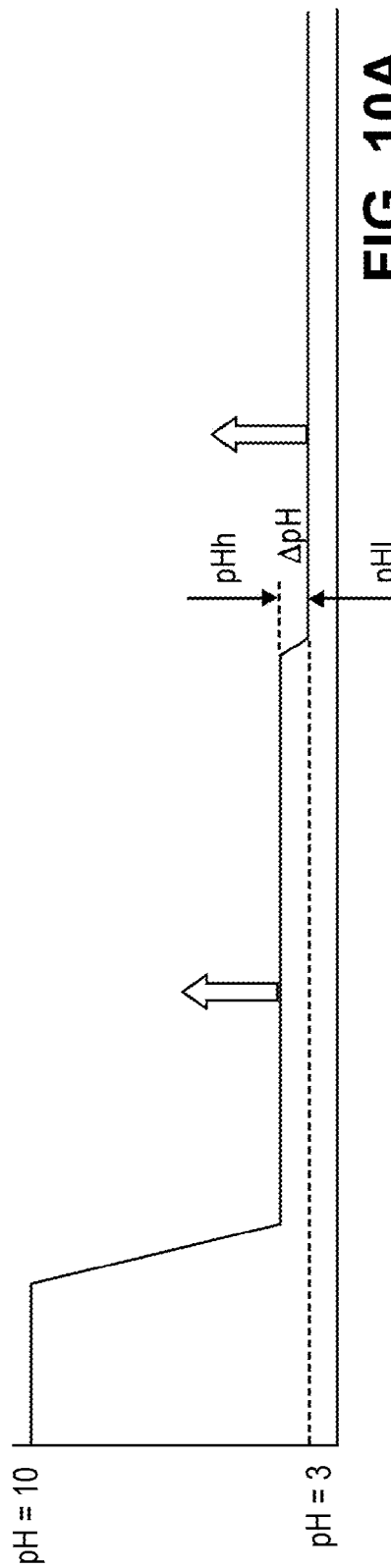
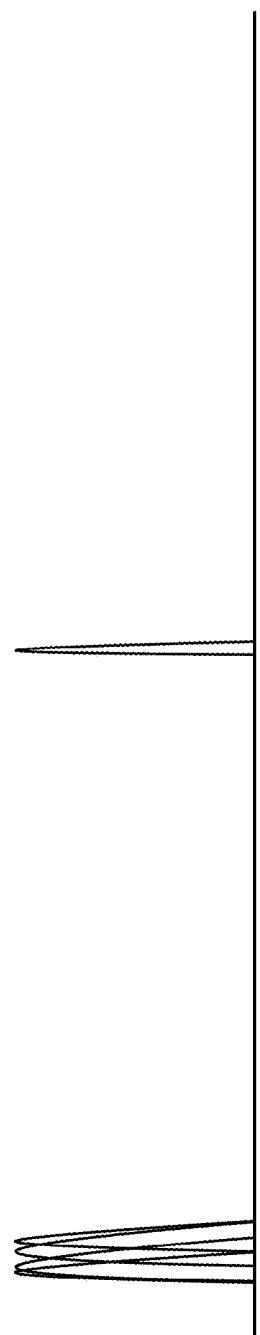
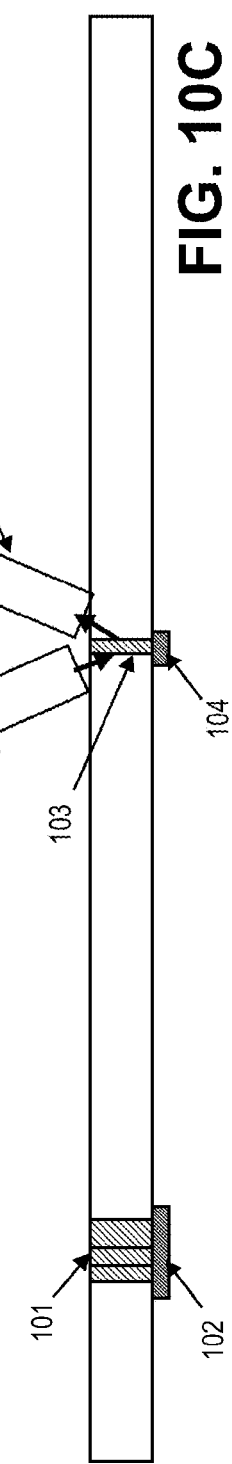
FIG. 10A
FIG. 10B
FIG. 10C 180-135µA for 90 min;
0µA thereafter;
300V a/c channel, 18-18.5mA current 0µA (No H⁺ injection);
300V across channel; 18-18.5 mA current

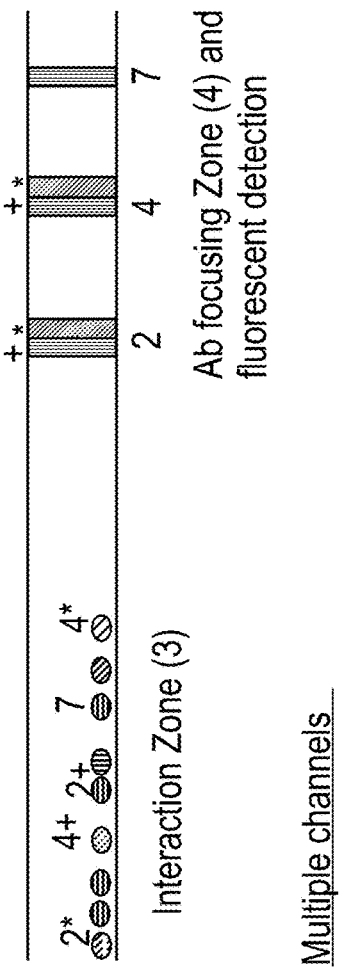
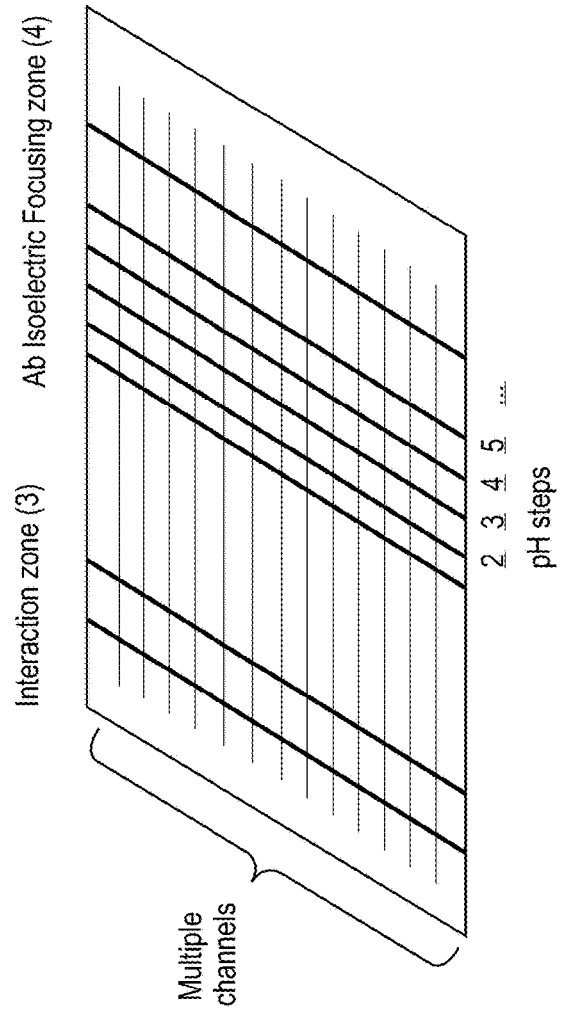
FIG. 23

AFFINITY METHODS AND COMPOSITIONS EMPLOYING ELECTRONIC CONTROL OF PH

CROSS-REFERENCE TO RELATED APPLICATIONS

This application is a continuation in part of U.S. application Ser. No. 13/668,651, filed on Nov. 5, 2012, which claims the benefit of priority to U.S. Provisional Application Nos. 61/555,564, 61/555,592, and 61/555,674, all filed Nov. 4, 2011. This application is also a continuation in part of U.S. application Ser. No. 13/669,023, filed on Nov. 5, 2012, which claims the benefit of priority to U.S. Provisional Application Nos. 61/555,630 and 61/555,713, both filed on Nov. 4, 2011. The contents of each of the foregoing U.S. Provisional and Non-Provisional application are incorporated by reference in their entirety for all purposes.

BACKGROUND

Detection of target molecules is useful in many industries. For example, detection and quantification of biological molecules is a basis for disease diagnostics. Detection and/or purification can be performed using techniques that, at least in part, utilize differences in isoelectric point between target molecules and other molecules in a sample. Such methods include those that involve isoelectric focusing. Current isoelectric focusing based protein/peptide fractionation technologies suffer from at least two shortcomings. First, samples are separated over a fixed or limited pH range resulting in non-optimal fractionation of various samples. Second, pH gradients required for sample fractionation are established via chemicals (ampholytes) resulting in contamination of fractionated samples with chemicals and (potential) interference of downstream analysis.

BRIEF SUMMARY OF THE INVENTION

In some embodiments, the present invention provides a device for separating and detecting analytes in a sample, the device comprising a chamber for containing a solution having a plurality of molecular analytes along an axis, having a sample injection port at a first end of an axis of the chamber and an outlet at a second end of the axis; an electrical source for applying an electric field along the axis in the chamber; a one or more ion sources separated by a bipolar membrane from said chamber, for establishing a pH gradient along said axis in said chamber by injecting ion flows, capable of forming one or more pH steps in a pH gradient; a controller which operates said one or more ion sources to adjust the pH gradient so as to induce migration of the molecular analytes separately along the axis; and one or more outlet(s) to allow for receipt of one or more analyte from the outlet(s) to vessels or analytic instruments such as a mass spectrometer or other detection system. In some embodiments, the one or more ion sources is (are) a proton injector(s) or a hydroxide injector(s).

In some embodiments, the present invention provides a method of separating one or more target protein from a sample. In some embodiments, the method comprises providing into a chamber a sample comprising a mixture of proteins including one or more target protein (or other target molecule, including but not limited to a nucleic acid), wherein the chamber comprises a first and second electrode and at least one proton injector or hydroxide injector positioned on a wall of the chamber between the electrodes, and separated from the sample in the chamber by a bipolar membrane; generating a pH gradient in the chamber with the proton injector or the hydroxide injector, and applying a voltage across the electrodes, thereby positioning proteins in the chamber based on the isoelectric point (pI) of the proteins; capturing one or more protein in a port in fluid communication to the channel; and submitting the one or more captured protein to gel electrophoresis.

In some embodiments, the electrophoresis is polyacrylamide gel electrophoresis. In some embodiments, the method further comprises collecting the one or more protein from the electrophoresis gel.

In some embodiments, the present invention provides a method of separating one or more target protein (or other target molecule, including but not limited to a nucleic acid) from a sample, the method comprising, providing into a chamber a sample comprising a mixture of proteins including one or more target protein, wherein the chamber is attached to one or more ion sources separated by a bipolar membrane from said chamber, for establishing a pH gradient along said axis in said chamber by injecting ion flows, capable of forming one or more pH steps in a pH gradient; submitting the proteins in the chamber to electrophoresis; and subsequently generating a pH gradient in the chamber with a proton and/or hydroxide injector, thereby position proteins in the chamber based on their isoelectric point (pI) of the proteins.

In some embodiments, the electrophoresis is continued during generation of the pH gradient. In some embodiments, the method of separating one or more target protein from a sample also includes collecting the one or more target protein.

In some embodiments, the present invention provides a device for separating a plurality of molecular analytes according to both isoelectric points and electrophoretic mobility, the device comprising, a chamber for containing a solution having a plurality of molecular analytes along an axis, wherein the chamber contains one or more ports in fluid communication with the chamber and positioned in the chamber to capture a desired analyte based on the analyte's pI, or movable to position the one or more port at one or more desired position; an electrical source for applying an electric field along the axis in the chamber; a one or more proton/hydroxide sources for establishing a pH gradient along said axis in said chamber by injecting ion flows, capable of forming one or more pH steps in a pH gradient; a controller which operates said one or more ion sources to adjust the pH gradient so as to induce migration of the molecular analytes separately along the axis; and one or more electrophoresis channel(s) in fluid communication to said one or more port, thereby allowing for electrophoresis of an analyte capture in said one or more port. In some embodiments, the proton or hydroxide sources is (are) a proton injector(s) or a hydroxide injector(s) separated from the chamber by a bipolar membrane.

In some embodiments, the present invention provides a device for separating a plurality of molecular analytes according to both isoelectric points and electrophoretic mobility, the device comprising, a chamber for containing a solution having a plurality of molecular analytes along an axis; an electrical source for applying an electric field along the axis in the chamber; a one or more proton/hydroxide sources for establishing a pH gradient along said axis in said chamber by injecting ion flows, capable of forming one or more pH steps in a pH gradient; a controller which operates said one or more ion sources to adjust the pH gradient so as to induce migration and capturing of the molecular analytes separately along the axis. In some embodiments, the proton or hydroxide sources is (are) a proton injector(s) or a hydroxide injector(s) separated from the chamber by a bipolar membrane.

In some embodiments, the chamber contains a sieving medium suitable for electrophoresis. In some embodiments, the chamber contains one or more ports in fluid communication with the chamber and positioned in the chamber to capture a desired analyte based on the analyte's pI, or movable to position the one or more port at one or more desired position.

In some embodiments, the present invention provides a method of purifying a target protein from a sample, the method comprising, providing into a chamber a sample comprising a mixture of proteins including the target protein; generating a pH gradient in the chamber with a proton and/or hydroxide injector, thereby positioning proteins in the chamber based on the isoelectric point (pI) of the proteins; collecting the target protein, thereby purifying the target protein from other components of the mixture; and crystallizing the protein following capture.

In some embodiments, the target protein is collected via a port in fluid communication to the channel. In some embodiments, a plurality of target proteins are collected in multiple ports fluid communication to the channel.

In some embodiments, methods of detecting a target analyte are provided. In some embodiments, the method comprises, providing into a chamber a sample comprising a mixture of molecules including one or more target analyte; generating a pH step gradient in the chamber with one or more proton and/or hydroxyl injector, thereby positioning analytes in the chamber based on the isoelectric point (pI) of the analytes, wherein the target analyte is precipitated and/or adhered to the chamber once positioned at the location in the chamber corresponding to the target analyte pI; and detecting the precipitated/adhered analyte.

In some embodiments, the precipitated/adhered analyte is captured in or adjacent to an opening (e.g., a slit) in the surface of the chamber. In some embodiments, the detecting comprises contacting the precipitated analyte with an affinity agent that specifically binds the analyte. In some embodiments, the affinity agent is an antibody. In some embodiments, the binding of the affinity agent to the target analyte is detected by contacting the bound affinity agent with a secondary antibody and subsequently detecting the presence of the secondary antibody with a detectable label.

In some embodiments, the target analyte is a protein. In some embodiments, the target analyte is a post-translationally-modified protein.

Also provided are methods of capturing a target analyte from a mixture. In some embodiments, the method comprises, providing into a chamber a sample comprising a mixture of molecules including one or more target analyte, wherein one or more affinity specific for the target analyte is bound to a position on the chamber; generating a pH gradient in the chamber with one or more proton and/or hydroxyl injector, thereby positioning analytes in the chamber based on the isoelectric point (pI) of the analytes, wherein the target analyte is positioned at its pI in proximity to the bound affinity agent(s), under conditions such that the target analyte is bound to the affinity agent(s).

In some embodiments, the method further comprises changing the pH gradient once the target analyte is in proximity to the bound affinity agent(s), thereby promoting conditions for binding.

In some embodiments, the method further comprises detecting the presence or absence of the target analyte.

In some embodiments, the method further comprises collecting the target analyte.

In some embodiments, the mixture comprises a sufficient amount of a non-ionic detergent or other agent (including but not limited to an organic solvent(s)) to promote solubility of the target analyte.

In some embodiments, the target analyte is a protein. In some embodiments, the affinity agent is an antibody.

Also provided is a device for capturing a target analyte from a mixture. In some embodiments, the device comprises, a chamber for containing a solution having a plurality of molecular analytes along an axis, wherein the chamber comprises one or more opening (e.g., slit) in the surface of the chamber for collection of precipitated target analyte; an electrical source for applying an electric field along the axis in the chamber; a one or more ion sources for establishing a pH gradient along said axis in said chamber by injecting ion flows, capable of forming one or more pH steps in a pH gradient; a controller which operates said one or more ion sources to adjust the pH gradient so as to induce migration of the molecular analytes separately along the axis.

In some embodiments, the device comprises, a chamber for containing a solution having a plurality of molecular analytes along an axis, wherein one or more affinity agents are bound to the interior surface of the chamber at a position on the chamber; an electrical source for applying an electric field along the axis in the chamber; a one or more ion sources for establishing a pH gradient along said axis in said chamber by injecting ion flows, capable of forming one or more pH steps in a pH gradient; a controller which operates said one or more ion sources to adjust the pH gradient so as to induce migration of the molecular analytes separately along the axis. In some embodiments, the affinity agent is an antibody.

Also provided is a method of purifying a target analyte from a mixture. In some embodiments, the method comprises, providing into a chamber a sample comprising a mixture of molecules including one or more target analyte, wherein the chamber comprises a solid support linked to an affinity agent specific for the target analyte, wherein the solid support is positioned at a location in the chamber substantially corresponding to the pI of the target analyte following generation of a pH gradient; generating the pH gradient in the chamber with a proton and/or hydroxyl injector, thereby positioning analytes in the chamber based on the isoelectric point (pI) of the analytes, such that the position of the target analyte is in proximity to the solid support, thereby binding the target analyte to the affinity agent; washing the chamber, thereby removing unbound components of the mixture; and eluting the target analyte from the affinity agent, thereby purifying the target analyte.

In some embodiments, the eluting comprises changing the solution in the chamber. In some embodiments, the eluting comprises changing the pH in proximity to the affinity ligand using the proton or hydroxyl injector. In some embodiments, the affinity agent is an antibody. In some embodiments, the solid support is a bead or microparticle. In some embodiments, the target analyte is a protein. In some embodiments, the method further comprises collecting the eluted target analyte.

In some aspects, a method of purifying a target analyte from a mixture is provided. In some embodiments, the method comprises, providing into a chamber a sample comprising a mixture of molecules including one or more target analyte, wherein the chamber comprises a solid support linked to an affinity agent specific for the target analyte, wherein the solid support is positioned at a location in the chamber substantially corresponding to the pI of the target analyte following generation of a pH gradient; generating the pH gradient in the chamber with a proton and/or hydroxide injector, thereby positioning analytes in the chamber based on the isoelectric point (pI) of the analytes, such that the position of the target analyte is in proximity to the solid support, thereby binding the target analyte to the affinity agent; washing the chamber, thereby removing unbound components of the mixture; and eluting the target analyte from the affinity agent, thereby purifying the target analyte.

In some embodiments, the eluting comprises changing the solution in the chamber.

In some embodiments, the eluting comprises changing the pH in proximity to the affinity ligand using the proton or hydroxide injector.

In some embodiments, the affinity agent is an antibody.

In some embodiments, the solid support is a bead or microparticle.

In some embodiments, the target analyte is a protein. In some embodiments, the target analyte is a non-proteinaceous small-molecules (eg: drugs, metabolite, etc.).

In some embodiments, the method further comprises collecting the eluted target analyte.

Also provided is a device for purifying a target analyte from a mixture. In some embodiments, the device comprises a chamber for containing a solution having a plurality of molecular analytes along an axis, wherein the chamber comprises a solid support linked to an affinity agent specific for the target analyte; an electrical source for applying an electric field along the axis in the chamber; a one or more ion sources for establishing a pH gradient along said axis in said chamber by injecting ion flows, capable of forming one or more pH steps in a pH gradient; and a controller which operates said one or more ion sources to adjust the pH gradient so as to induce migration of the molecular analytes separately along the axis. In some embodiments, the affinity agent is an antibody.

Also provided is a method of detecting a target analyte. In some embodiments, the method comprises providing into a chamber a sample comprising a mixture of molecules including one or more target analyte; generating a pH gradient in the chamber with one or more proton and/or hydroxide injector, thereby positioning analytes in the chamber based on the isoelectric point (pI) of the analytes, wherein the target analyte is precipitated once positioned at its pI; and detecting the precipitated analyte.

In some embodiments, the precipitated analyte is captured in a opening (e.g., slit) in the surface of the chamber.

In some embodiments, the detecting comprises contacting the precipitated/adhered analyte with an affinity agent that specifically binds the analyte.

In some embodiments, the affinity agent is an antibody. In some embodiments, the binding of the affinity agent to the target analyte is detected by contacting the bound affinity agent with a secondary antibody and subsequently detecting the presence of the secondary antibody with a detectable label.

In some embodiments, the target analyte is a protein. In some embodiments, the target analyte is a non-proteinaceous small-molecule (e.g., a drug, metabolite, etc.).

In some embodiments, the target analyte is a post-translationally-modified protein.

Also provided is a method of capturing a target analyte from a mixture. In some embodiments, the method comprises, providing into a chamber a sample comprising a mixture of molecules including one or more target analyte, wherein one or more affinity specific for the target analyte is bound to a position on the chamber; generating a pH gradient in the chamber with one or more proton and/or hydroxide injector, thereby positioning analytes in the chamber based on the isoelectric point (pI) of the analytes, wherein the target analyte is positioned at its pI in proximity to the bound affinity agent(s), under conditions such that the target analyte is bound to the affinity agent(s).

In some embodiments, the method further comprises changing the pH gradient once the target analyte is in proximity to the bound affinity agent(s), thereby promoting conditions for binding.

In some embodiments, the method further comprises detecting the presence or absence of the target analyte.

In some embodiments, the method further comprises collecting the target analyte.

In some embodiments, the mixture comprises a sufficient amount of a non-ionic detergent or other agent (including but not limited to an organic solvent(s)) to promote solubility of the target analyte.

In some embodiments, the target analyte is a protein. In some embodiments, the affinity agent is an antibody.

Also provided is a device for capturing a target analyte from a mixture. In some embodiments, the device comprises a chamber for containing a solution having a plurality of molecular analytes along an axis, wherein the chamber comprises one or more opening (e.g., slit) in the surface of the chamber for collection of precipitated target analyte; an electrical source for applying an electric field along the axis in the chamber; a one or more ion sources for establishing a pH gradient along said axis in said chamber by injecting ion flows, capable of forming one or more pH steps in a pH gradient; a controller which operates said one or more ion sources to adjust the pH gradient so as to induce migration of the molecular analytes separately along the axis.

Also provided is a device for capturing a target analyte from a mixture. In some embodiments, the device comprises a chamber for containing a solution having a plurality of molecular analytes along an axis, wherein one or more affinity agents are bound to the interior surface of the chamber at a position on the chamber; an electrical source for applying an electric field along the axis in the chamber; a one or more ion sources for establishing a pH gradient along said axis in said chamber by injecting ion flows, capable of forming one or more pH steps in a pH gradient; a controller which operates said one or more ion sources to adjust the pH gradient so as to induce migration of the molecular analytes separately along the axis.

In some embodiments, the affinity agent is an antibody.

Methods of detecting for presence, absence, or quantity of a target analyte in a sample are also provided. In some embodiments, the method comprises providing a chamber comprising a first and a second electrode, wherein a first and second sub-area of the compartment are between the electrodes;

localizing components of a biological sample to the first sub-area of a compartment;

contacting the localized components with a labeled affinity agent that specifically binds the target analyte, if present, under conditions such that the affinity agent binds the target analyte, if present;

applying a current between the first and second electrode thereby moving the affinity agent that bound to the target analyte, if any, to a second sub-area of the compartment, wherein solution in proximity to the second sub-area has a pH controlled by one or more proton/hydroxide injector(s); and detecting the presence or quantity of the affinity agent bound to the target analyte at the second sub-area of the compartment, thereby detecting the presence or quantity of a target analyte in a sample.

In some embodiments, the affinity agent is an antibody.

In some embodiments, the method further comprises removing labeled affinity agent that is not bound to the target analyte prior to the applying of the current.

In some embodiments, labeled affinity agent not bound to the target analyte is not removed prior to the applying of the current. In some embodiments, the current moves the labeled affinity agent not bound to the target analyte to a third sub-area of the compartment, wherein solution in proximity to the third sub-area has a pH at approximately the pI of the labeled affinity agent not bound to the target analyte, wherein the pH of the solution in proximity to the third sub-area is controlled by one or more proton/hydroxide injector(s); and detecting the presence or quantity of the labeled affinity agent not bound to the target analyte. In some embodiments, the method comprises further determining the ratio of affinity agent bound to the target analyte at the second sub-area of the compartment and the quantity of the labeled affinity agent not bound to the target analyte at the third sub-area of the compartment.

In some embodiments, the affinity agent continues to bind the target analyte when moved to the second sub-area and wherein the pH of the solution in proximity to the second sub-area is approximately the pI of the affinity agent bound to the target analyte.

In some embodiments, between the contacting and the applying, further comprising washing away affinity agent not bound to the target and then eluting the affinity agent bound to the target analyte such that the affinity agent no longer binds the target when moved to the second sub-area. In some embodiments, the pH of the solution in proximity to the second sub-area is approximately the pI of the affinity agent not bound to the target analyte. In some embodiments, the eluting comprises changing the pH of solution in proximity to the first sub-area. In some embodiments, the target analyte is moved to a third sub-area of the compartment, wherein solution in proximity to the third sub-area has a pH at approximately the pI of the unbound target analyte, wherein the pH is controlled by one or more proton/hydroxide injector(s). In some embodiments, the method further comprise collecting the target analyte.

In some embodiments, the localizing comprises binding the components of the sample to the first sub-area of a compartment. In some embodiments, the components are bound directly to the first sub-area. In some embodiments, the components are bound indirectly to the first sub-area via one or more binding components. In some embodiments, the components are bound indirectly to the first sub-area via an antibody linked to the first sub-area. In some embodiments, the components are biotinylated and are bound to the first sub-area by avidin or streptavidin linked to the first sub-area.

In some embodiments, the chamber is smaller at the second sub-area compared to the first sub-area.

In some embodiments, the localizing comprises applying a current, thereby moving charged components of the sample in proximity to the first sub-area.

In some embodiments, the contacting comprises contacting the localized components with a first and a second labeled affinity agent. In some embodiments, the first and second affinity agents have affinity for different target analytes and have different pIs. In some embodiments, the detecting comprises detecting the presence or quantity of the first and second labeled affinity agent at different sub-areas distinguished by different pH of the solution in proximity to the different sub-areas, thereby localizing the first and second affinity agents by the affinity agents' different pIs. In some embodiments, the first and second affinity agents have affinity for different target analytes and have different detectable labels. In some embodiments, the contacting comprises greater than two labeled affinity agents with affinity towards different target analytes and have different detectable labels.

In some embodiments, the method comprises:
providing a chamber comprising a first and a second electrode on two different sides of the chamber, wherein a first and second sub-area of the compartment are between the electrodes;
localizing components of a sample to the first sub-area of a compartment;
contacting the localized components with an affinity agent under conditions such that the affinity agent specifically binds the target analyte, if present, wherein the affinity agent is linked to an enzyme;
removing affinity agent that is not bound to the target analyte prior to the applying;
contacting a substrate to the enzyme, thereby generating a detectable processed substrate;
applying a current between the first and second electrode thereby moving the detectable processed substrate, if any, to the second sub-area of the compartment, wherein solution in proximity to the second sub-area has a pH at approximately the pI of the processed substrate, wherein the pH is controlled by one or more proton/hydroxide injector(s); and
detecting the presence or quantity of the detectable processed substrate at the second sub-area of the compartment, thereby detecting the presence or quantity of a target analyte in a sample.

In some embodiments, the localizing comprises binding the components directly to the first sub-area.

In some embodiments, the localizing comprises indirectly binding the components to the first sub-area via one or more binding components. In some embodiments, the localizing comprises indirectly binding the components to the first sub-area via an antibody linked to the first sub-area. In some embodiments, the components are biotinylated and the localizing comprises binding the biotinylated components to the first sub-area by avidin or streptavidin linked to the first sub-area.

In some embodiments, the chamber is smaller at the second sub-area compared to the first sub-area.

In some embodiments, the affinity agent is an antibody.

In some embodiments, a primary antibody binds the component and the enzyme is directly linked to the primary antibody.

In some embodiments, a primary antibody binds the component, a second antibody binds the primary antibody and the enzyme is linked to the secondary antibody.

In some embodiments, the enzyme is selected from the group consisting of horseradish peroxidase (HRP), alkaline phosphatase, and luciferase.

In some embodiments, the method comprises:
providing a chamber comprising a first and a second electrode on two different sides of the chamber, wherein:
a first and second sub-area of the compartment are between the electrodes;
an affinity agent specific for the target molecule is linked to the first sub-area, and;
the affinity agent is bound to a labeled competitor molecule, wherein the competitor competes with the target molecule for binding to the affinity agent;

contacting the affinity agent to a biological sample that may contain the target molecule under conditions such that the target molecule, if present in the biological sample, displaces the labeled target molecule or portion thereof from the affinity agent;

applying a current between the first and second electrode thereby moving the displaced labeled target molecule or portion thereof, if any, to a second sub-area of the compartment, wherein solution in proximity to the second sub-area has a pH at approximately the pI of the displaced labeled target molecule or portion thereof, wherein the pH is controlled by one or more proton/hydroxide injector(s); and detecting the presence or quantity of the displaced labeled target molecule or portion thereof at the second sub-area of the compartment, wherein the presence or quantity of the displaced molecule or portion thereof corresponds to the presence or quantity of the target analyte in the biological sample, thereby detecting the presence or quantity of a target analyte in a sample.

In some embodiments, the labeled competitor molecule is a labeled target molecule, or a labeled portion thereof.

In some embodiments, the affinity agent is an antibody.

In some embodiments, the chamber is smaller at the second sub-area compared to the first sub-area.

Also provided is an apparatus. In some embodiments, the apparatus comprises: a chamber comprising a first and a second electrode, wherein a first and second sub-area of the compartment are between the electrodes, wherein affinity agents (e.g., antibodies, avidin, streptavidin, etc.) are linked to the first sub-area; and the second sub-area comprises a fluorescence detector and one or more proton/hydroxide injector(s).

In some embodiments, the chamber further comprises a third sub-area between the electrodes and the third sub-area comprises one or more further proton/hydroxide injector(s). In some embodiments, the third sub-area further comprises a further fluoresce detector. In some embodiments, the affinity agents are antibodies.

Also provided is a system comprising an apparatus as described above or elsewhere herein (e.g., a chamber comprising a first and second electrode, one or more proton injector and/or hydroxide injector at a first sub-area of the chamber, optionally one or more affinity agents linked to a second sub-area of the chamber, optionally one or more outlet in the chamber, e.g., for sample addition or collection) and a power source (see, e.g., FIG. 3) for controlling the current or voltage between the first and second electrodes and/or the proton or hydroxide injectors. In some embodiments, the system further comprises a pump (e.g., for pumping fluid from or to the chamber and/or for pumping fluid through one or more injector). In some embodiments, the system further comprises a heating or cooling unit, e.g., for maintaining temperature of the fluid in the chamber and/or in one or more injectors. In some embodiments, the system comprises a stir bar or other mixing apparatus for mixing fluid in the chamber. In some embodiments, the system, comprises a pH meter and/or ionic strength meter.

In some aspects, the present invention provides a method for selectively positioning a target analyte in a solution containing a mixture of analytes, the target analyte having a pH dependent charge, the method comprising: providing into a chamber a sample comprising the solution containing the mixture of analytes, including the target analyte, wherein the chamber comprises a first and a second electrode and at least two proton/hydroxyl injectors positioned between the electrodes; generating a first pH step with one of the at least two proton/hydroxyl injectors, thereby generating a first sub-area having the first pH step, and applying an electric field across the electrodes, thereby moving a portion of the mixture of analytes to the first sub-area in the chamber based on the pH dependent charge of the target analyte, wherein the portion of the mixture of analytes comprises analytes having a range of isoelectric points from of about pH 3 or more to pH of about 10 or less; and generating a second pH step with the second proton/hydroxyl injector, thereby generating a second sub-area having the second pH step, wherein the second pH step is narrower than the first pH step and encompasses a pH range that includes the pI of the target analyte, thereby selectively positioning the target analyte in a sub-area near the second proton/hydroxyl injector of the chamber.

In some embodiments, the method comprises electronically changing the first or second pH step with the first or second proton/hydroxyl injector respectively, thereby re-positioning the target analyte in the chamber. In some embodiments, the selectively positioning the target analyte in the chamber comprises precipitating the target analyte in the chamber at a position corresponding to the isoelectric point of the target analyte. In some embodiments, the method further comprises positioning an affinity agent in the chamber to contact, and bind to, the target analyte. In some cases, the affinity agent has a different isoelectric point than the target analyte and is positioned in the same sub-area as the target analyte by the pH step generated by the second proton/hydroxyl injector and the applied electric field. In some cases, the method further comprises washing away unbound affinity agent after the step of binding the target analyte to the affinity agent. In some cases, the method further comprises changing the second pH step to thereby elute the affinity agent or target analyte. In some cases, the method further comprises detecting the eluted affinity agent or target analyte.

In some embodiments, wherein the first and the second pH steps are controlled by a pre-programmed set of instructions. In some cases, the pre-programmed set of instructions are provided on a computer readable medium.

In some aspects, the present invention provides a method of purifying a target analyte form a mixture of analytes in a sample by molecular weight and pH dependent charge profile in an apparatus, wherein the purifying is performed along a single separation axis in a separation chamber of the apparatus, the method comprising: a) introducing into the separation chamber of the apparatus the sample; b) generating a substantially uniform pH in the separation chamber using one or more proton/hydroxyl injectors; c) applying an electric field in the chamber, wherein the electric field comprises a voltage difference along the single separation axis of the chamber and thereby causes the mixture of analytes to separate according to molecular weight along the single separation axis of the chamber; and d) after separating by molecular weight, generating a pH gradient using the one or more proton hydroxyl injectors, wherein the pH gradient is along the single separation axis, thereby positioning the analytes according to their isoelectric points along the single separation axis.

In some embodiments, the chamber comprises a separating medium, the separating medium comprising a gel. In some cases, the gel is a polyacrylamide gel. In some embodiments, the electric field and the pH, or pH gradient of the chamber are controlled by a pre-programmed set of instructions. In some cases, the pre-programmed set of instructions are provided on a computer readable medium.

In some aspects, the present invention provides a method of separating a target analyte in a sample from one or more other analytes in the sample, the method comprising: providing into a chamber the sample, including the target analyte, wherein the chamber comprises a first and a second electrode and a proton/hydroxyl injector positioned between the electrodes; generating a first pH gradient in the chamber and applying an electric field across the electrodes, thereby moving and separating the analytes, including the target analyte, according to charge and, optionally, molecular weight; and transiently altering the pH gradient to selectively elute the target analyte from the chamber.

In some embodiments, the chamber comprises a separating medium, the separating medium comprising a gel. In some cases, the gel is a polyacrylamide gel. In some embodiments, the electric field and the pH, or pH gradient of the chamber are controlled by a pre-programmed set of instructions. In some cases, the pre-programmed set of instructions are provided on a computer readable medium.

BRIEF DESCRIPTION OF THE DRAWINGS

FIGS. 5A-C illustrate generation of a pH step gradient and isolation of target molecules with the gradient. In the figure, a bipolar membrane (2) generates a large pH differential, thereby focusing unwanted components (1) of the sample away from the target analyte. A second bipolar membrane (4) generates a small pH differential centered at the pI for the target analyte (3). The target analyte (3) can optionally be collected in a channel (5) in the chamber.

FIG. 9 illustrates embodiments in which a chamber or channel as described herein is adapted for delivery of analytes to a mass spectrometer (FIG. 9A) or to a light source (FIG. 9B).

FIGS. 10A-C illustrate digital pH analytical separation of a target molecule.

FIG. 11 shows the same channel running top to bottom in the figure at four time points (a), (b), (c), and (d). The numbers to the left of the channel indicate pH, with a proton or hydroxide injector shown across the channel at each position at which pH is indicated. Sample components (111, 112, 113, 114, 115) are shown moving electrophoretically over time ((a), (b), (c), and (d))

FIG. 22 illustrates a configuration combining aspects shown in FIGS. 20 and 21. Thus, affinity agents are used, some of which can be distinguishable by pI with others distinguishable by the signal of the label. In this figure, affinity agents are represented by numbers (2*, 2+, 4*, 4+, 7) with asterisks (*) and plus signs (+) representing different affinity agents that have the same pI but different detectable labels. The numbers are intended to indicate exemplary pIs, i.e., affinity agents 2* and 2+ both have a pI around 2, affinity agents 4* and 4+ have a pI around 4, and affinity agent 7 has a pI around 7. Once the affinity agents are eluted from their respective targets (bottom part of figure), the affinity agents are moved by an electrical field to separate detection areas having different localized pHs (~2, ~4, and ~7). In situations where more than one affinity agent has the same approximate pI (e.g., 2* and 2+), they are distinguished by their signals. Thus for example, to distinguish 2* and 2+, the two affinity agents must have distinguishable signals. However, there is no need for 2* and 7 to have different signals, because those affinity agents are localized to different detectors.

FIG. 23 schematically illustrates an apparatus configuration and its use to detect multiple different target molecules similar to FIG. 22. The bottom portion of the figure illustrates how that top portion can be configured in replicate channels, thereby allowing for multiple samples to be analyzed in parallel for multiple targets.

FIG. 25 is similar to FIG. 24, but instead of using a capture affinity agent, the target molecule(s) (and optionally other sample components) are linked directly or indirectly to the first sub-area of the chamber. The remaining aspects of the method are similar to those described for FIG. 24. This aspect can be performed in multiplex if desired by using affinity agents with different target specificity linked to different enzymes such that different detectable processed substrates can be distinguished (e.g., by wavelength, pI, or other criteria).

In FIG. 26A, a target analyte (shown as dots) is positioned in the chamber in proximity to the solid support using pI focusing as described herein, thereby binding the target analyte to the affinity ligand. FIG. 26B illustrates a subsequent stage in which the pH gradient is removed. FIG. 26C illustrates an embodiment in which the target analyte is subsequently eluted from the affinity agent, e.g., for collection as a purified product. Elution can occur in any way desired. In some embodiments, the solution is changed to elute the analyte. In some embodiments, the proton/hydroxide ion injector is used to change the pH in proximity to the affinity ligands to a pH resulting in elution.

DEFINITIONS

Figure 1A:
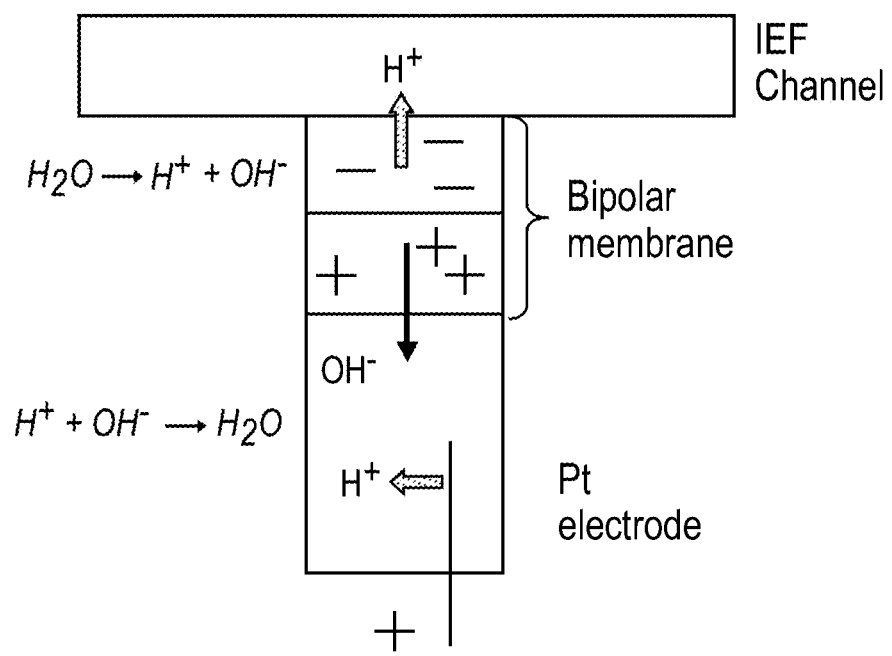
FIGS. 1A and 1B illustrate a proton and hydroxide injector, respectively, comprising a small compartment adjacent to the channel/chamber, with a Pt electrode dipped inside it, and a bipolar membrane separating the compartment from the channel/chamber.

An "affinity agent" refers to a molecule that specifically binds a target molecule. Exemplary affinity agents include, e.g., an antibody, antibody fragment, or aptamer. IN situations in which a target molecule is nucleic acid, the affinity agent can be, for example, a complementary nucleic acid.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The labels may be incorporated into, e.g., antibodies and/or other proteins at any position. Any method known in the art for conjugating the antibody to the label may be employed, e.g., using methods described in Hermanson, *Bioconjugate Techniques* 1996, Academic Press, Inc., San Diego. Alternatively, methods using high affinity interactions may achieve the same results where one of a pair of binding partners binds to the other, e.g., biotin, streptavidin. Thus, for example, an affinity agent can be directly labeled with isotopes, chromophores, lumiphores, chromogens, or indirectly labeled such as with biotin to which a streptavidin complex (optionally including, e.g., a fluorescent, radioactive, or other moiety that can be directly detected) may later bind. Thus, a biotinylated antibody is considered a "labeled antibody" as used herein.

The phrase "specifically (or selectively) binds" or "specifically (or selectively) immunoreactive with" or "having binding specificity for", when referring to an affinity agent and target molecule, refers to a binding reaction between the affinity agent and target molecule which is determinative of the presence of the target molecule in the presence of a heterogeneous population of proteins and/or other biologics. Thus, for example, under immunoassay conditions, antibodies bind to a particular protein and do not bind in a significant amount to other proteins present in the sample. Specific binding to an antibody under such conditions may require an antibody that is selected for its specificity for a particular protein. For example, antibodies raised against a protein can be selected to obtain antibodies specifically immunoreactive with that protein and not with other proteins. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See, Harlow and Lane *Antibodies, A Laboratory Manual*, Cold Spring Harbor Publications, NY (1988) for a description of immunoassay formats and conditions that can be used to determine specific immunoreactivity. Typically, a specific or selective reaction will be at least twice the background signal or noise and more typically more than 10 to 100 times background.

The term sample relates to any type of sample, including but not limited to a biological sample. The term "biological sample" encompasses a variety of sample types obtained from an organism. The term encompasses bodily fluids such as blood, saliva, serum, plasma, urine and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, sedimentation, or enrichment for certain components. The term encompasses a clinical sample, and also includes cells in cell culture, cell supernatants, cell lysates, serum, plasma, other biological fluids, and tissue samples. The term is not limited to human-derived, or medical-related samples, and thus can include, e.g., plant-based, prokaryotic-based, or other samples of biological origin.

The term "antibody" refers to a polypeptide comprising a framework region (e.g., from an immunoglobulin gene), or fragments thereof, that specifically bind and recognize an antigen or desired target. Typically, the "variable region" contains the antigen-binding region of the antibody (or its functional equivalent) and controls specificity and affinity of binding. See Paul, *Fundamental Immunology* (2003).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

An "isotype" is a class of antibodies defined by the heavy chain constant region. Immunoglobulin genes include the kappa, lambda, alpha, gamma, delta, epsilon, and mu constant region genes. Light chains are classified as either kappa or lambda. Heavy chains are classified as gamma, mu, alpha, delta, or epsilon, which in turn define the isotype classes, IgG, IgM, IgA, IgD and IgE, respectively.

Antibodies can exist as intact immunoglobulins or as any of a number of well-characterized fragments that include specific antigen-binding activity. Such fragments can be produced by digestion with various peptidases. Pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

"Target analyte" or "target molecule" can include a biomolecule, or molecule of biological origin. Target molecules include, but are not limited to, proteins, polynucleotides, metabolites, viruses, and virus-like particles and cells. Examples of proteins include but are not limited to antibodies, enzymes, growth regulators, clotting factors, and phosphoproteins. Examples of polynucleotides include DNA and RNA. Examples of viruses include enveloped and non-enveloped viruses.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide nucleic acids (PNAs).

The terms "polypeptide," "peptide," and "protein" are used interchangeably herein to refer to a polymer of amino acid residues. Peptides can be of any length of two or more amino acids, e.g., 6-100, 80-50, 10-40 amino acids, etc.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded.

DETAILED DESCRIPTION OF THE INVENTION

I. Introduction

As described in more detail herein, methods and apparatuses are provided that allow for detection, purification, and/or isolation of target molecules (e.g., proteins, peptides, nucleic acids, etc.) from samples in a chamber in an apparatus optionally using 1) electrical fields to move the targets combined with 2) electronic control of pH of solution in sub-areas of the chamber using proton or hydroxide injectors. The methods take advantage of the pH-dependence of charge of targets, for example allowing for localization of charged targets to a particular sub-area by setting the pH of solution in proximity to the sub-area to a pH at or close to the pI of the target of interest. At a target's pI, the target becomes uncharged and therefore does not move further in an electric field. A number of embodiments using this aspect are described below.

Figure 2:
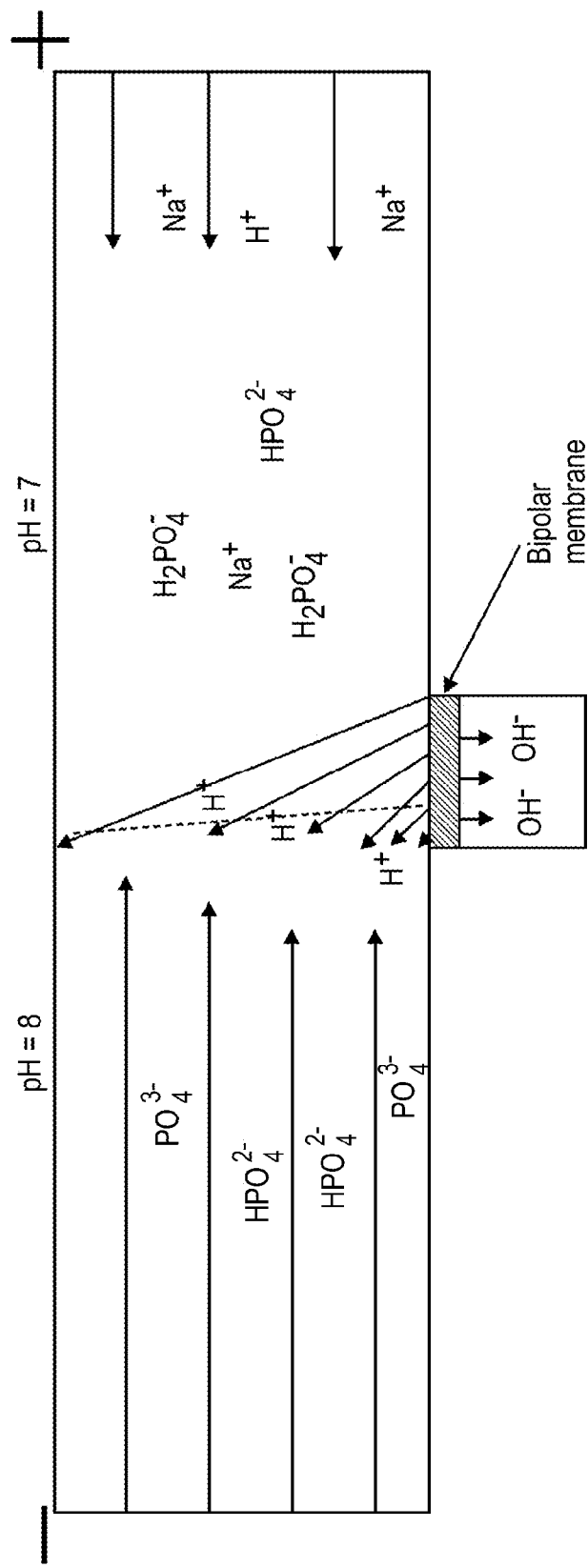
FIG. 2 illustrates possible electrolytes and their interaction with a proton/hydroxyl injector.

The apparatus can have a variety of configurations. In some aspects, the apparatus comprises at least one chamber having a first and second electrode, which allow for moving a charged target in an electric field. The chamber can comprise one or more (e.g., 1, 2, 3, 4, 5, or more) proton or hydroxide injector separated from the chamber by a bipolar membrane, wherein the injector comprises an electrode, thereby allowing for electro-hydrolysis of water molecules. See, e.g., FIG. 2. The terms "chamber" and "channel" are used synonymously. The terms encompass containers that are considerably (e.g., 10×, 100×, 1000×) longer than wide, which allow for multiple injectors along the long axis of the chamber.

In some aspects, the apparatus can contain one or more chambers, wherein at least one of the one or more chambers has at least two distinct sub-areas in the chamber. A "sub-area" refers to a region of the container at which molecules can be localized and in some aspects detected. Thus, for sub-areas at which detection is to occur, the sub-area can be sufficiently narrow or small to allow accurate determination of the quantity of molecules localized to that sub-area. For sub-area(s) in which detection does not occur (e.g., where a sample is initially positioned in the chamber), the sub-area(s) can be larger. Generally, the chamber will contain an aqueous solution compatible with the sample and affinity agents used. Different sub-areas do not overlap. In some embodiments, each sub-area represents less than about 50%, 40%, 30%, 20%, 10%, 5%, or 1% of the area of the chamber.

Without intending to limit the scope of the invention, it is noted that chambers of the following dimensions have been constructed:

| Channel L/H/W in mm | Slit L/H/W In mm | Material | Channel volume (Vc; in µl) | Slit volume in µl (Vs; in µl) |
|---|---|---|---|---|
| 90 × 0.3 × 3 | 3 × 0.5 × 0.3 | Glass/PMMA | 81 | 0.45 |
| 36 × 0.2 × 1 | 1 × 0.2 × 0.2 | COC | 7.2 | 0.04 |
| 221 × 0.25 × 1 | 1 × 0.25 × 0.2 | PMMA | 55 | 0.05 |
| 36 × 0.15 × .5 | .5 × 0.1 × 0.1 | PMMA | 2.7 | 0.005 |
| 33.6 × 0.25 × 1 | 1 × 0.25 × 0.23 | PMMA | 8.4 | 0.0575 |
| 221 × 0.25 × 1 | 1 × 0.25 × 0.2 | PMMA | 55 | 0.05 |

"Slits" refer to the size of the hole in the chamber through which the proton or hydroxide injector is connected to the chamber. A bipolar membrane at the slit divides the chamber from the injector.

The orientation of the electrodes (i.e., which is a cathode and which an anode) will depend on the charge of the molecules to be moved in the solution and the direction the molecules are to be moved. For example, a positively-charged molecule moves towards a cathode and a negatively-charged molecule moves towards an anode when an electrical voltage difference is present through the solution in the chamber between the cathode to the anode.

Generally, the electrodes should be oriented so that they are as close to each other as possible, i.e., directly across from each other. While other configurations are contemplated and possible, voltage and resistance increases as a function of distance.

Electrodes in the chamber can in some circumstances interfere and/or bind target molecules (e.g., protein) in the chamber. Thus, in some embodiments, the electrodes are separated from the chamber by a membrane or gel, thereby preventing target molecules from binding the electrodes.

The size and shape of the chamber can vary. While the chamber is depicted as a tube or channel (i.e., longer between the electrodes than across other axis), other configurations are also possible.

A proton or hydroxide "injector" refers to one or more compartments, separated from a sub-chamber or other vessel (e.g., such as a reservoir), by a hole or "slit" and divided by a bipolar membrane(s), wherein the compartment(s) contain an electrode(s). Depending on the orientation of the electric field (e.g., orientation of the anode and cathode) in the compartment(s), the compartment(s) can be designed to inject protons or hydroxide ions through the bipolar membrane(s) and into the adjacent chamber.

By controlling the current and configuration, one can thereby control the pH of solution in the chamber in proximity to the proton or hydroxide injector. Generally, it can be desirable to increase the surface area of the bipolar membrane as this allows for decreased electrical resistance.

The membrane(s) "divides" the compartments from the chamber by forming a barrier that separates solution in a compartment from the chamber, e.g., at least to the level of solution in the chamber. For example, in embodiments in which the chamber is open at the top (or alternatively, has a top cover that can be removed), the membrane(s) can be designed to completely divide a compartment from the chamber at least up to the level of solution in the chamber and/or compartment, or to a level designated as a maximum for solution loading. As desired, the membranes can be designed to be higher than the solution level so as to avoid accidental transfer (e.g., splashing) from one portion to another. If desired, the membranes can be "framed" by a solid material (e.g., plastic) or otherwise anchored between the chamber and the compartment.

The electrodes can be formed from any conducting or semi-conducting substance. For example, in some embodiments, one or more electrode comprises a metal. In some embodiments, the metal is zinc, copper, or platinum. For example, the electrodes can be platinum or can be platinum-plated. Generally, maximal surface area for electrodes is desirable. A flattened electrode, for example, provides more surface area than a wire.

International Patent Application Publication No. WO2009/027970 describes methods and devices (i.e., proton or hydroxide injectors) useful in producing local concentrations of protons or hydroxide ions, proton or hydroxide concentration gradients, and desired proton or hydroxide concentration topographies in an environment, such as an electrolyte solution, a gel, and the like. International Patent Application Publication No. WO2011/021195 and WO2011/021196 describe methods and devices for isoelectric focusing proton/hydroxide injectors and also describes display of data.

Figure 1B:
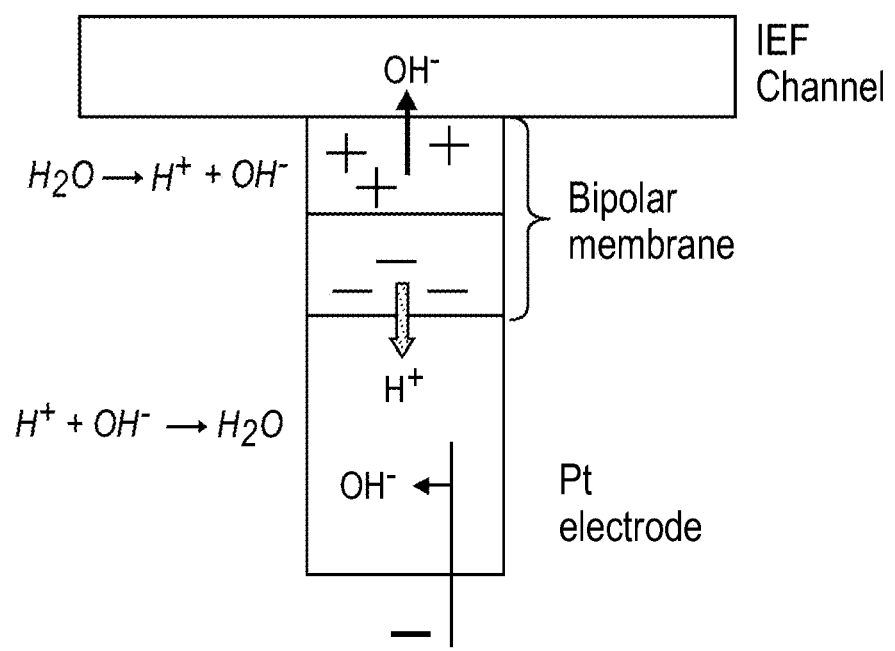

Proton/hydroxide injector technology can be used to affect the pH of the solution in a chamber, or at least the solution in the chamber in proximity to the injector. Briefly, in some embodiments, the proton/hydroxide injector comprises a compartment adjacent to the apparatus chamber, with an electrode inside the compartment, and a bipolar membrane separating the compartment from the channel. See, e.g., FIGS. 1A-1B. A bipolar membrane is an ion-exchange membrane having a structure in which a cation-exchange membrane and an anion-exchange membrane are joined together, and allows for water molecules to be split into protons and hydroxide ions. Voltage applied between the compartment and the channel divided by the bipolar membrane leads to water splitting and injection of protons or hydroxide ions into the channel. Some advantages of this technology can include, for example, bubble-free water hydrolysis and injection of generated ions directly to the channel, allowing short response time (e.g., if desired, below 1 minute).

By applying the appropriate voltage to the electrodes in the chamber an electric field across the solution in the chamber is generated and charged molecules move accordingly. In some embodiments, the charged molecules can be added in proximity to the anode or cathode in the chamber (in which the pH is controlled at least in part by a proton injector or a hydroxide injector), and subsequently the voltage is applied, thereby delivering the charged molecule to a desired position in the chamber at a time determined by the user.

The direction of movement of the molecule will depend on the charge of the molecule and the polarity of the applied voltage.

Figure 3:
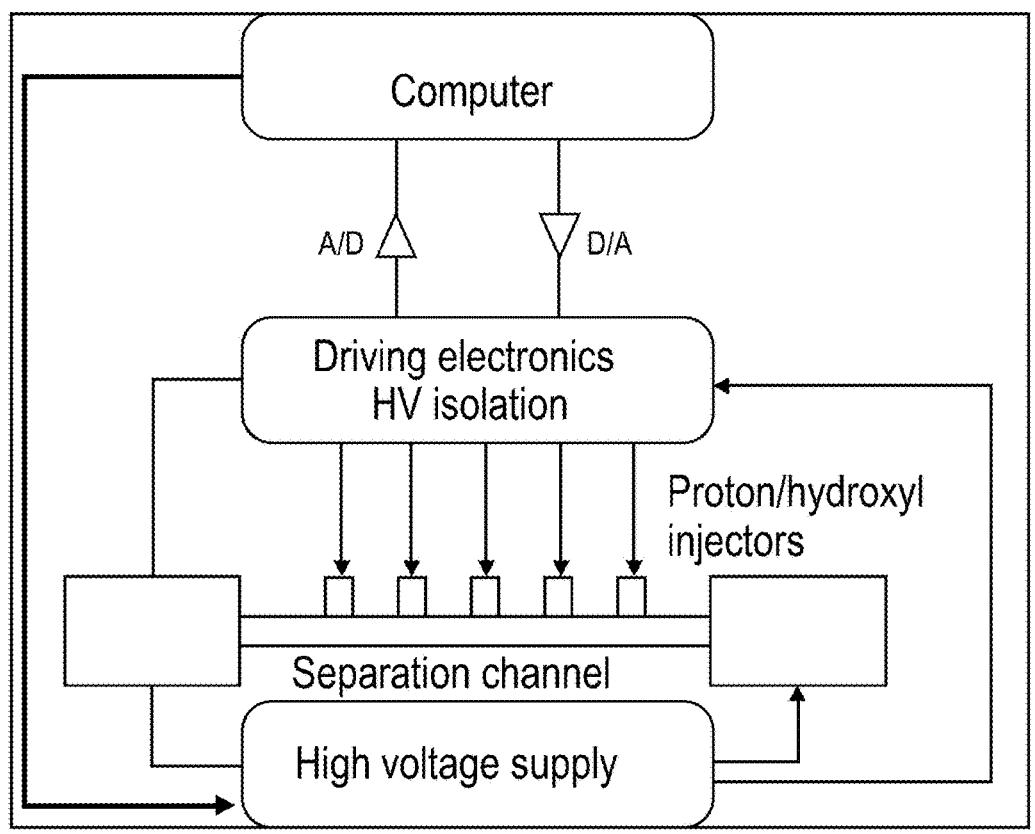
FIG. 3 illustrates an embodiment for a system controlling a proton/hydroxyl injector device.
Figure 4:
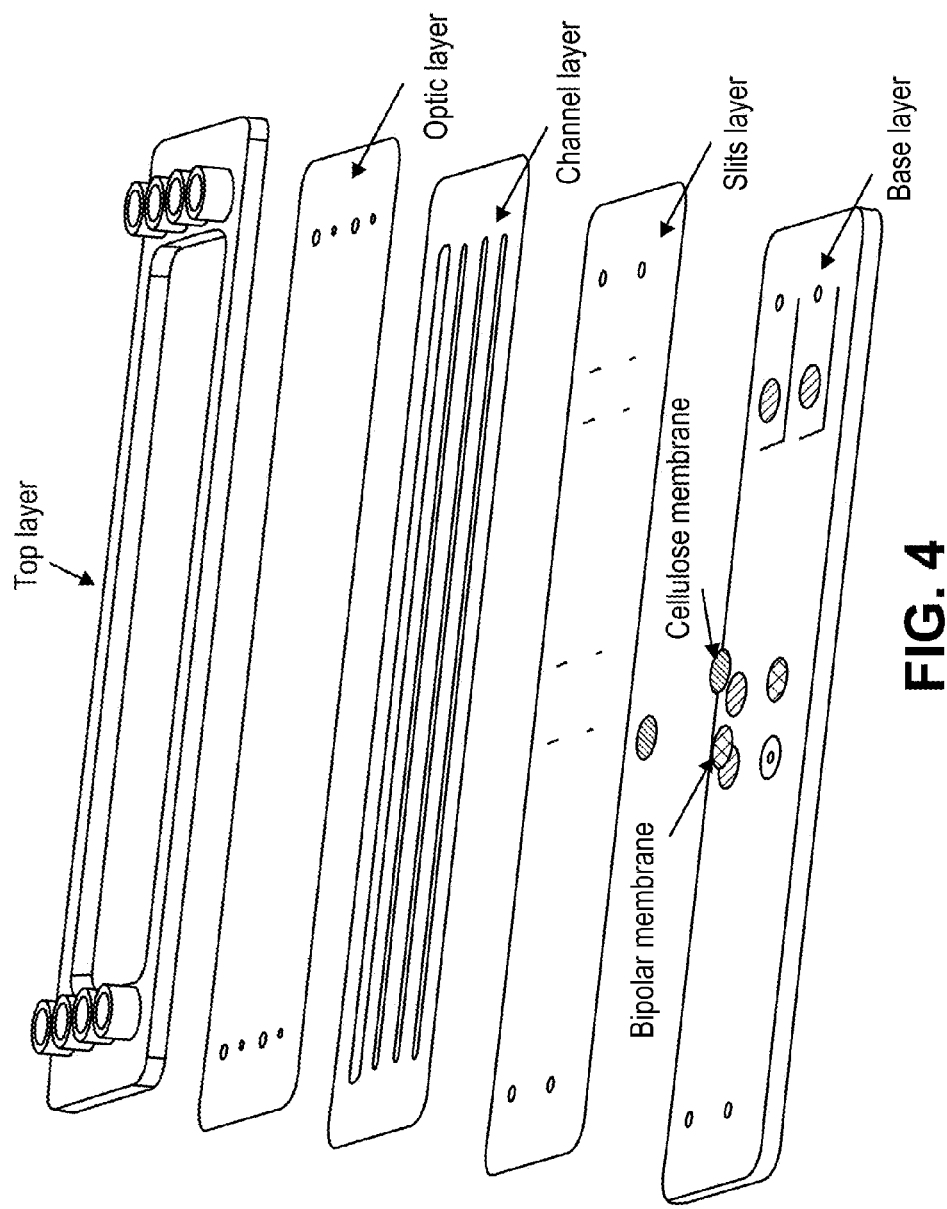
FIG. 4 illustrates an embodiment of an integrated disposable channel for use in a proton/hydroxyl injector device. Openings (e.g., slits) for fluid contact to proton/hydroxide injector compartments can be arranged as desired. For example, in some embodiments, slits in the chamber are 1-1000 microns, and in some embodiments, about 100 micron. The number and size of slits can be designed to generate step-wise pH gradients as desired. Cellulose, or other hydrophilic, membranes, for example, as shown in FIG. 4 are optional, and function to cover unused slits and/or can optionally cover bipolar membranes to the extent sample components have affinity to the bipolar membrane. In some embodiments, instead of hydrophilic membranes, hydrophilic coatings may be used to cover the bipolar membranes and prevent binding of the sample components to it. Further openings (e.g., slits) can be used to extract and inject samples to the channel.

Systems incorporating the apparatus are provided. Systems can include, for example, a power supply and power regulator to control current and/or voltage to electrodes in the chamber and/or injectors. See, e.g., FIG. 3. Pumps for regulating flow of liquids, a mechanism for stirring or mixing solution in the chamber, and heating or cooling units can be included. In some embodiments, the system includes a pH and/or conductivity probe in the chamber. Generally, it can be desirable to place the probe at a distance from the electric field lines between electrodes to improve readings.

II. Methods and Devices
Methods and Devices for Detecting and Collection Analytes Fractionated Based on pI Dynamically adjustable pH 'step/s' spanning the pH range of ~2-12 (can be further extended or contracted as needed) can be generated within a chamber filled with suitable buffers using proton and/or hydroxide injectors as described herein. Use of proton or hydroxide injectors to control pH as described herein can be designed such that target analytes reach their pI in only minutes, for example, in some embodiments, less than, e.g., 10, 20, or 30 minutes.

An example of such a gradient is displayed in FIG. 5A. FIG. 5A illustrates an embodiment in which a relatively large difference in pH between two regions of the chamber (left side) is used to capture a majority of analytes having a pI within the pH range. To the right a smaller pH range (designed specifically to span a particular target analyte pI) is shown, thereby isolating the target analyte without significant amounts of other components of the sample. Complex mixtures of suitably buffered analytes (including but not limited to proteins and/or peptides) will be submitted to an electric field within the chamber so as to 'capture' proteins (or peptides) at their respective isoelectric points (pI) in either a single pH step (see FIG. 5B) or multiple pH 'step/s' spanning the desired pH range. Subsequently, when collection of the purified target is desired, in some embodiments, ampholyte-free, charged species can be released from the chamber towards a harvesting chamber for collection and downstream analysis. See, e.g. FIG. 5C. Movement of the purified target from the chamber into collection can be achieved, for example, by physical pumping, electro osmotic pumping, or electronic adjustment of $H^+/OH^-$ generation at (each) gradient 'step'. See, e.g. FIG. 5C. This approach can allow for optimized fractionation of various protein/peptide samples (via adjusting protein/peptide capture and release in a sample-dependent manner) or other types of samples (e.g., nucleic acids or other) without contamination by chemical ampholytes that occur in standard isoelectric focusing.

Figure 6:
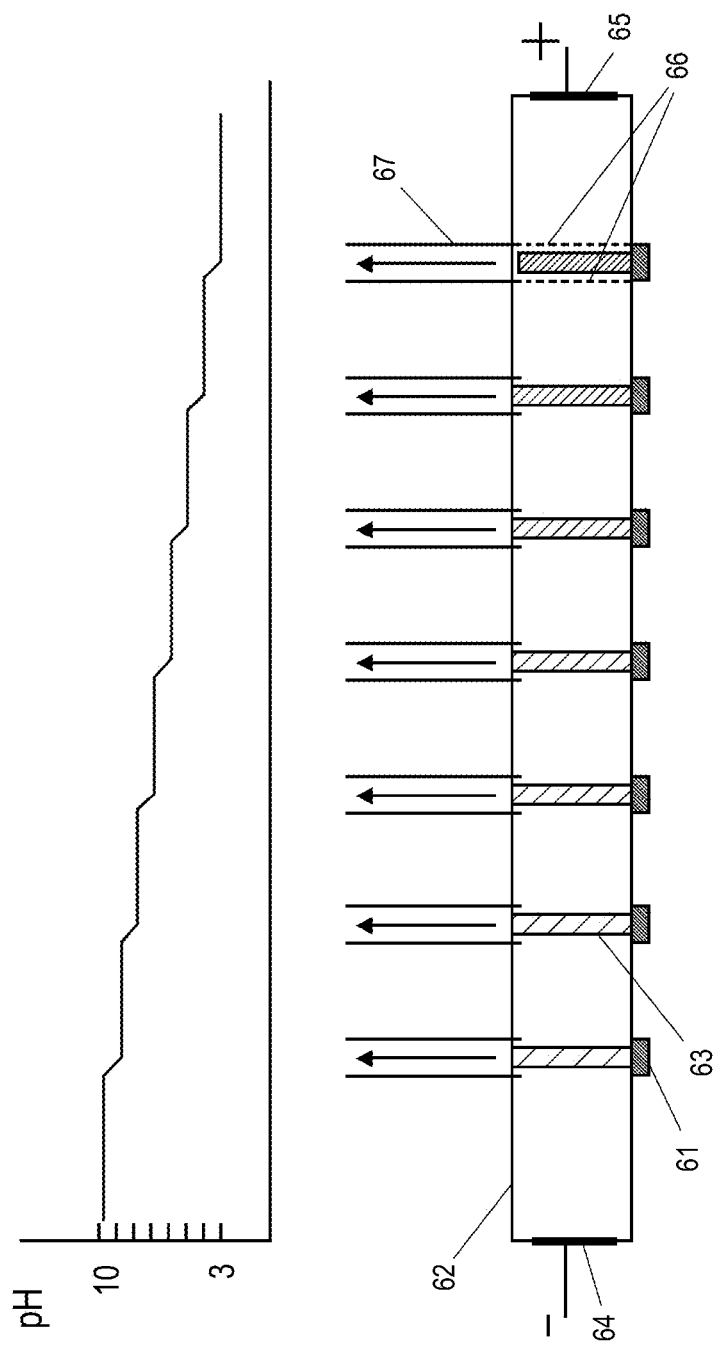
FIG. 6 illustrates generation of a pH step gradient and isolation of multiple target molecules with the gradient. This embodiment can be used for subsequent application to electrophoresis or other applications.

As shown in FIG. 6, in some embodiments, multiple bipolar membranes (61) are placed directly under the slits in a channel (62), also referred to herein as a "chamber." The separation channel can be filled with a suitable buffer. Either protons or hydroxide ions are injected by each bipolar membrane to create a step gradient as shown on the pH graph (FIG. 6). The peptides or proteins (63) focus in the steps corresponding to their pI by applying an orthogonal electrical field through electrodes (64) and (65). Optional permeable membranes or screens (66) can be used to create chambers where the proteins or peptides are focused. After the focusing is completed the target analytes (e.g., peptides or proteins) are harvested through harvesting ports (67) in fluid communication with the channel, allowing for collection of target analytes having a specific pI. Collection ports can be of a diameter useful for collection. In some embodiments, the collection ports are 100 microns or less in diameter, e.g., 1-100 microns in diameter.

In some embodiments, the technology is used to address two issues: the cleanup (e.g., removal or reduction of one or more contaminant) and/or concentration of a protein of interest.

Figure 7:
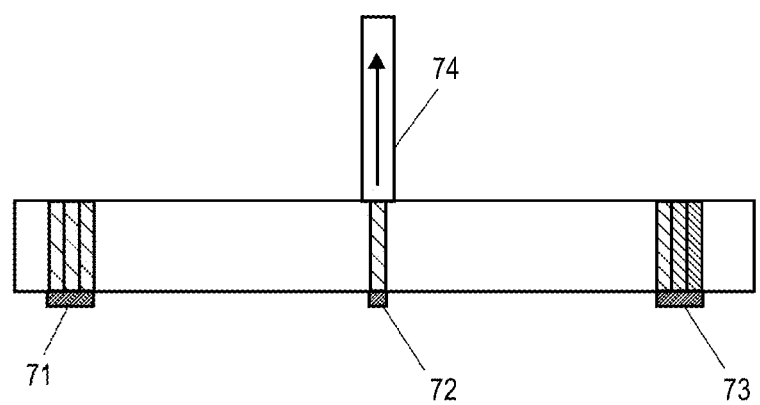
FIG. 7 illustrates generation of a pH step gradient and isolation of target molecules with the gradient. This can be used, for example, for protein clean-up, capture and direct injection into mass spectrometer (MS), or other detection methods.
Figure 8A:
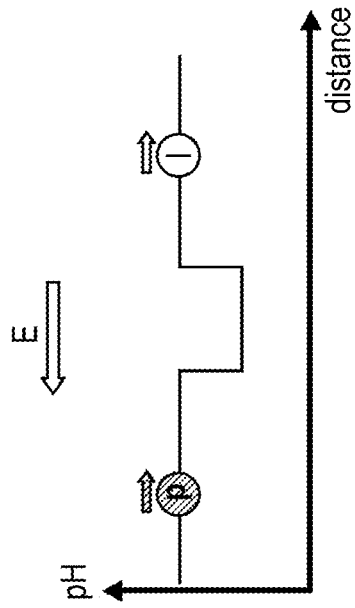
FIGS. 8A-D illustrate isolation and collection of a target molecule using pH gradients.
Figure 8C:
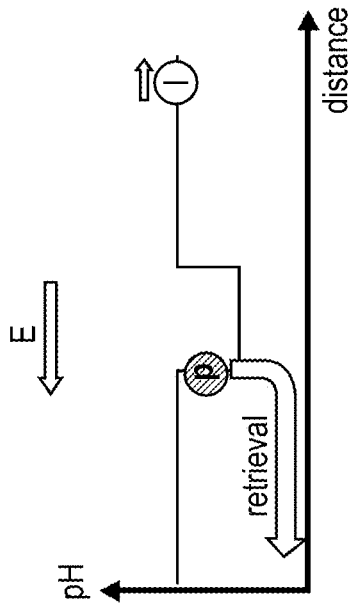
Figure 8B:
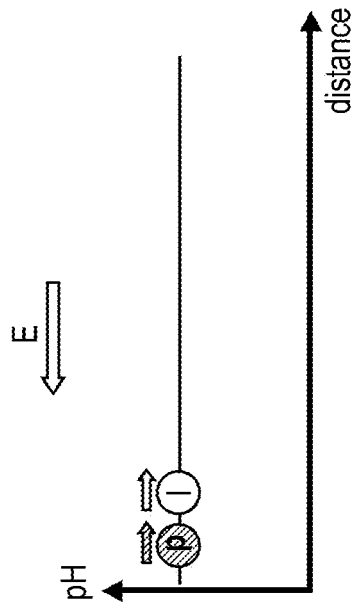
Figure 8D:
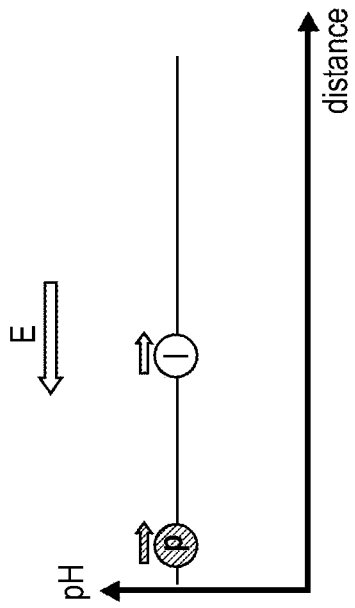

In some embodiments, e.g., as shown in FIG. 7, the protein sample is separated into at least three fractions:
The proteins with pI higher than the pI of the target protein (or other target analyte) are isoelectrically focused in the region of bipolar membrane (71) where a pH step encompassing pH higher than the pI of the antigen is created.

The protein of interest is focused in the region of bipolar membrane (72) by creating a narrow pH range step encompassing the pI of the protein of interest.

The proteins with pI lower than the pI of the target protein are isoelectrically focused in the region of bipolar membrane (73) where pH step with range below the pI of the protein of interest is created.

In this way, the protein of interest can be separated (purified) from the other proteins and other contaminants and concentrated in the area close to the harvesting channel. Subsequently the protein of interest can be harvested via a harvesting port or through harvesting channel (74). In some embodiments, the harvesting can be accomplished using, for example, liquid flow or electrophoresis.

FIGS. 8A-D illustrate embodiments of protein cleanup and capture. In these embodiments, electronically generating a pH step gradient is exploited for protein purification. Generally, purifying specific macromolecules from a mixture is most efficiently achieved when the process of purification is based on some known property of the macromolecule (like mass, mobility, affinity). Such is the case in affinity columns, electrophoresis, ion exchanger column and many other purification techniques. In the embodiments described herein, the relevant properties of the molecule include their isoelectric point (pI) and mobility under electric field.

In some embodiments of the purification apparatus, a pH step is created in a channel to which the protein of interest (POI) is inserted together with some impurities, e.g., other components of the sample. The pH step is designed according to the pI of the POI and the surrounding impurities so that the pI of the former will fall in the range of the step while the pI of the latter will not. In this way the protein will focus in a sharp band as shown in FIG. 7 while the latter will continue migrating towards the end of the channel. This procedure is very simple in the case were the impurities and POI have distant isoelectric points or in the case were the impurities lack a pI altogether. In the case were the pI's are close, the difference in mobility can be used as one of several criteria for separation.

An example is given in FIG. 8. The POI and some impurities, marked "P" and "I" respectively, migrate under constant pH conditions (FIG. 8A). In case the impurities are faster than the protein (most likely this is the case when the impurities are small molecules or short peptides) a gap develops between the two (FIG. 8B). When this gap is large enough, the constant pH profile is changed to one with an acidic depression, as in FIG. 8C, which causes the protein to focus in a pH step, while the impurities continue to migrate towards the end of the channel (FIG. 8D). In some embodiments, in addition to the purification power, the apparatus will have a retrieval system, e.g., for further analysis of the POI.

FIG. 9 shows aspects of the technology described herein in which a simple or complex mixture (sample) of proteins or peptides is submitted to isoelectric focusing via pH step gradients and one or more target analyte in the sample is detected. As shown in FIG. 9A, in some embodiments, the end of a chamber in which the pH gradients are set can be fitted with a nozzle or other device for delivering isoelectrically purified portions directly to a mass spectrometer (MS). This allows for delivery of a simplified sample (starting from the original mixture of higher complexity) to the MS device and is free from ampholytes (as would occur in other types of isoelectric focusing and which interfere with MS). Alternatively, as shown in FIG. 9B, isoelectrically focused analytes can be detected with other detectors, including but not limited to, an in-line fluorescent detector (for detecting fluorescently-labeled analytes), a light source, a UV light source, etc.

In some embodiments, one or more target molecules can be focused based on pI using one or more proton or hydroxide injectors and subsequently submitted to electrophoresis. The pI fractions can be precisely positioned where desired (for example on the top of the second dimension channel) when using a proton/hydroxide injector. In contrast, in isoelectrical focusing (IEF) steady state is achieved and therefore, the bands are not moving through the detector. This means either the detector needs to move along the capillary or the whole capillary needs to be imaged. With electronic control of pH as described herein, the target bands can be delivered to the detector, thereby simplifying design.

In some embodiments, the method of proton injector or hydroxide injector-mediated pH focusing can be used for analytical purposes. In conventional IEF gels or strips, the sample is analyzed in a spatial pattern where proteins focus in their pI based on the location of the pH on the gel. In contrast, in embodiments employing a proton injector or hydroxide injector, a dynamic map of target (e.g., target protein) quantity v/s pH value can be created. An example is illustrated in FIGS. 10A-C. The target-containing sample (101) is initially captured at the broad pH step created by a proton injector or hydroxide injector separated from the channel by a bipolar membrane (102). Then the pH in the lower (or upper) range of the step is changed to allow the sample components (103) with pI above the pHl (the low end of the pH in the step) and below pHh (the high end of the pH in the step) to start migrating to the second proton injector or hydroxide injector separated from the channel by a second bipolar membrane (104), e.g., by diffusion or using electrodes in the channel to electrophorese the charged components further down the channel. By increasing the pHl and pHh pH values the sample components can be moved from membrane 102 to membrane 104. By keeping the ΔpH small, the resolution of the methodology can be very high. The target molecules can be detected by any method available, including but not limited to, by using absorbance, fluorescence (conveyed by a dye that attaches to the proteins covalently or non-covalently). As illustrated in FIG. 10C, in some embodiments, the proteins or other target molecules are detected by using emitting diode (105) and light capturing diode (106) to detect the light from the excited dye. This method can be used, for example, to determine the relationship between the pI and amount for a complex sample or for a purified protein (for example when looking at charge isoforms).

Figure 11:
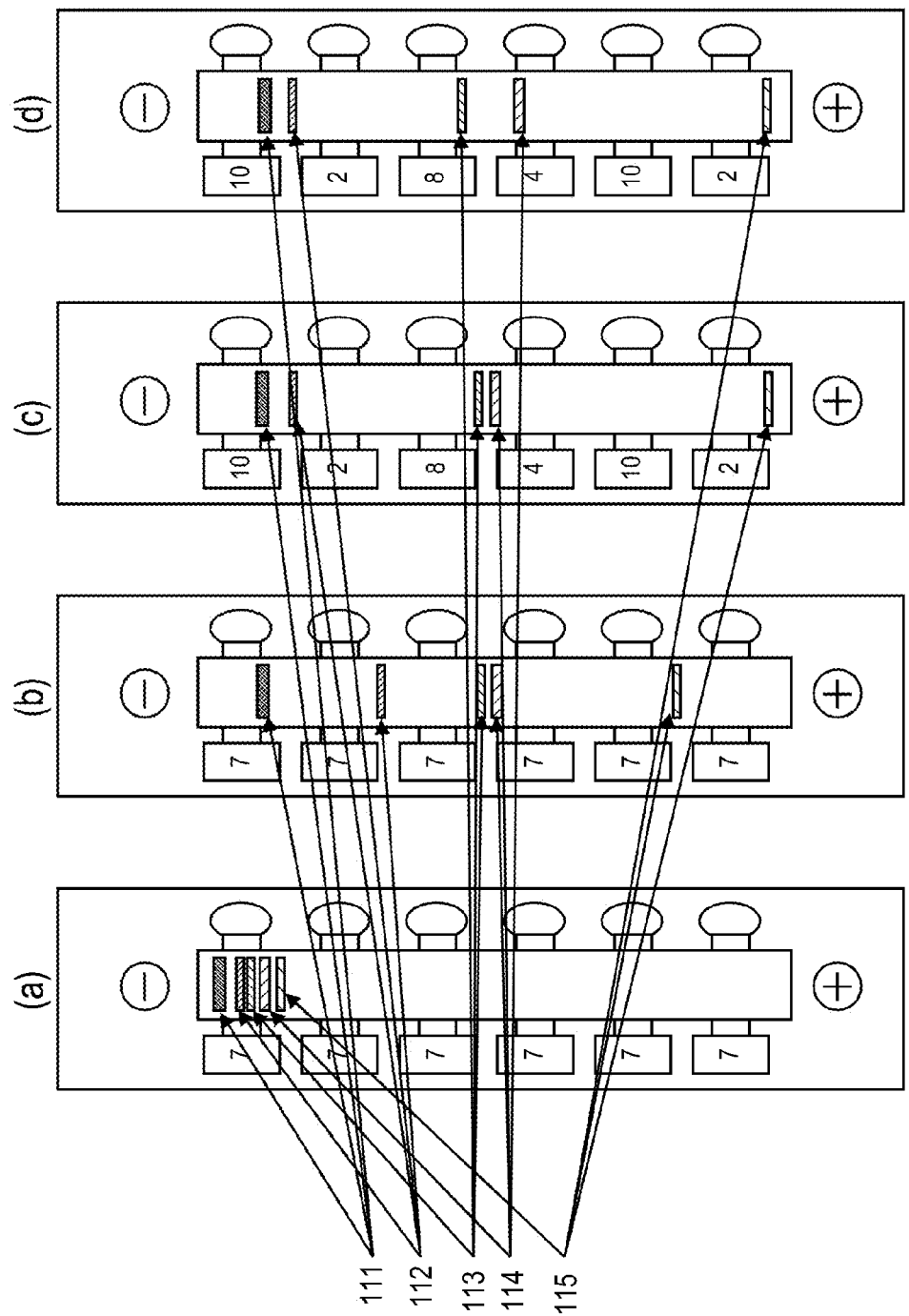
FIG. 11 illustrates an embodiments for separation of molecules based on two separate criteria within one dimension.

In some embodiments, the channel is filled with a gel rather than a liquid and sample components can be separated by mobility and pI criteria. This technology can be designed, for example as shown in FIG. 11. Proton/hydroxide ion injectors facilitate real-time variation of the spatial pH pattern generated by proton and hydroxide ion injection into the separations channel. As a result, the pH gradients used to separate peptides and proteins according to their isoelectric point can be tuned at will, giving way to sequential separation according to isoelectric point and another separation criterion such as electrophoretic mobility or affinity assay. The order of the two separation processes can be chosen at will to guarantee optimal separation.

Common two-dimensional separation gels can be replaced by the disclosed one-dimensional programmable approach. FIG. 11 illustrates an embodiments of such separation, first according to the electrophoretic mobility and then according to the isoelectric point. In these embodiments, the medium in the chamber will be a gel suitable for electrophoresis (including but not limited to linear or crosslinked polymers such as for example agarose, linear or crosslinked polyacrylamide and polymers of acrylamide derivatives or other gel types). Imagine for example a mixture of 5 proteins, two of which (114 and 113) characterized by an identical electrophoretic mobility but different isoelectric point, and two (113 and 112) proteins having the same isoelectric point but different electrophoretic mobility. Further, imagine we aim to isolate the 113 protein. In step (a) one sets the channel's pH to 7 and separates the proteins according to their electrophoretic mobility. Since in the specific example of FIG. 11, the 113 and 114 proteins have higher mobility compared with protein 111 and 112, they separate after a while from the latter (FIG. 11, panel (b)). However, the electrophoretic assay does not separate the 113 protein from the 114 protein because they share a similar electrophoretic mobility. To separate 113 from 114, one tunes the pH profile along the channel in such a way that the 113 protein separates from the 114 one (FIG. 11, panel s (c), (d)). At the same time, proper design of the pH profile in other parts of the channels pushes the 111, 112, and 115 proteins away from the 113 and 114 proteins (FIG. 11, panels (c), (d)). The outcome of this method is isolation of the desired (113) protein according to two distinct criteria, electrophoretic mobility and isoelectric point, both carried out in the same one-dimensional channel.

Figure 12:
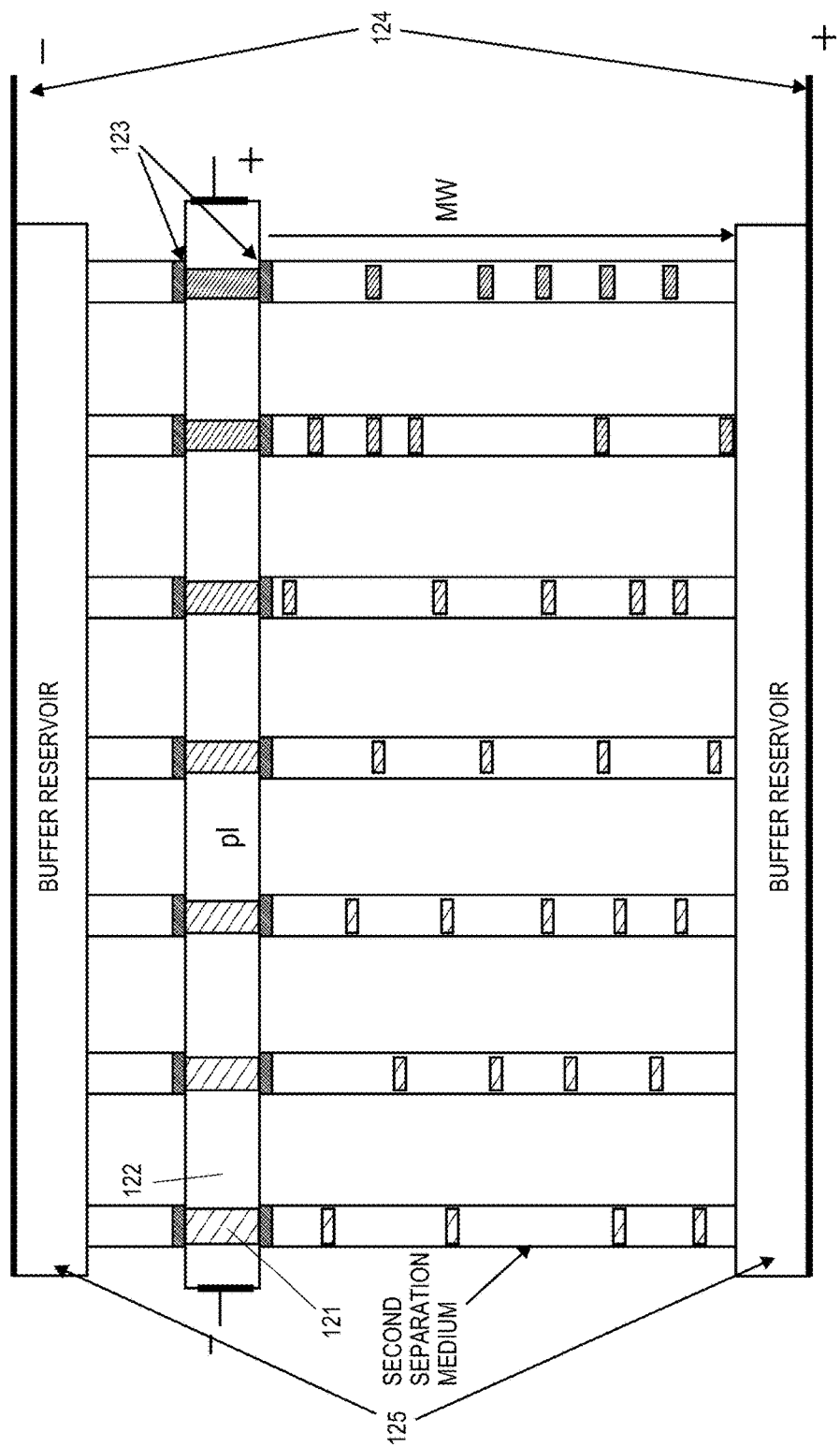
FIG. 12 illustrates separation of molecules by pI and a second separate criteria in another dimension.

In another option, e.g., as shown in FIG. 12, a sample is separated in one dimension by pI and then a second dimension by mobility. In some embodiments, multiple bipolar membranes (121) (and accompanying proton injector or hydroxide injector below or above the plane of the figure) are incorporated in a channel (122) containing a liquid buffer. By either injecting either protons or hydroxide ions and applying voltage along the channel, step gradient is created and the proteins are focused in the corresponding pH step. After the focusing is complete, the valves (123) on both sides of each (e.g., orthogonal) channel are open and voltage is applied at electrodes (124) and the focused proteins are separated in a second dimension separation. The second dimension separation can be performed by molecular weight, charge or charge and molecular weight. For example, in some embodiments, the second dimension comprises electrophoresis, including but not limited to SDS-PAGE or native-PAGE separations. The separation media can be cross linked gel, entangled polymer or a buffer, for example. The buffers for the second separation can be, for example, contained in buffer reservoirs (125). These buffers can be liquid, or can be embedded in a gel. Two different buffers can be utilized if desired to create discontinuous separation for higher resolution.

Two dimensional separation can also be accomplished by utilizing the capture and release method and a single second dimension channel. In this case the first captured fraction will be separated in the second dimension, and than the subsequent released fractions will be separated. The separation can be used for analytical purposes or harvesting ports can be incorporated in the channels to allow the harvesting of the separated analytes if needed.

Methods and Devices for Purifying a Target Molecule Using pI Focusing and Subsequent Crystallization Crystallography is used to analyze the structure of proteins. This is very valuable technique, however also very challenging due to the high requirements for protein purity. Typically the protein is purified to more than 90% pure and is concentrated to about 10 mg/ml. The crystallization process is performed at the pH=pI of the protein. The typical purification process is challenging and frequently 2 to 5 different separation steps are used in order to achieve high purity. After that the protein is usually concentrated using a molecular weight cutoff membrane. An example of protein crystallization and x-ray defraction can be found in, Yamano A, et al., *J Biol. Chem.* 272 (15): 9597-600 (1997).

The present application provides for proton injector and/or hydroxide injector-based methods for purifying proteins for crystallization. In some embodiments, proton/hydroxide injector technology is used to focus the target protein at its pI. This can be done as part of, or in some embodiments, as the last or penultimate step in the purification workflow, e.g., prior to crystallization. In some embodiments, the proton/hydroxide injector step can combined as the last purification and concentration step. In some embodiments, the proton/hydroxide injector step provides an additional purification step orthogonal to the chromatography steps typically used and in the same time can concentrate the protein to very high degree essentially eliminating the need for separate concentration step.

Figure 13:
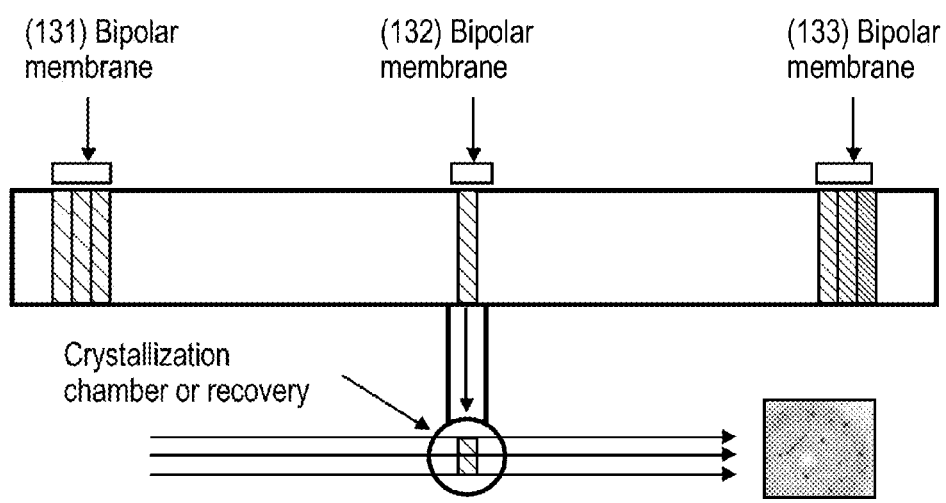
FIG. 13 illustrates an embodiment in which a target protein is separated from contaminants based on pI and subsequently crystallized. The protein is separated from contaminations, moved to a chamber, optionally with an integrated loop, and left for crystallization, flash frozen, and/or imaged.

FIG. 13 illustrates a possible embodiment. In this embodiment the bipolar membrane (131) creates a pH step above the pH of the target protein, therefore trapping all proteins with pI higher than the pI of the target protein. A second proton injector or hydroxide injector separated from the channel by a second bipolar membrane (132) creates a very narrow pH step at the pI of the target protein therefore capturing and concentrating it at this position. A third proton injector or hydroxide injector separated from the channel by a third bipolar membrane (133) creates a pH step below the pI of the target protein therefore capturing all proteins with pI below the pI of the target protein. Once captured and focused in very sharp boundary and therefore highly concentrated, the target protein can either be moved electrophoretically, or by using liquid flow, to a place where the protein can be recovered or stored for crystallization and imaged with X-ray directly in the microfluidic cartridge. In some embodiments as shown in FIG. 6 it is possible to capture and work with multiple proteins at the same time. In some embodiments, an array can be used to crystallize multiple proteins at once or to test multiple conditions for the same protein.

Methods and devices combining proton/hydroxide injectors with affinity agents (e.g., antibodies) are provided. In some embodiments, it is possible to take advantage of the concentration effect of isoelectric focusing/IEF. For example, protein solubility is lowest at/near its isoelectric point/pI. Thus, at or near pI for a target protein within an IEF chamber having a pH step gradient (see, e.g., FIG. 14), proteins will concentrate into/adjacent to proton injection openings (e.g., 'slits') and precipitate. This concentrated precipitate can be used for immuno-detection of proteins of interest (POI), which in some cases can be post-translationally modified (PTM) variants from diverse biological samples. An advantage of this approach is higher resolution (owing to optimal separation via digital pH) and increased sensitivity (owing to concentration of proteins at their pI).

Figure 26A:
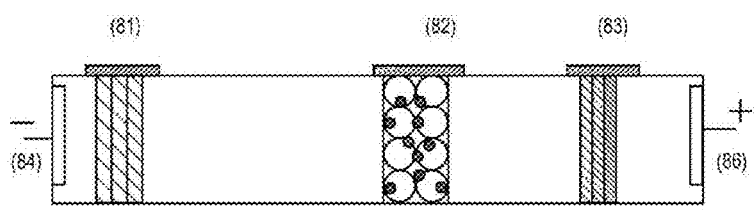
FIG. 26A-C illustrates an embodiment in which a chamber comprises a solid support linked to affinity ligands (affinity agents).
Figure 26B:
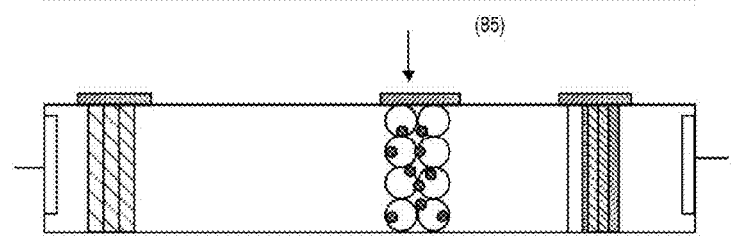
Figure 26C:
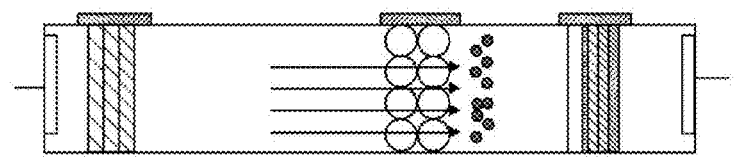

In some embodiments, a protein(s) of interest (POI) can be focused in close proximity to high capacity beads or other solid support with affinity ligand (e.g., an antibody). This is exemplified, for example, in FIG. 26. After capture of the antigen on the beads or other solid support the sample is washed to remove the unbound material from the chamber or vessel. Subsequently, the pH can be changed using the proton/hydroxide injector, thereby denaturing the affinity ligand (e.g., an antibody) and releasing the POI. The POI can be eluted for collection using either a "capture and release" pH gradient or via an electrophoretic gradient or simple elution by washing with an elution reagent such as a denaturing solution or solution containing competitive binding species. Optionally, affinity ligand (e.g., antibody) can be rejuvenated in the vessel by readjustment of the pH so that the antibody resumes its native state. By enclosing the system, the antibody can be reused multiple times with multiple samples for antigen purification. Such methods are useful for, but not limited to, preparative methods of purifying proteins. The affinity ligand in some implementations may be an antibody, a metal chelate, for instance, for capturing poly-His tagged proteins, a glutathione for capturing GST tagged proteins, an oligo for capturing specific nucleic acids, an aptamer or other ligands that may have affinity interactions with biomolecules.

Because antibody-antigen interactions are pH dependent, in some embodiments, first, a pH step is created in close proximity to the antibody, bringing the POI or other target analyte in proximity to the antibody. Subsequently, the pH step gradient is replaced with a pH plateau suited to enable antibody-antigen binding. Subsequently, washing can occur to remove unbound components of the solution.

Methods and devices combining proton/hydroxide injectors with affinity agents (e.g., antibodies) are provided. In some embodiments, it is possible to take advantage of the concentration effect of isoelectric focusing/IEF. For example, protein solubility is lowest at/near its isoelectric point/pI. Thus, at or near pI for a target protein within an IEF chamber having a pH step gradient, proteins will concentrate into/adjacent to proton injection 'slits' and some will precipitate and/or adhere to the chamber. This concentrated precipitate can be used for immuno-detection of proteins of interest (POI), which in some cases can be post-translationally modified (PTM) variants from diverse biological samples. An advantage of this approach is higher resolution (owing to optimal separation via the creation of step gradients using the proton/hydroxide injectors), increased sensitivity (owing to concentration of proteins at their pI) as well as optimization of the pH for the interaction.

In some embodiments, the method comprises the following steps. During step 1, proton injection in an IEF chamber will be used to precipitate POI/PTM variants (e.g., unphosphorylated versus hyperphosphorylated target proteins are 'separated' into openings (e.g., slits) wherein they each remain adhered via interaction with bipolar membrane/IEF chamber. In step 2, polyclonal primary antibodies injected into the IEF chamber will be reacted against POI (e.g., a phosphorylated target protein). In step 3, secondary antibodies coupled with horseradish peroxidase or alkaline phosphatase are introduced similarly as in step 2. In step 4, chemiluminescent or other labeling substrates are introduced into the IEF chamber and emitted signal (e.g., light) is detected. Alternatively, step 4 can be omitted. For example, fluorescently labeled secondary antibodies can be used making step 4 unnecessary. In this embodiment, the unique pI of the antibody/antigen complex could be used instead of a detection reagent in order to purify the complex of interest. While the above discussion is in the context of distinguishing post-translational modifications (PTMs), this method is not limited to PTM differentiation. For example, the methods can be used to detect the amount of any POI in a sample and may also use monoclonal antibodies as any or all antibody binding steps.

Figure 27:
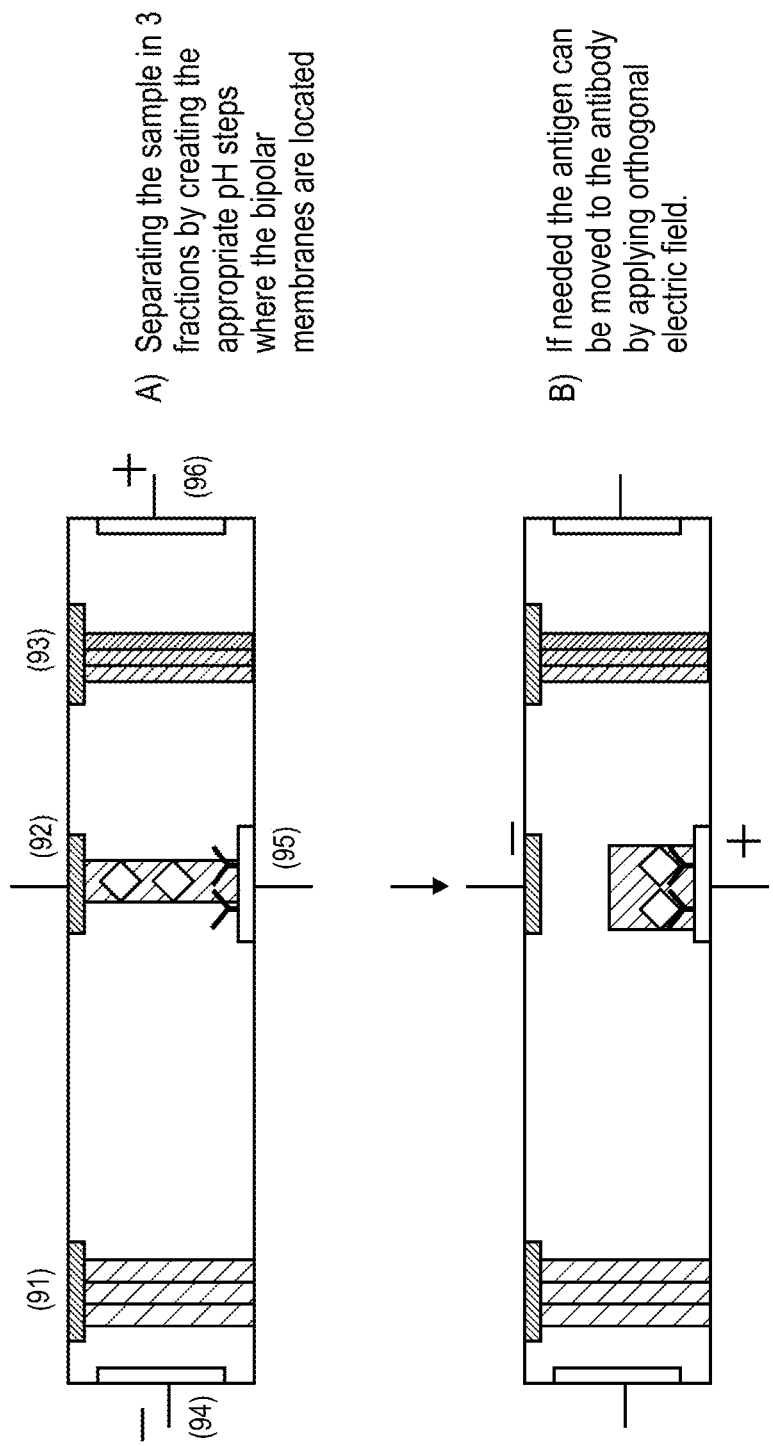
FIG. 27 illustrates an embodiment in which a target analyte is focused to a specific area of the chamber based on pI, thereby locating the target analyte in proximity with antibodies (specific for the target analyte) adhered in the chamber. In some of these embodiments, the target analyte is not precipitated at its pI. In other embodiments, the target analyte is precipitated.

Prior immunodetection methods are performed by adding sample containing the target molecule (antigen) to antibody immobilized on a surface or a bead and waiting for diffusion to take place in order the antigen to come in close proximity to the antibody so the binding can occur. The process is time consuming since there is no specific driving force to bring the antigen in close proximity to the antibody. Also in some cases, the samples are complex (blood, serum, plasma, saliva, urine, lysates, etc.) and there are many other proteins present that may non-specifically bind to the antibody or to the surface around it. In some embodiments of the invention, by using the proton/hydroxide injector technology these two issues are addressed by specifically driving the antigen to the immobilized antibody and concentrating it in close proximity to the antibody, as well as removing portion of the other proteins present in the sample and therefore minimizing the non-specific binding that may occur. See, e.g., FIG. 27. This will speed up the interaction, as well as deliver higher quality results with less non-specific interactions contributing to the signal.

In some embodiments, the protein sample is separated in three fractions (step A, FIG. 27):

The proteins with pI higher than the pI of the target protein (antigen) are isoelectrically focused in the region of bipolar membrane (91) where a pH step encompassing pH higher than the pI of the antigen is created.

The protein of interest is focused in the region of bipolar membrane (92) by creating a narrow pH range step encompassing the pI of the antigen The proteins with pI lower than the pI of the antigen are isoelectrically focused in the region of bipolar membrane (93) where pH step with range below the pI of the antigen is created This way the antigen is captured and concentrated in the area of the binding antibody. In some embodiments, the conditions are selected to prevent precipitation of the target analyte once the target arrives at its pI. For example, in some embodiments, the solution in the chamber comprises a sufficient amount of a non-ionic detergent or other agent (e.g., organic solvent(s)) to promote solubility of the target analyte.

Because antibody-antigen interactions are pH dependent, in some embodiments, first, a pH step is created in close proximity to the antibody, bringing the antigen in proximity to the antibody. Subsequently, the pH step gradient is replaced with a pH plateau suited to enable antibody-antigen binding.

The amount of the antigen bound to the antibody can be detected as desired. For example, the antibody can be immobilized on a sensor capable of detecting binding events (such as SPR, nano wire or other sensor types) or the antigen can be detected by performing sandwich type assay such as ELISA by using second antibody that is specific to the antigen but binds to a domain different than the domain that the immobilized antibody binds. In some implementations the sample may be pre-labeled, so the bound target analyte is detected after binding to the affinity ligand specific to this analyte.

Additional step (B) may be performed if needed (by applying the appropriate electric field) to further move the antigen to the surface (95) where the antibody is immobilized. The proposed methodology can work with various molecules as long as they have isoelectric point. For instance, instead of antibody, other binding ligands may be used, such as for example other proteins, peptides, DNA, and small molecules (including but not limited to aptamers).

Figure 16:
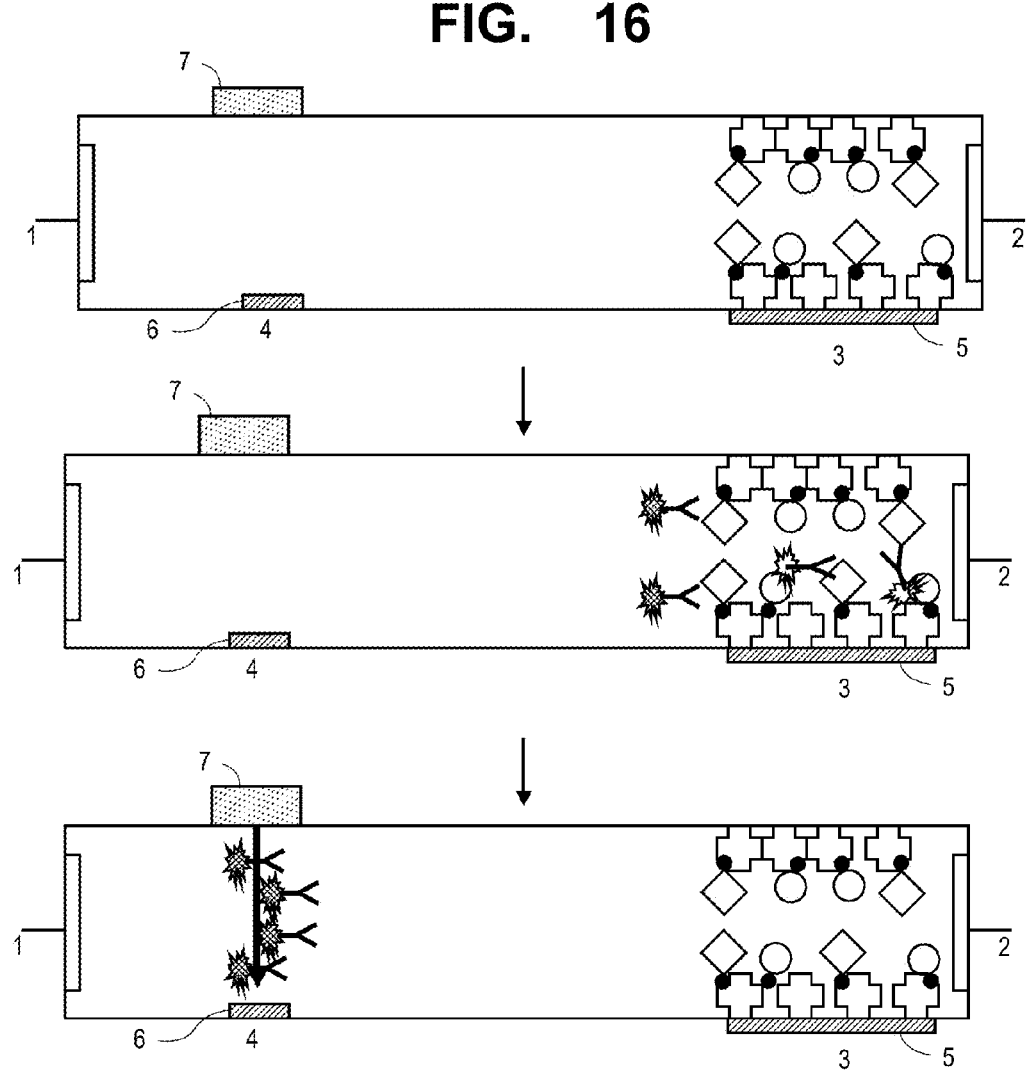
FIG. 16 schematically illustrates an apparatus configuration and its use to detect a target molecule (represented by diamonds). At the top, the figure shows an apparatus in a first time point. The plus symbols represent streptavidin, and the circles and diamonds represent components of a sample, with the diamonds being the target molecule. The smaller filled circles represent biotin moieties on the sample components. The middle section of the figure illustrates the apparatus at a second time point with addition of a labeled affinity agent specific for the target molecule. The bottom section of the figure illustrates a third time point following a wash and subsequent elution of the detectably-labeled affinity agents and movement of the detectably-labeled affinity agents to a second sub-area (4) of the apparatus. Movement of the detectably-labeled affinity agent can be achieved, for example, by setting the pH in the first sub-area (3) to a pH different than the pI of the detectably-labeled affinity agent such that the detectably-labeled affinity agent has a charge. The pH of the solution in proximity to the first sub-area (3) can be controlled by an ion injector (5). The electrodes (1, 2) can then generate a field in which the charged detectably-labeled affinity agent moves towards the second sub-area (4). Item 6 represents an ion injector that can control the pH in proximity to the second sub-area (4). The ion injector (6) can generate a pH at or close to the pI of the detectably-labeled, such that when the detectably-labeled affinity agent is in proximity to the ion injector (6) the detectably-labeled affinity agent is no longer charged and therefore no longer moves in the electrical field. Once located in the second sub-area (4), the detectably-labeled affinity agents can be detected or quantified by a detector (7).

In one aspect depicted in FIG. 16, the sample is applied to the solution in the chamber and at least some components of the sample are allowed to localize in the first sub-area. Localization to the first sub-area can be achieved, for example, by tagging components of the sample prior to applying the sample to the chamber, and then localizing the tagged components by linking an affinity agent to the first sub-area where the affinity agent binds the tag. This aspect is depicted in FIG. 16, in which small filled circles represent the tag and large crosses represent the affinity agent. As one example, the tag can be biotin and the affinity agent that binds biotin can be avidin or streptavidin. Biotinylation of the sample is not specific for the target molecule in the sample and thus other components of the sample will also be localized to the first sub-area. Following localization, the solution can be changed and the chamber washed, thereby removing sample components that are not localized via the affinity agent to the first sub-area.

In another aspect (e.g., depicted in FIG. 17), the target molecule in the sample can be selectively localized to the first sub-area of the chamber by an affinity agent linked to the first-sub-area, where the affinity agent specifically binds to the target molecule. For example, the affinity agent can be an antibody that specifically binds the target molecule. In this aspect, the target molecule is the primary or only component of the sample localized to the first sub-area due to the target's affinity for the affinity agent. As in the aspect described with reference to FIG. 16, in some aspects, following localization, the chamber is washed, thereby removing sample components that are not localized via the affinity agent to the first sub-area.

Figure 20:
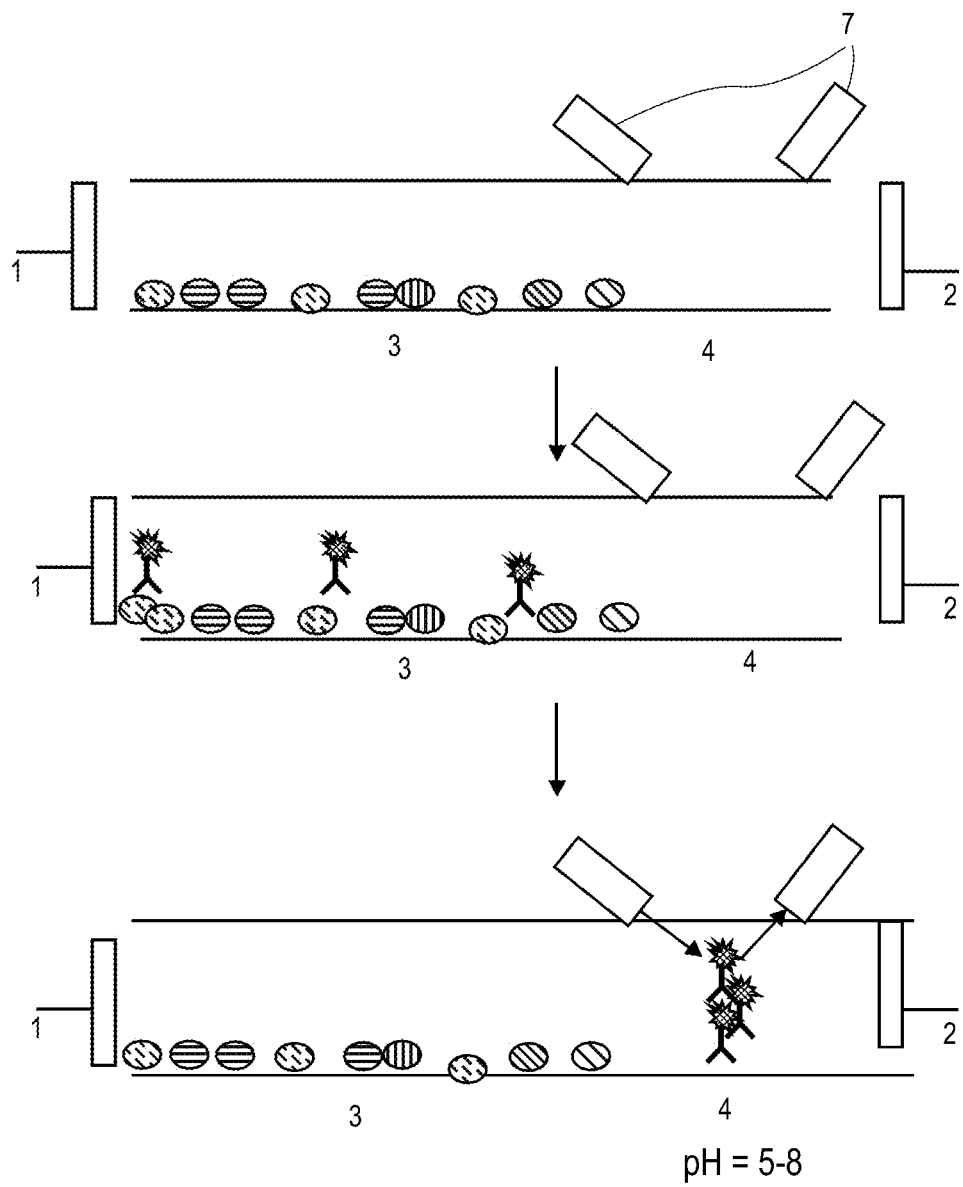
FIG. 20 schematically illustrates an apparatus configuration and its use to detect multiple different target molecules. The top portion of the figure shows a complex sample composed of multiple different components (represented by ovals). The sample components are linked to a first sub-area (3) of the chamber of the apparatus. The middle portion of the figure illustrates the apparatus following addition of detectably-labeled affinity agents specific for two or more different target molecules. In the illustration, three different affinity agents are included, each binding a different target molecule. For example, the three targets could be three different types of proteins. The bottom portion of the figure illustrates a time point after non-binding affinity agents have been washed away and bound affinity agents are subsequently eluted. Optionally, elution can be achieved by changing the pH of the solution in the chamber, e.g., with proton or hydroxide injectors (not shown). The electrodes (1,2) on sides of the chamber can generate an electrical field, thereby moving charged molecules, including the eluted detectably-labeled affinity agents, to a second sub-area (4) of the chamber. The moved detectably-labeled affinity agents can be localized at the second sub-area by generating a pH at or close to the pI of the detectably-labeled affinity agents in the solution in proximity to the second sub-area (4), e.g., with one or more proton or hydroxide injector (not shown). For example, the pH in proximity to the second sub-area can be between 5-8. Once localized, the different detectably-labeled affinity agents can be individually detected, for example if the affinity agents for different targets comprise different detectable labels that can be distinguished (e.g., in the case of fluorescent labels, that emit signal at different wavelengths or that are excited at different wavelengths). The signal of the labels can be detected with a detector (7).

In another aspect, the sample is linked directly to a solid surface in the chamber (e.g., to a membrane in the chamber), thereby localizing components of the sample to a sub-area of the chamber. Components can be linked to the solid surface as desired. For example, the sample can be immobilized to a protein binding membrane (e.g., nitrocellulose affixed to the chamber). The sample can be covalently linked with the use of a cross linker such as formaldehyde, EDC or others. This aspect is depicted in FIG. 20.

Following localization of some or all components of the sample to the first sub-area, a detectably-labeled affinity agent that specifically binds the target molecule is added to the chamber and incubated under conditions to allow for binding of the affinity agent to the target molecule, if present. For instance, many antibodies will bind to their respective target molecule at a pH of ~7-8. In some aspects, the detectably-labeled affinity agent is an antibody. Following incubation, excess affinity agent is washed away, thereby leaving detectably-labeled affinity agent specifically bound to the localized target molecule. This aspect is shown in the second panel of FIG. 16 and FIG. 17.

Figure 17:
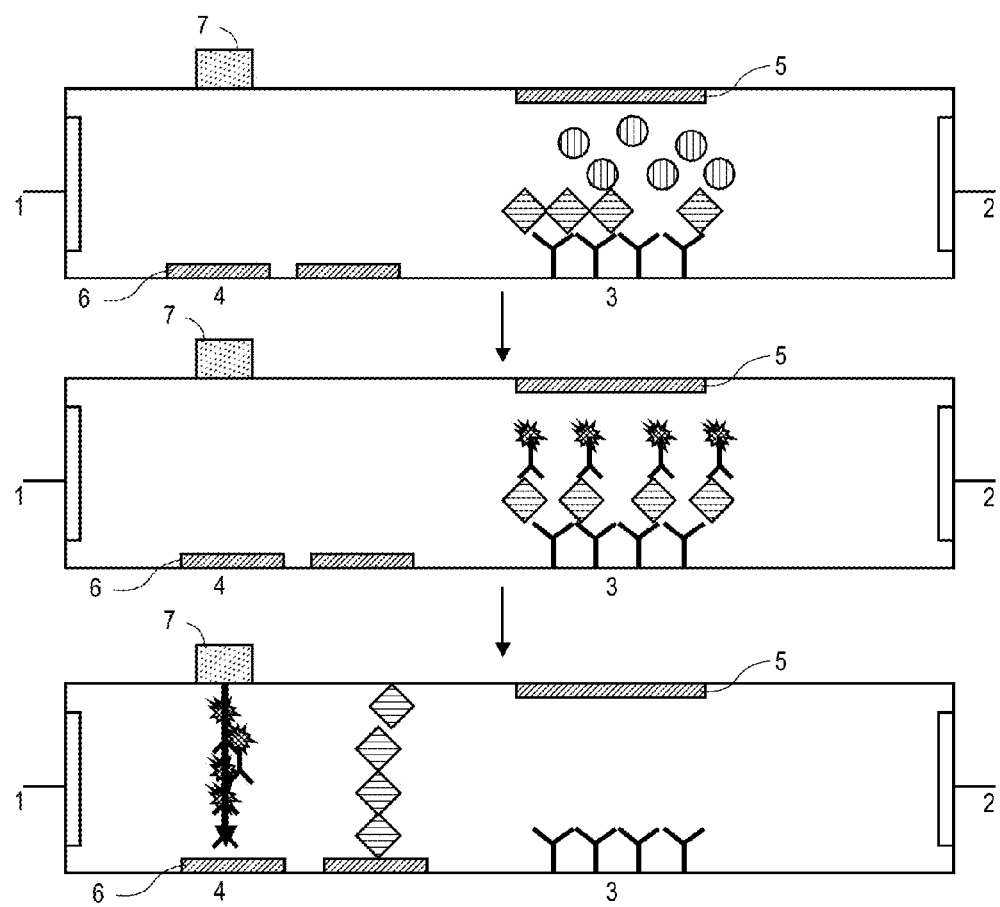
FIG. 17 schematically illustrates an apparatus configuration and its use to detect a target molecule (represented by diamonds). At the top, the figure shows the sample is initially provided near a first sub-area (3) of the apparatus, where affinity agents are linked to the apparatus. The affinity agents specifically bind to the target molecules (diamonds) in the sample while not binding other components (represented by circles) of the sample. The middle section of the figure shows the addition of detectably-labeled affinity agents specific for the target molecule, acting in a sandwich-like format. The bottom section of the figure shows the apparatus following a wash and subsequent elution of the detectably-labeled affinity agents and movement of the detectably-labeled affinity agents to a second sub-area (4) of the apparatus. Movement of the detectably-labeled affinity agent can be achieved, for example, by setting the pH in the first sub-area (3) to a pH different than the pI of the detectably-labeled affinity agent such that the detectably-labeled affinity agent has a charge. The pH of the solution in proximity to the first sub-area (3) can be controlled by an ion injector (5). The electrodes (1, 2) can then generate a field in which the charged detectably-labeled affinity agent moves towards the second sub-area (4). Item 6 represents an ion injector that can control the pH in proximity to the second sub-area (4). The ion injector (6) can generate a pH at or close to the pI of the detectably-labeled affinity agent, such that when the detectably-labeled affinity agent is in proximity to the ion injector (6) the detectably-labeled affinity agent is no longer substantially charged and therefore no longer moves in the electrical field. Once located in the second sub-area (4), the detectably-labeled affinity agents can be detected or quantified by a detector (7).

The conditions in the chamber can be subsequently changed to elute the detectably-labeled affinity agent from the target molecule. The conditions can be changed, for example, by changing the pH of the solution by adding base or acid or changing the solution completely to replace the solution with a solution having a different pH or salt concentration to elute the detectably-labeled affinity agent. In some embodiments, acidic (e.g., 1-2) pH or basic (e.g., 10-12) pH can be used to elute target molecule from the affinity agent (e.g., antibody). In some aspects, one or more proton or hydroxide injectors can be used to electronically change the pH of the solution in the chamber or at least in the solution in proximity to the first sub-area. FIGS. 16 and 17 depict an embodiment in which the portion of the chamber having the first sub-area comprises an proton or hydroxide injector. A more detailed description of proton or hydroxide injectors is provided below.

The conditions can also be applied such that the eluted detectably-labeled affinity agent has a desired charge. For example, the overall charge of the affinity agent will be negative if the pH of the solution is above the pI of the affinity agent and the overall charge of the affinity agent will be positive if the pH of the solution is below the pI of the affinity agent. Once the charge of the affinity agent has the desired charge, a voltage difference can be applied across the electrodes, thereby generating an electric field that moves the charged affinity agents in the solution towards the appropriate electrode (cathode or anode depending on charge of the affinity agent).

In one aspect the detectably-labeled affinity agent is moved in solution to the location of an electrode, where the affinity agent is detected and/or quantified. Alternatively, the detectably-labeled affinity agent can be localized to a second sub-area of the chamber by setting the pH of the solution in proximity to the second sub-area to a pH at or close to the pI of the detectably-labeled affinity agent. The pH of the solution in proximity to the second sub-area can be controlled, for example, by inclusion of one or more proton or hydroxide injectors at the second sub-area. While not intending to be limited to a particular mechanism of action, it is believed that the pH of the solution in proximity to the second sub-area need not be exactly the pI of the detectably-labeled affinity agent but may merely be close to the pI to substantially eliminate overall charge of the detectably-labeled affinity agent, thereby stopping further movement of the detectably-labeled affinity agent. See, the third panel of FIGS. 16 and 17.

Once the detectably-labeled affinity agent is positioned at the electrode or at the second sub-area, the presence or quantity of the detectably-labeled affinity agent is detected. Detection of the detectably-labeled affinity agent will depend on the nature of the label. For example, if the label is a fluorescent dye, an optical detector set to measure signal at the appropriate wave length of the fluorescent dye can be used for detection. Quantity of the detectably-labeled affinity agent present will be proportional to the amount of target molecule in the original sample. Actual quantity of target molecule can be determined, if desired, using one or more standards and interpolation analysis.

Figure 21:
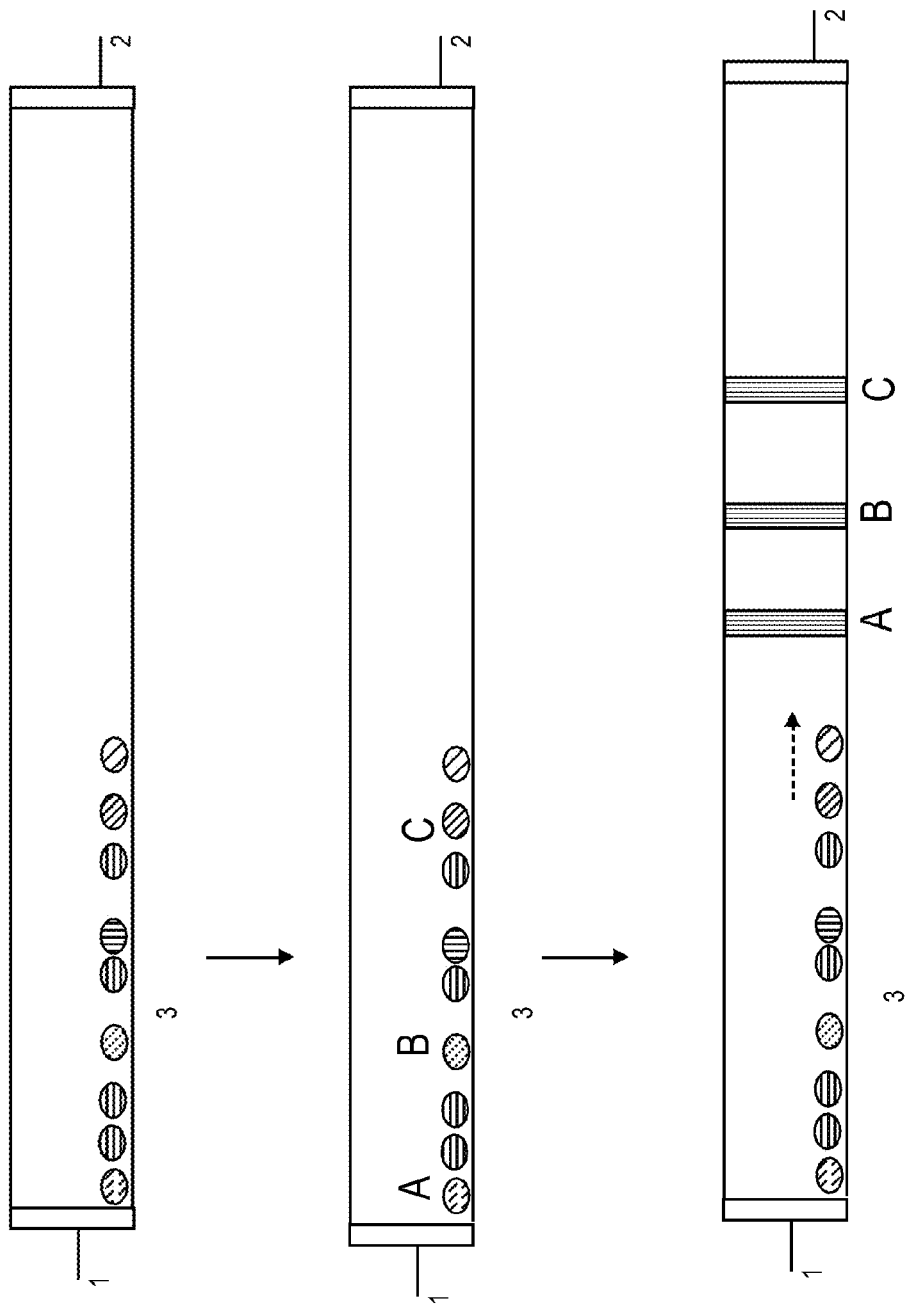
FIG. 21 schematically illustrates an apparatus configuration and its use to detect multiple different target molecules. The top portion of the figure shows a complex sample composed of multiple different components (represented by ovals). The sample components are linked to a first sub-area (3) of the chamber of the apparatus. The middle portion of the figure illustrates the apparatus following addition of detectably-labeled affinity agents (A, B, C) specific for two or more different target molecules. In the illustration, three different affinity agents (A, B, C) are included, each binding a different target molecule. For example, the three targets could be three different types of proteins. The bottom portion of the figure illustrates a time point after non-binding affinity agents have been washed away and bound affinity agents are subsequently eluted. Optionally, elution can be achieved by changing the pH of the solution in the chamber, e.g., with proton or hydroxide injectors (not shown). The electrodes (1,2) on sides of the chamber can generate an electrical field, thereby moving charged molecules, including the eluted detectably-labeled affinity agents, to different sub-areas (A, B, C) of the chamber, each sub-area representing localization of a different affinity agent. This can be achieved, for example, where different detectably-labeled affinity agents have a different pI. Thus, by using a different proton or hydroxide injector(s) at different sub-areas to generate a localized pH at or close to the pI of different affinity agents, detection of signal at a particular sub-area should be generated only, or substantially only, from one particular affinity agent type. In this configuration, different detectable labels can be, but do not have to be, used by different affinity agents. The moved detectably-labeled affinity agents can be localized at the sub-areas by generating a pH at or close to the pI of the detectably-labeled affinity agents in the solution in proximity to the second sub-area (4), e.g., with one or more proton or hydroxide injector (not shown).
Figure 22:
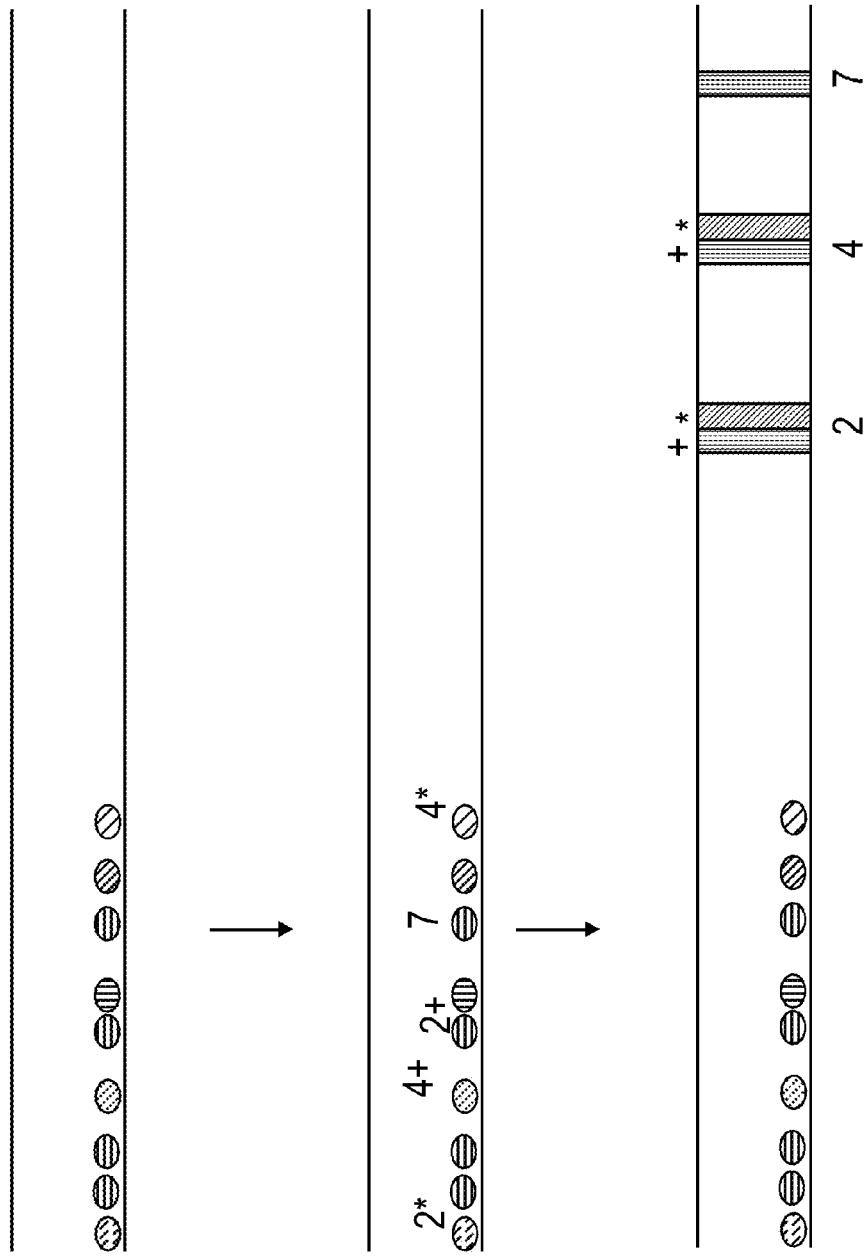
FIG. 22 schematically illustrates an apparatus configuration and its use to detect multiple different target molecules.

The embodiments described above (e.g., as depicted in FIGS. 16 and 17) can be modified to detect multiple target molecules in parallel (multiplexed). Representative multiplexing embodiments are depicted in FIGS. 21, 22, and 23. In some embodiments, at least some components of the sample are localized to a first sub-area of the chamber as described above, contacted with a plurality (e.g., 2, 3, 4, 5, or more) different detectably-labeled affinity agents, wherein the different affinity agents specifically bind different targets and have different detectable labels such that the different labels can be distinguished (e.g., are fluorescent at different wavelengths), under conditions such that the affinity agents bind their respective targets if present. Excess unbound affinity agents is washed away and the conditions are changed to elute the affinity agent from the target molecules. A voltage difference is then applied across the electrodes, thereby generating an electric field that moves the eluted affinity agents to a second sub-area (for example, labeled "4" in FIG. 20). As described elsewhere, in some embodiments, the eluted affinity agents accumulate at the second sub-area because the solution in proximity to the second sub-area has a pH at or close to the pI of the affinity agents. The pH of the solution in proximity to the second sub-area can be controlled by one or more proton or hydroxide injectors. If the different affinity agents have different pIs, the pH can be adjusted in series for each affinity agent, with quantification of signal from the separate affinity agents determined before the pH is changed to accommodate the next affinity agent. Quantity of different affinity agents at the second sub-area can be detected by detecting the different labels associated with the different affinity agents. This aspect is illustrated, for example, in FIG. 20.

Alternatively, in some embodiments, at least some components of the sample are localized to a first sub-area of the chamber as described above, contacted with a plurality (e.g., 2, 3, 4, 5, or more) different detectably-labeled affinity agents, wherein the labeled affinity agents specifically bind different targets and have different pIs. The affinity agents in this embodiment can have the same or different label. Excess unbound affinity agents is washed away and the conditions are changed to elute the affinity agent from the target molecules. A voltage difference is then applied across the electrodes, thereby generating an electric field that moves the eluted affinity agents to different sub-areas, where the different sub-area have solution at different pH corresponding to the pI of a particular affinity agent. See, for example, FIG. 21, where "A", "B", and "C" represent antibodies with affinity to different targets. As described elsewhere, the eluted affinity agents accumulate at the different sub-areas because the solution in proximity to the different sub-areas has a pH at or close to the pI of a particular affinity agent. The pH of the solution in proximity to the sub-areas can be controlled by one or more proton or hydroxide injectors.

As depicted in FIG. 22, the two types of multiplexing discussed above (multiplexing by different label or multiplexing by different pI of affinity agent) can be combined if desired. For example, different affinity agents having the same pI can be differentially labeled while other affinity agents having different pIs can be distinguished by pI. This aspect is depicted in FIG. 22 where different antibodies are represented by numbers representing their pI. Other symbols (*, +) indicate affinity agents with different affinity. Thus, "2*" and "2+" represent different antibodies, have different labels (*,+) but the same pI (2). They are positioned to the same sub-area, having a pH of about 2, and are detected by detecting their different signals (* and +). In any of the multiplexing embodiments, 2, 3, 4, 5, 6, 7, 8, 9, or more different affinity agents (different labels, different pI, or a combination thereof) can be used. FIG. 23 illustrates how this aspect can be performed in parallel for multiple samples.

Figure 18:
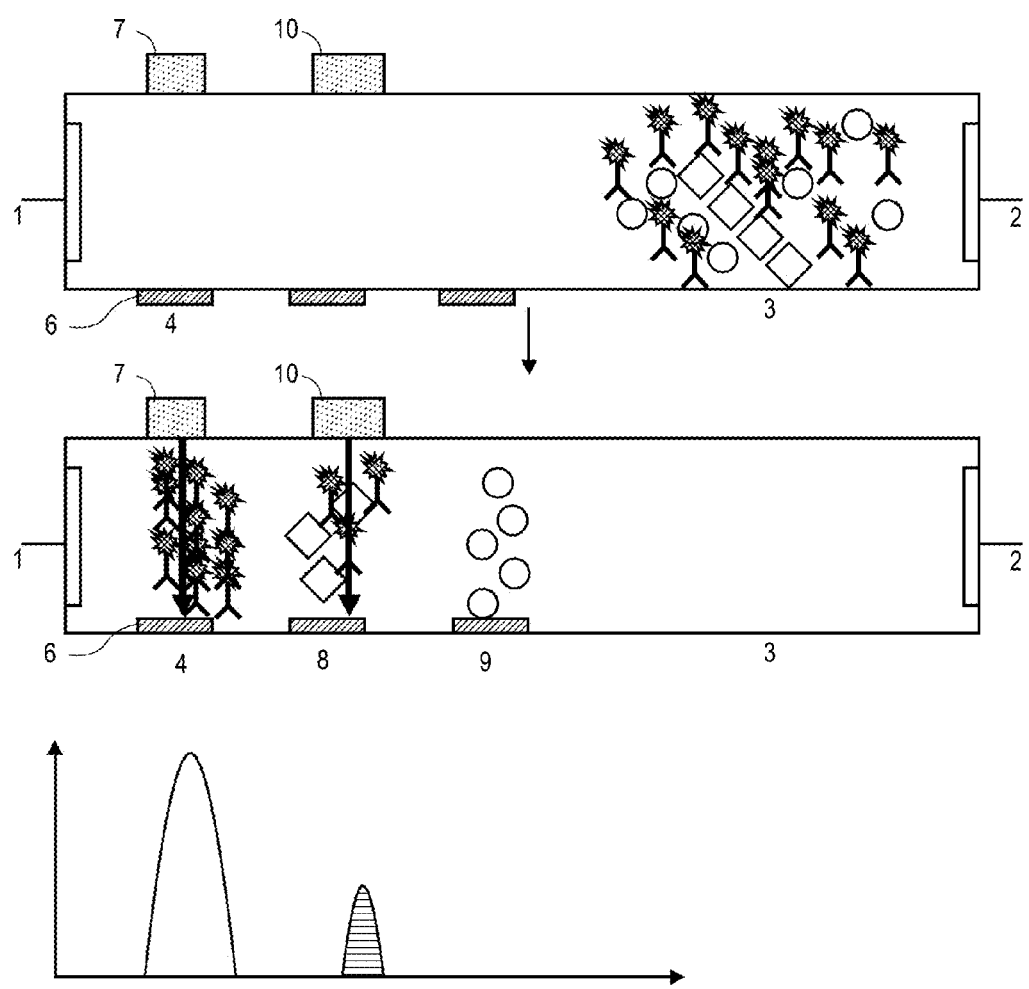
FIG. 18 schematically illustrates an apparatus configuration and its use to detect a target molecule (represented by diamonds). At the top, the figure shows the sample (diamonds and unwanted sample components (circles)) is initially provided near a first sub-area (3) of the apparatus. Detectably-labeled affinity agents are also provided in contact with the sample, either having been mixed with the sample beforehand or added before or after the sample is added. The conditions allow for binding of the affinity agents to target molecules, if present in the sample. The middle section of the figure shows that the detectably-labeled affinity agents that did not bind a target molecule are moved to a second sub-area (4) of the apparatus different from a third sub-area (8) where detectably-labeled affinity agent bound to target molecules are located. Optionally, other components of the sample are localized to a fourth sub-area (9). Movement of these molecules (detectably-labeled affinity agent bound to target molecules, detectably-labeled affinity agent not bound to target molecules, optionally other sample components) is achieved as discussed above, i.e., using the electrodes to move charged molecules to a sub-area where the pH is close to or at the molecules' pI. Different detectors (7, 10) can be used to quantify the separate amounts of detectably-labeled affinity agent bound to target molecules and detectably-labeled affinity agent not bound to target molecules, wherein the ratio of these amounts can be used to determine the amount of target molecules in the sample. The bottom part of figure illustrates a prophetic quantitative analysis of amounts of detectably-labeled affinity agent bound to target molecules and detectably-labeled affinity agent not bound to target molecules.

A different aspect is depicted in FIG. 18. In this aspect, the sample complexed with the detectably-labeled affinity agent specific for the target molecule is provided in the chamber. In some aspects, the detectably-labeled affinity agent and the sample are mixed prior to addition to the chamber. Alternatively, the detectably-labeled affinity agent can be added before or after the sample is added to the chamber and then submitted to conditions to allow for binding of the detectably-labeled affinity agent to the target molecule, if present. The conditions will also be of an appropriate pH such that the detectably-labeled affinity agent bound to the target molecule is charged, i.e., the pH is higher or lower than the pI of the complex of the detectably-labeled affinity agent bound to the target molecule. In some embodiments, the conditions are also designed such that unbound detectably-labeled affinity agent is also charged, though the pI of the unbound detectably-labeled affinity agent will be different than the pI of the complex formed from the detectably-labeled affinity agent bound to the target molecule.

Subsequently, a voltage difference can be applied across the electrodes, thereby moving the charged complex formed from the detectably-labeled affinity agent bound to the target molecule towards the appropriate electrode (cathode or anode depending on charge of the complex). In one aspect the complex is moved in solution to the location of an electrode, where the complex is detected and/or quantified. Alternatively, the complex can be localized to a second sub-area of the chamber by setting the pH of the solution in proximity to the second sub-area to a pH at or close to the pI of the complex. The pH of the solution in proximity to the second sub-area can be controlled, for example, by inclusion of one or more proton or hydroxide injectors at the second sub-area. The quantity of the complex can then be detected with an appropriately-located detector(s) and correlated to the quantity of the target molecule in the sample.

In some embodiments, the unbound detectably-labeled affinity agent (i.e., the excess affinity agent lacking a target molecule "partner") is localized to a third sub-area (see, e.g., FIG. 18, label 8) of the chamber by setting the pH of the solution in proximity to the third sub-area to a pH at or close to the pI of the unbound detectably-labeled affinity agent. As noted above, the pI of the unbound detectably-labeled affinity agent will be different from the pI complex and therefore the location of the second and third sub-areas can be located in distinct locations in the chamber, thereby allowing for separate detection and quantification of bound and unbound detectably-labeled affinity agent. The pH of the solution in proximity to the third sub-area can be controlled, for example, by inclusion of one or more proton or hydroxide injectors at the third sub-area. The quantity of the complex can then be correlated based on the ratio of bound to unbound detectably-labeled affinity agent, assuming the amount of starting detectably-labeled affinity agent is known. If desired, unbound target molecule can also be localized by the pI of the unbound target molecule to a fourth sub-area (labeled 9 in FIG. 18).

Figure 19:
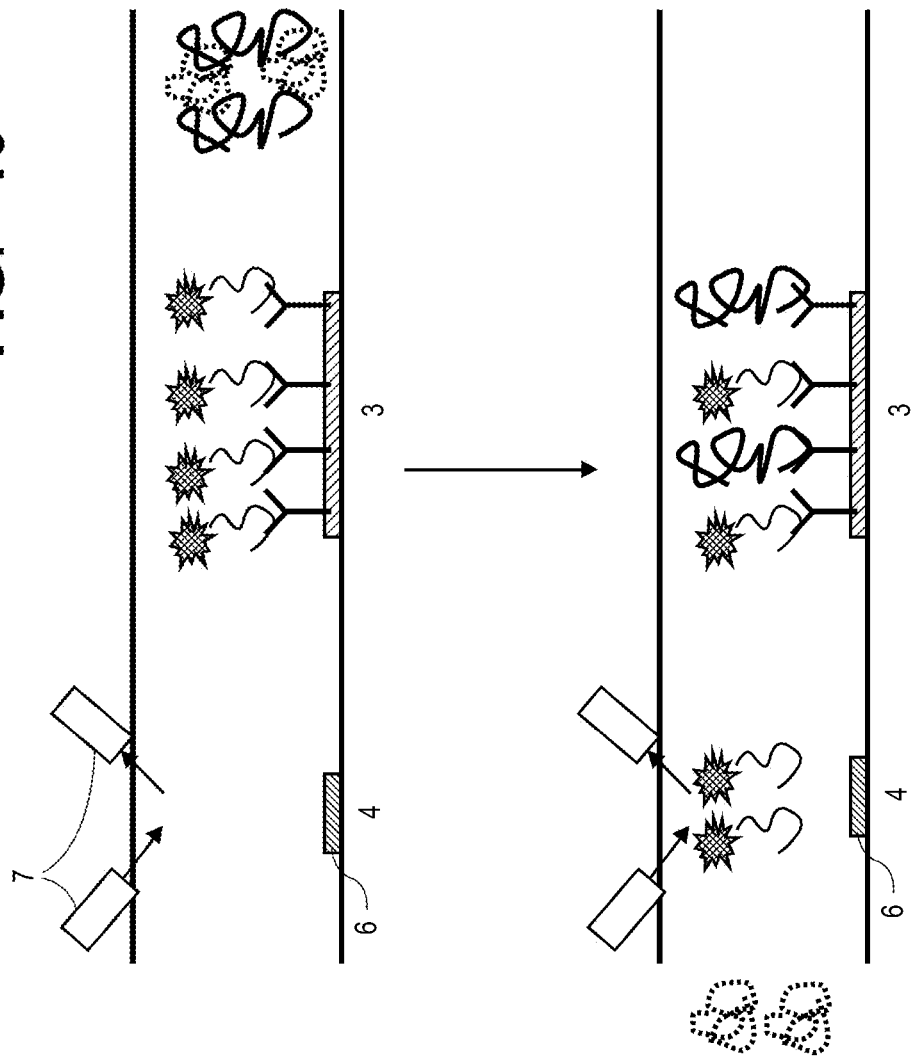
FIG. 19 schematically illustrates an apparatus configuration and its use to detect a target molecule. At the top, the figure shows an initial time point at which a chamber in the apparatus comprises affinity agents for target molecules linked to a first chamber sub-area (3). Bound to these linked affinity agents are detectably-labeled molecules that compete for binding to the affinity agents with the target molecules. As shown in the right portion of the chamber, a sample is provided that contains a target molecule in addition to other molecules. Upon contact of the sample with the linked affinity agents, target molecules in the sample will compete and displace some amount of the detectably-labeled molecules on the affinity agents. The displaced detectably-labeled molecules can then be moved to a second sub-area (4) of the chamber (for example, using electrodes to generate an electrical field that moves charged detectably-labeled molecules, as described above and elsewhere herein) where one or more detector (7) is used to detect displaced detectably-labeled molecules. See, bottom part of figure. While not shown in the figure, proton or hydroxide injectors can be placed, for example, in proximity to the first (3) or second (4) sub-areas to set the pH such that, for instance, molecules to be moved with electrical fields are charged, or not, as appropriate to achieve their movement.

In yet another aspect, the sample is applied to the solution in a chamber having in a first sub-area (e.g., label 3 in FIG. 19). In this aspect, an affinity agent specific for the target molecule is linked to the first sub-area. A labeled competitor molecule that competes with a target molecule for binding to the affinity agent is bound to the affinity agent. The sample can moved to the first sub-area under conditions to allow for binding competition between any target molecule present in the sample and the labeled competitor molecule. The amount of labeled competitor molecule displaced from the affinity agent will be proportional to the quantity of target molecule present in the sample. Following displacement of the labeled competitor molecule, a voltage difference is applied between the electrodes in the chamber, thereby moving the displaced labeled competitor molecule to a location where the labeled competitor molecule can be detected. The location can be adjacent to an electrode, or can be a second sub-area (4 as depicted in FIG. 19). In some embodiments, the detectably-labeled affinity agent can be localized to a second sub-area of the chamber by setting the pH of the solution in proximity to the second sub-area to a pH at or close to the pI of the labeled competitor molecule. The pH of the solution in proximity to the second sub-area can be controlled, for example, by inclusion of one or more proton or hydroxide injectors at the second sub-area. The labeled competitor molecule localized at the second sub-area can subsequently be detected.

The labeled competitor molecule can be any molecule that competes for binding to the affinity agent with the target molecule. In some embodiments, the labeled competitor molecule comprises the target molecule, or an antigenic fragment thereof, linked to a detectable label.

In another aspect, an affinity agent specific for the target molecule is linked to the first sub-area. A labeled competitor molecule that competes with a target molecule for binding to the affinity agent is bound to the affinity agent similar to as described above. However, in this aspect, instead of starting with the labeled competitor molecule bound to the affinity agent, a known amount of labeled competitor molecule is mixed with the sample. The labeled competitor molecule can be mixed with the sample prior to addition of the sample to the solution in the chamber. Alternatively, the sample and labeled competitor molecule can be added to the solution in the chamber and allowed to mix prior to moving the sample and labeled competitor molecule to the first-sub-area. Once moved into proximity of the first sub-area and the linked affinity agents attached thereto, the sample and labeled competitor molecule are submitted to conditions to allow for binding of target molecules in the sample, as well as labeled competitor molecule to the affinity agents. The remaining unbound labeled competitor molecule can then be moved to a second sub-area by submitting a voltage difference to the electrodes, thereby moving the charged labeled competitor molecule in an electrical field. As described elsewhere herein, the unbound labeled competitor molecule will stop at the second sub-area when the solution in proximity to the second sub-area has a pH at or close to the pI of the unbound labeled competitor molecule. The pH of the solution in proximity to the second sub-area can be controlled, for example, by inclusion of one or more proton or hydroxide injectors (6) at the second sub-area. The unbound labeled competitor molecule at the second sub-area can then be detected and quantified. The amount of the unbound labeled competitor molecule, as well as the ratio of unbound labeled competitor molecule compared to the starting amount of labeled competitor molecule will be proportional to the amount of target molecules originally in the sample.

Figure 24:
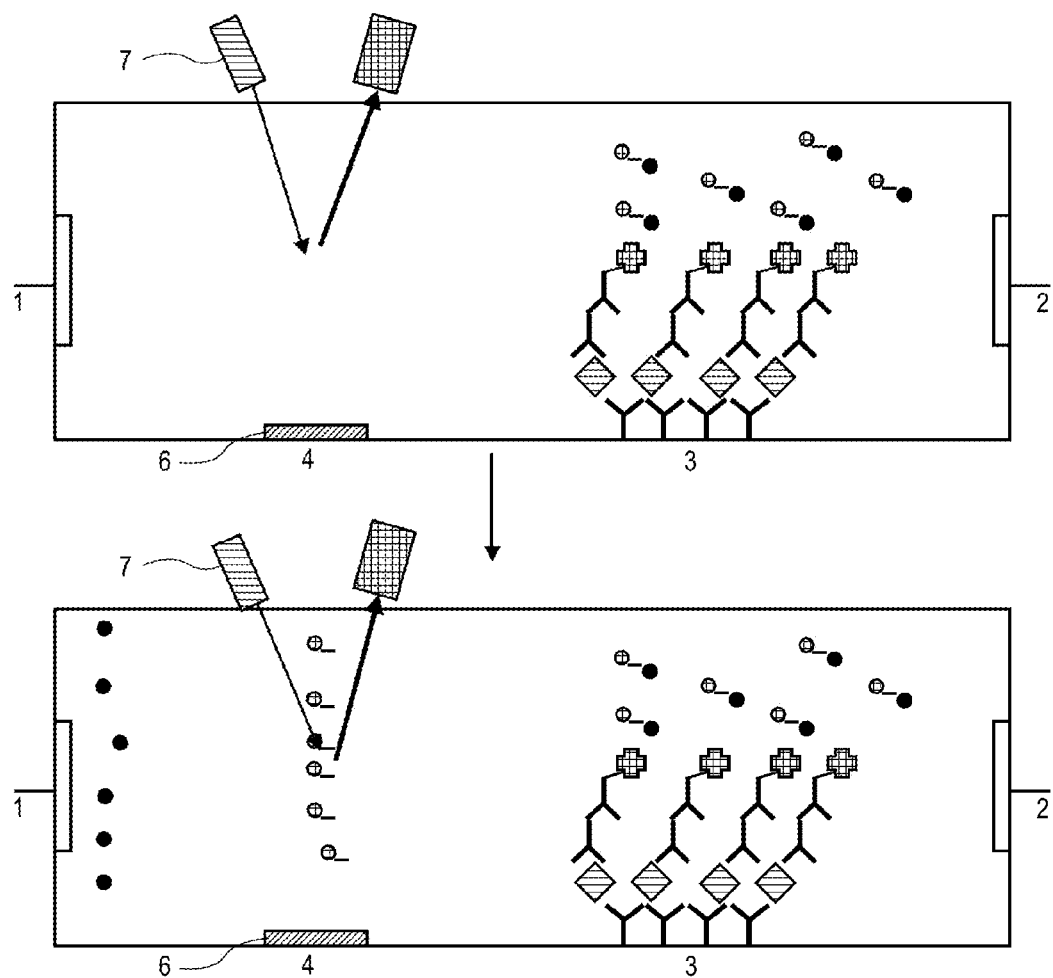
FIG. 24 schematically illustrates an apparatus configuration and its use to detect target molecules from a sample. In the aspect illustrated in FIG. 24, an affinity agent labeled with an enzyme that renders a substrate detectable is used. The apparatus comprises a chamber having an affinity agent specific for the target molecule linked to a first sub-area (3) of the chamber. The affinity agent acts to capture a target molecule (diamonds) from a sample. The capture target molecule can then be detected by addition of an affinity agent linked to an enzyme, or as depicted in FIG. 24, a primary affinity agent specific for the captured target can be bound the target molecule and then a secondary affinity agent linked to an enzyme (plus sign) can be used to bind to the primary affinity agent. The substrate of the enzyme is shown as two circles linked by a line. The processed substrate (after acted upon by the enzyme) is shown as a dark circle and a light circle with a line, the latter representing the detectable processed substrate. At the bottom, the figure shows a later time point at which the processed substrate has been moved in an electrical field created by the electrodes (1, 2) in proximity to a second sub-area (4). The pH of the solution in proximity of the second sub-area (4) is set to a pH at or close to the pI of the detectable processed substrate by an proton or hydroxide injector (6). The detectable processed substrate can then be detected by a detector (7). This aspect can be performed in multiplex if desired by using affinity agents with different target specificity linked to different enzymes such that different detectable processed substrates can be distinguished (e.g., by wavelength, pI, or other criteria).
Figure 25:
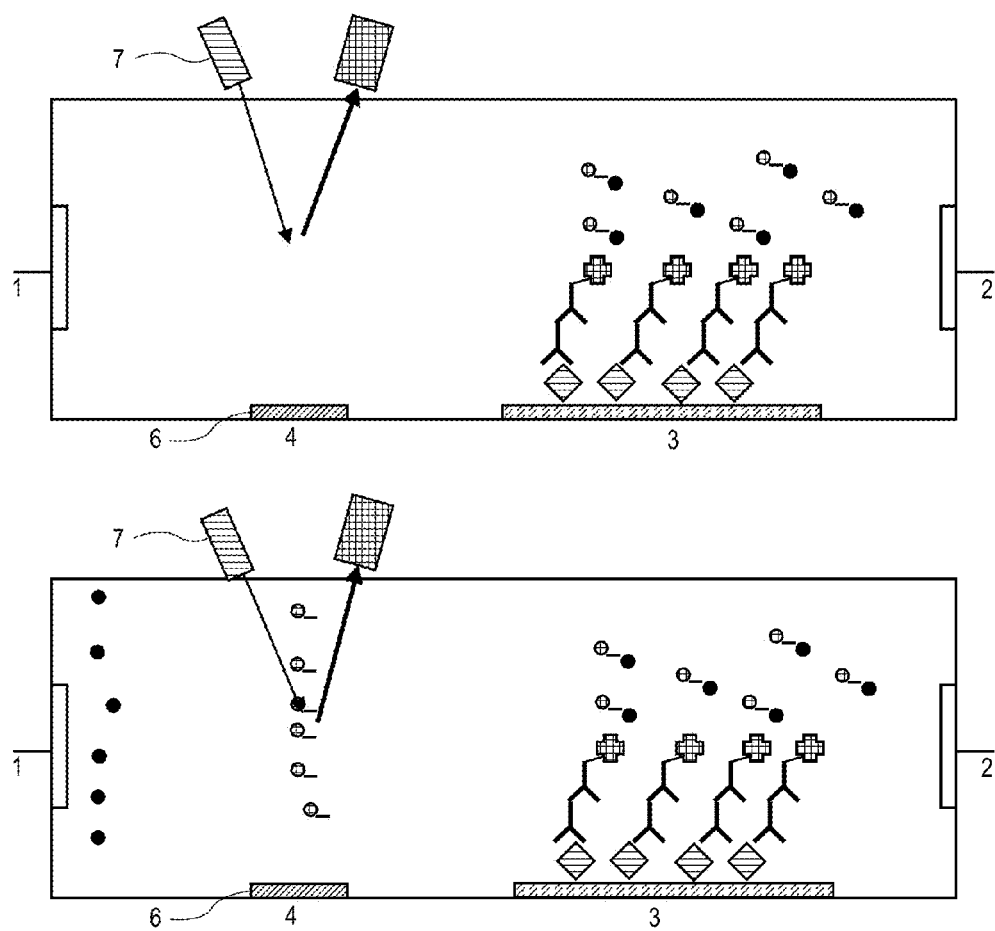
FIG. 25 schematically illustrates an apparatus configuration and its use to detect target molecules from a sample.

Another aspect is provided and is described with reference to FIGS. 24 and 25. In this aspect, the signal ultimately detected is a processed substrate of an enzyme linked to an affinity agent or a detachable label that is detached from the affinity agent. One initial format (FIG. 24) for such aspects involves a chamber having an unlabeled affinity agent linked to the first sub-area (3). The sample is added under conditions to allow target molecules in the sample to bind the affinity agents, thereby localizing the target molecules to the first sub-area. In different initial format (one aspect of which is depicted in FIG. 25), components of the sample, including the target molecule, if present, are bound to the first sub-area, either directly, or if the sample is biotinylated, via streptavidin or avidin linked to the first sub-area.

In either format, the result is that at least the target molecule is localized to the first sub-area (3). The solution in the chamber can optionally be washed to remove unbound components, and then contacted with an affinity agent comprising either an enzyme capable to altering a substrate to render it detectable (the "processed substrate) or a detectable label that is detachable from the affinity agent. In either case, the affinity agent can be used to bind to the immobilized target molecule in the first sub-area, or the labeled affinity agent can act as a secondary affinity agent with a primary affinity agent specifically binding the target molecule and the labeled secondary affinity agent binding to the primary affinity agent. An example of this latter option is the use of a mouse primary antibody to specifically bind to the target molecule and a labeled goat anti-mouse antibody as the secondary antibody. Once the labeled affinity agent is bound (directly or indirectly) to the localized target molecule, unbound molecules can be optionally washed away.

In the case of an enzyme-linked affinity agent, the substrate of the enzyme can be added under conditions such that the substrate is processed by the enzyme, thereby generating processed detectable substrate. Examples of possible enzyme/substrate pairs include, but are not limited to, horseradish peroxidase (substrates can include but are not limited to: 3,3'-diaminobenzidine (DAB), 3,3',5,5'-tetramethylbenzidine (TMB), 2,2'-Azinobis [3-ethylbenzothiazoline-6-sulfonic acid]-diammonium salt (ABST), or o-phenylenediamine dihydrochloride (OPD)), alkaline phosphatase (substrates can include but are not limited to: combination of nitro blue tetrazolium chloride (NBT) and 5-bromo-4-chloro-3-indolyl phosphate (BCIP) p-Nitrophenyl Phosphate, Disodium Salt (PNPP)), glucose oxidase (substrates can include but are not limited to: NBT), β-galactosidase (substrates can include but are not limited to: 5-bromo-4-chloro-3-indoyl-β-D-galactopyranoside (BCIG or X-Gal)), and luciferase (substrates include luciferin). The quantity of processed substrate should be proportional to the amount of target molecule in the sample.

In one aspect the processed substrate is moved in solution to the location of an electrode, where the processed substrate is detected and/or quantified. Alternatively, the processed substrate can be localized to a second sub-area of the chamber by setting the pH of the solution in proximity to the second sub-area to a pH at or close to the pI of the processed substrate. The pH of the solution in proximity to the second sub-area can be controlled, for example, by inclusion of one or more proton or hydroxide injectors (6 in FIGS. 24 and 25) at the second sub-area (4). The processed substrate can then be detected and quantified.

In other aspects, the affinity agent comprises a label that can be displaced from the affinity agent. "Can be displaced," as used in this context, means that the conditions within the chamber can be changed to specifically release the label from the affinity agent. For example, in some embodiments, the affinity agent is linked to the detectable label via a double stranded nucleic acid (e.g., dsDNA, dsRNA, or a mimetic thereof), wherein one strand is linked to the affinity agent and one strand is linked to the label. Under appropriate conditions, the double-stranded nucleic acid can be denatured, thereby displacing the label from the affinity agent. Denaturation conditions can comprise, for example, a change in the pH of the solution in proximity to the affinity agent. The change in pH can be achieved, for example, using one or more proton or hydroxide injectors in proximity to the first sub-area.

As is clear from the descriptions above, methods for detecting and/or quantifying one or more target molecule in a biological or other sample can be achieved using the apparatus described herein.

Samples can be any type of sample potentially comprising a target molecule of interest that can be bound by an affinity agent. In some embodiments, the sample is a biological sample. The target molecule refers to a molecule of interest to be detected or quantified. Target molecules can include, but are not limited to, proteins, polynucleotides (e.g., DNA or RNA), viruses, and metabolites. Examples of target proteins include but are not limited to antibodies, enzymes, growth regulators, and clotting factors.

"Affinity agents" as described herein refer to any agents (e.g., molecules) that specifically bind to an intended target. An exemplary affinity agent is an antibody (e.g., a monoclonal antibody) or fragment thereof with antigen binding specificity. Further, a number of different synthetic molecular scaffolds can be used to display the variable light and heavy chain sequences of antibodies specific for the target molecule. Moreover, random libraries of peptides, aptamers, or other molecules can be used to screen for affinity agents with specificity to a particular target molecule. A publication describing use of the fibronectin type III domain (FN3) as a specific molecular scaffold on which to display peptides including CDRS is Koide, A. et al. *J. Mol. Biol.* 284:1141 1151 (1988). Other scaffolding alternatives include, e.g., "minibodies" (Pessi, A. et al., Nature 362:367 369 (1993)), tendamistat (McConnell, S. J. and Hoess, R. H. *J. Mol. Biol.* 250:460 470 (1995)), and "camelized" VH domain (Davies J. and Riechmann, L. Bio/Technology 13:475 479 (1995)). Other scaffolds that are not based on the immunoglobulin like folded structure are reviewed in Nygren, P. A. and Uhlen, M. *Curr. Opin. Struct. Biol.* 7:463 469 (1997). U.S. Pat. No. 6,153,380 describes additional scaffolds. The term "affinity agents" encompasses molecules comprising synthetic molecular scaffolds such as those described above to display binding domains with a binding specificity for the target molecule.

The specificity of antibody binding can be defined in terms of the comparative dissociation constants (Kd) of the antibody for the target molecule as compared to the dissociation constant with respect to the antibody and other materials in the environment or unrelated molecules in general. Typically, the Kd for the antibody with respect to the unrelated material will be at least 2-fold, 3-fold, 4-fold, 5-fold, 10-fold, 20-fold, 50-fold, 100-fold, 200-fold or higher than Kd with respect to the target.

The labels used can be any label that is capable of directly or indirectly emitting or generating detectable signal. In some embodiments, the labels are fluorophores. A vast array of fluorophores are reported in the literature and thus known to those skilled in the art, and many are readily available from commercial suppliers to the biotechnology industry. Literature sources for fluorophores include Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.*, 40: 83-114 (1971); Stryer, L. *Ann. Rev. Biochem.*, 47: 819-846 (1978); Wang et al., *Tetrahedron Letters* 31: 6493-6496 (1990); Wang et al., *Anal. Chem.* 67: 1197-1203 (1995).

The following is a list of examples of fluorophores:
4-acetamido-4'-isothiocyanatostilbene-2,2' disulfonic acid
acridine
acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin
7-amino-4-methylcoumarin (AMC, Coumarin 120)
7-amino-4-trifluoromethylcoumarin (Coumaran 151)
cyanine dyes
cyanosine
4',6-diaminidino-2-phenylindole (DAPI)
5',5"-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin
eosin isothiocyanate
erythrosin B
erythrosin isothiocyanate
ethidium
5-carboxyfluorescein (FAM)
5-(4,6-dichlorotriazin-2-yl)aminofluorescein (DTAF)
2',7'-dimethoxy-4'5'-dichloro-6-carboxyfluorescein (JOE)
fluorescein
fluorescein isothiocyanate
fluorescamine
IR144
IR1446
Malachite Green isothiocyanate
4-methylumbelliferone
ortho cresolphthalein
nitrotyrosine
pararosaniline
Phenol Red
phycoerythrin (including but not limited to B and R types)
o-phthaldialdehyde
pyrene
pyrene butyrate
succinimidyl 1-pyrene butyrate
quantum dots
Reactive Red 4 (Cibacron™ Brilliant Red 3B-A)
6-carboxy-X-rhodamine (ROX)
6-carboxyrhodamine (R6G)
lissamine rhodamine B sulfonyl chloride rhodamine
rhodamine B
rhodamine 123
rhodamine X isothiocyanate
sulforhodamine B
sulforhodamine 101
sulfonyl chloride derivative of sulforhodamine 101 (Texas Red)
N,N,N',N'-tetramethyl-6-carboxyrhodamine (TAMRA)
tetramethyl rhodamine
tetramethyl rhodamine isothiocyanate (TRITC)
riboflavin
rosolic acid
lanthanide chelate derivatives If desired, the fluorophores (or other labels) can be used in combination, with a distinct labels for affinity agents with different target specificities (e.g., for multiplexing). In some embodiments, however, a single label is used for all labeled affinity agents, the assays being differentiated solely by differentiation based on pI.

The attachment of any of these fluorophores to affinity agents can be achieved by conventional covalent bonding, using appropriate functional groups on the fluorophores and on the affinity agents. The recognition of such groups and the reactions to form the linkages will be readily apparent to those skilled in the art.

As noted elsewhere herein, the methods can achieve detection of the presence or absence of a particular target molecule(s) in a sample. In some embodiments, the approximate quantity of the target molecule in the sample can be determined, for example as explained elsewhere herein.

All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

EXAMPLE

Example 1

Separation of Target(s) Based on pI

Two fluorescently-labeled peptides, one with a pI of 5.0, one with a pI of 6.8, were placed into a chamber comprising a pH 8.5 phosphate buffer. The chamber comprises two proton injectors, with the first proton injector having a current applied of 150 µA and the second proton injector having a current applied of 65 µA, thereby generating separate localized areas within the solution having different pH. In view of the higher current, the first injector generated a more acidic pH in the area of the chamber near the first injector compared to the pH near the second injector. An electric field was generated across the chamber, thereby moving charged molecules according to their charge. The pI 6.8 peptides focused on the area near the first proton injector and the pI 5.0 peptides focused on the area of the chamber near the second proton injector. This shows that molecules having different pI can be moved and isolated in different areas of a solution in a chamber using electronic control of their movement in combination with localization based on control of local pH in the solution using ion injectors.

Example 2

Precipitation/Trapping of Target(s) Based on pI

This experiment shows that some target molecules precipitate or adhere to a chamber surface when positioned at their pI (e.g., under prolonged H' injection), and that the resulting targets can subsequently be detected (e.g., immuno-detected). Green Fluorescent Protein (GFP, 1 µg) and human saliva (1.5 µg) were combined with STB 8.5 (4 mM each Sodium Citrate, Sodium Phosphate, Sodium Pyrophosphate, and 13 mM Sodium Sulfate, pH 8.5) and the resulting mixture was introduced into a chamber comprising a proton injector. The injector was set to generate a pH step encompassing the pI of GFP (~5.4) and voltage was run through the first and second electrodes across the chamber, thereby electrophoresing GFP through the chamber to the pH step, where GFP stopped due to lack of charge. GFP was 'trapped' by isoelectric focusing over a bipolar membrane (BPM) by H' injection.

Figure 14A:
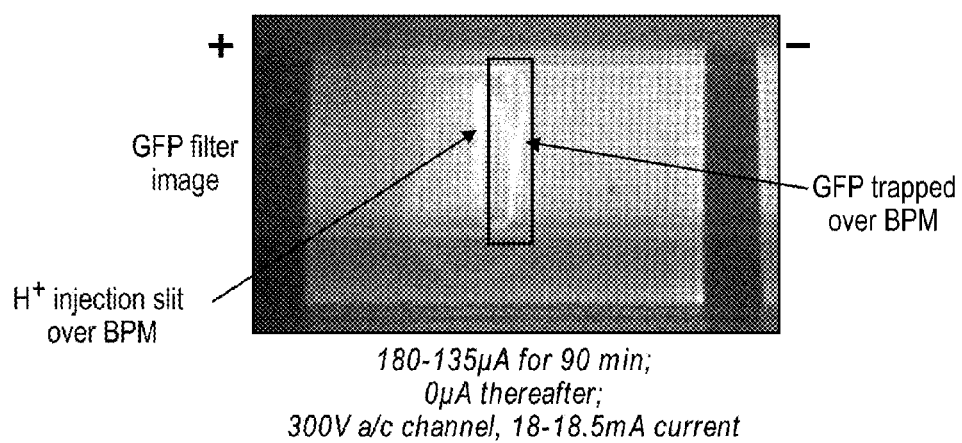
FIG. 14A represents green fluorescent protein (GFP) signal following electrophoresis in buffer and 'trapping' (e.g., adherence to the chamber or precipitation) via H' injection in the same buffer-filled chamber.
Figure 14B:
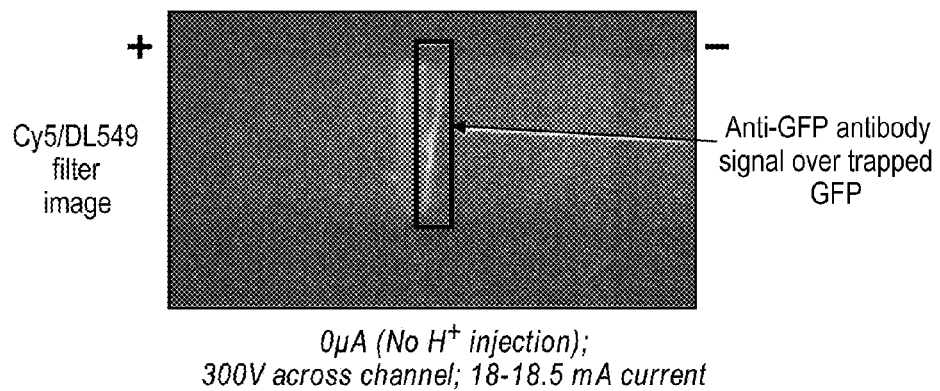
FIG. 14B illustrates CY5 signal following 'trapping' of the GFP and introduction of a CY5-labeled anti-GFP antibody.
Figure 15A:
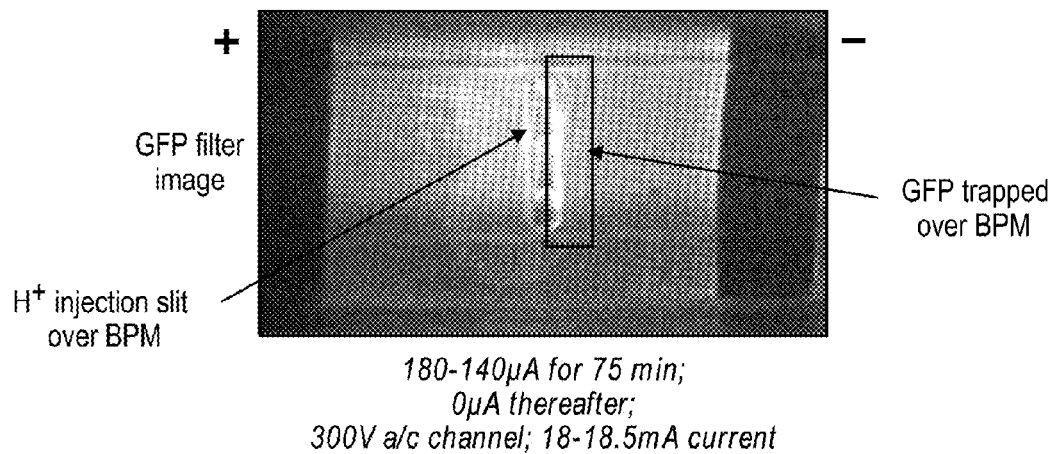
FIG. 15A represents green fluorescent protein (GFP) signal following electrophoresis in buffer and 'trapping' via H' injection in the same buffer-filled chamber. The trapped protein adhered to the chamber after prolonged injection of H' into the buffer-filled chamber.
Figure 15B:
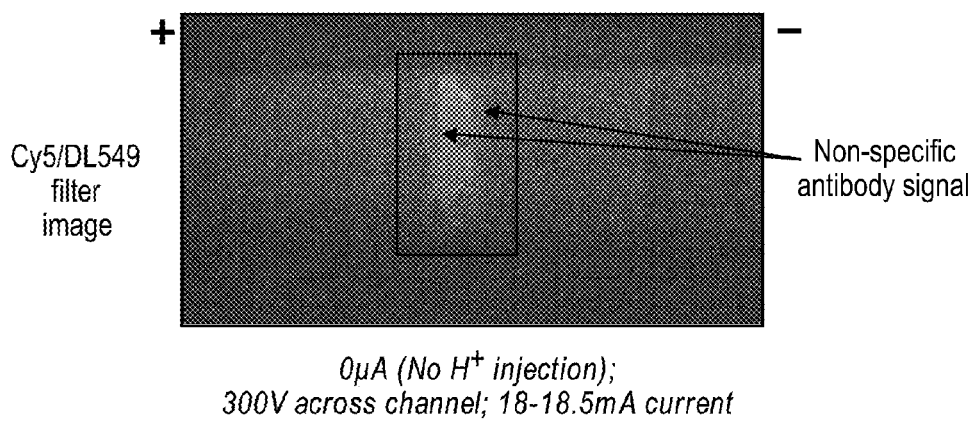
FIG. 15B illustrates CY5 signal following precipitation/adherence of the GFP and electrophoretic introduction of a CY5-labeled anti-rabbit (non-specific) antibody.

While not true for all targets, or even the same target in a different buffer composition, GFP precipitated/adhered to a chamber surface at the pH step. The voltage was subsequently turned off. As shown in FIGS. 14A and 15A, which detects GFP fluorescence, GFP localized at the pH step. Subsequently, an anti-GFP antibody labeled with Dyelight649/DL649 was introduced to the chamber and electrophoresed for 60 minutes across channel and over the GFP precipitate. Signal under a Cy5 filter, which also detects DL649 fluorescence, shows that the anti-GFP antibody localized with the GFP (FIG. 14B), demonstrating that this system detects target molecules that are localized in a pH step gradient. In contrast, FIG. 15B displays results from a parallel experiment using a non-specific anti-rabbit antibody. Only background signal was observed from the non-specific antibody.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for selectively positioning a target analyte in a solution containing a mixture of analytes, the target analyte having a pH dependent charge, the method comprising:
    providing into a chamber a sample comprising the solution containing the mixture of analytes, including the target analyte, wherein the chamber comprises a first and a second electrode and at least two proton/hydroxyl injectors positioned between the electrodes;
    generating a first pH step with one of the at least two proton/hydroxyl injectors, thereby generating a first sub-area having the first pH step, and applying an electric field across the electrodes, thereby moving a portion of the mixture of analytes to the first sub-area in the chamber based on the pH dependent charge of the target analyte, wherein the portion of the mixture of analytes comprises analytes having a range of isoelectric points from of about pH 3 or more to pH of about 10 or less; and
    generating a second pH step with the second proton/hydroxyl injector, thereby generating a second sub-area having the second pH step, wherein the second pH step is narrower than the first pH step and encompasses a pH range that includes the pI of the target analyte, thereby selectively positioning the target analyte in a sub-area near the second proton/hydroxyl injector of the chamber.

2. The method of claim 1, wherein the method comprises electronically changing the first or second pH step with the first or second proton/hyrdroxyl injector respectively, thereby re-positioning the target analyte in the chamber.

3. The method of claim 1, wherein the selectively positioning the target analyte in the chamber comprises precipitating the target analyte in the chamber at a position corresponding to the isolectric point of the target analyte.

4. The method of claim 1, wherein the method further comprises positioning an affinity agent in the chamber to contact, and bind to, the target analyte.

5. The method of claim 4, wherein the affinity agent has a different isoelectric point than the target analyte and is positioned in the same sub-area as the target analyte by the pH step generated by the second proton/hydroxyl injector and the applied electric field.

6. The method of claim 4, wherein the method further comprises washing away unbound affinity agent after the step of binding the target analyte to the affinity agent.

7. The method of claim 6, wherein the method further comprises changing the second pH step to thereby elute the affinity agent or target analyte.

8. The method of claim 7, wherein the method further comprises detecting the eluted affinity agent or target analyte.

9. The method of claim 1, wherein the first and the second pH steps are controlled by a pre-programmed set of instructions.

10. The method of claim 9, wherein the pre-programmed set of instructions are provided on a computer readable medium.

11. A method of separating a target analyte in a sample from one or more other analytes in the sample, the method comprising:
providing into a chamber the sample, including the target analyte, wherein the chamber comprises a first and a second electrode and a proton/hydroxyl injector positioned between the electrodes;
generating a first pH gradient in the chamber and applying an electric field across the electrodes, thereby moving and separating the analytes, including the target analyte, according to charge and, optionally, molecular weight; and
transiently altering the pH gradient to selectively elute the target analyte from the chamber.

12. The method of claim 11, wherein the chamber comprises a separating medium, the separating medium comprising a gel.

13. The method of claim 12, wherein the gel is a polyacrylamide gel.

14. The method of claim 11, wherein the electric field and the pH, or pH gradient of the chamber are controlled by a pre-programmed set of instructions.

15. The method of claim 14, wherein the pre-programmed set of instructions are provided on a computer readable medium.

* * * * *